United States Patent
Blomgren et al.

(10) Patent No.: US 10,093,684 B2
(45) Date of Patent: *Oct. 9, 2018

(54) SUBSTITUTED IMIDAZO[1,2-A]PYRAZINES AS SYK INHIBITORS

(71) Applicant: Gilead Connecticut, Inc., Foster City, CA (US)

(72) Inventors: Peter A. Blomgren, Issaquah, WA (US); Kevin S. Currie, North Bend, WA (US); Jeffrey E. Kropf, Issaquah, WA (US); Seung H. Lee, Sammamish, WA (US); Scott A. Mitchell, Kenmore, WA (US); Douglas G. Stafford, Niskayuna, NY (US); Jianjun Xu, Seattle, WA (US)

(73) Assignee: Gilead Connecticut, Inc., Foster City, CA (US)

( * ) Notice: Subject to any disclaimer, the term of this patent is extended or adjusted under 35 U.S.C. 154(b) by 0 days.

This patent is subject to a terminal disclaimer.

(21) Appl. No.: 15/404,120

(22) Filed: Jan. 11, 2017

(65) Prior Publication Data

US 2017/0121350 A1 May 4, 2017

Related U.S. Application Data

(60) Continuation of application No. 14/629,390, filed on Feb. 23, 2015, now Pat. No. 9,567,348, which is a division of application No. 13/862,194, filed on Apr. 12, 2013, now Pat. No. 8,962,835, which is a division of application No. 12/632,151, filed on Dec. 7, 2009, now Pat. No. 8,440,667.

(60) Provisional application No. 61/240,983, filed on Sep. 9, 2009, provisional application No. 61/140,535, filed on Dec. 23, 2008, provisional application No. 61/120,590, filed on Dec. 8, 2008.

(51) Int. Cl.
| | |
|---|---|
| *A61K 31/4985* | (2006.01) |
| *C07D 487/04* | (2006.01) |
| *C07D 519/00* | (2006.01) |
| *C07D 471/04* | (2006.01) |
| *A61K 9/00* | (2006.01) |

(52) U.S. Cl.
CPC .......... *C07D 519/00* (2013.01); *A61K 9/0053* (2013.01); *C07D 471/04* (2013.01); *C07D 487/04* (2013.01); *G01N 2333/9121* (2013.01)

(58) Field of Classification Search
CPC ........................ A61K 31/4985; C07D 487/04
USPC ............................ 514/249; 544/350; 546/304
See application file for complete search history.

(56) References Cited

U.S. PATENT DOCUMENTS

| | | | |
|---|---|---|---|
| 4,337,609 | A | 7/1982 | Foster et al. |
| 5,593,997 | A | 1/1997 | Dow et al. |
| 5,658,857 | A | 8/1997 | Andree et al. |
| 5,783,576 | A | 7/1998 | Roos et al. |
| 5,846,514 | A | 12/1998 | Foster et al. |
| 6,334,997 | B1 | 1/2002 | Foster et al. |
| 6,919,340 | B2 | 7/2005 | Currie et al. |
| 6,919,341 | B2 | 7/2005 | Paruch et al. |
| 7,160,885 | B2 | 1/2007 | Currie et al. |
| 7,189,723 | B2 | 3/2007 | Mitchell et al. |
| 7,259,164 | B2 | 8/2007 | Mitchell et al. |
| 7,312,341 | B2 | 12/2007 | DeSimone et al. |
| 7,393,848 | B2 | 7/2008 | Currie et al. |
| 7,405,295 | B2 | 7/2008 | Currie et al. |
| 7,657,023 | B2 | 2/2010 | Reed et al. |
| 8,440,667 | B2 | 5/2013 | Mitchell et al. |
| 8,450,321 | B2 | 5/2013 | Mitchell et al. |
| 8,455,493 | B2 | 6/2013 | Mitchell et al. |
| 8,697,699 | B2 | 4/2014 | Mitchell et al. |
| 8,748,607 | B2 | 6/2014 | Mitchell et al. |
| 8,765,761 | B2 | 7/2014 | Mitchell et al. |
| 8,796,270 | B2 | 8/2014 | Mitchell et al. |

(Continued)

FOREIGN PATENT DOCUMENTS

| | | |
|---|---|---|
| CA | 2175837 A1 | 5/1995 |
| CA | 2714414 A1 | 8/2009 |

(Continued)

OTHER PUBLICATIONS

U.S. Appl. No. 14/074,665, filed Nov. 7, 2013, Mitchell et al.

(Continued)

*Primary Examiner* — Douglas M Willis
(74) *Attorney, Agent, or Firm* — Sheppard Mullin Richter & Hampton LLP

(57) ABSTRACT

Certain imidazopyrazines of Formula I and pharmaceutical compositions thereof are provided herein:

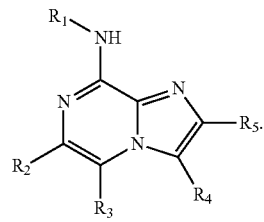

Methods of treating patients suffering from certain diseases and disorders responsive to the inhibition of Syk activity, which comprises administering to such patients an amount of at least one chemical entity effective to reduce signs or symptoms of the disease or disorder are provided. Also provided are methods for determining the presence or absence of Syk kinase in a sample.

10 Claims, No Drawings

(56) References Cited

U.S. PATENT DOCUMENTS

| | | |
|---|---|---|
| 8,962,835 B2 | 2/2015 | Mitchell et al. |
| 9,120,811 B2 | 9/2015 | Mitchell et al. |
| 9,212,191 B2 | 12/2015 | Mitchell et al. |
| 9,290,505 B2 | 3/2016 | Blomgren et al. |
| 9,376,441 B2 | 6/2016 | Currie et al. |
| 9,382,256 B2 | 7/2016 | Casteel et al. |
| 9,504,684 B2 | 11/2016 | Blomgren et al. |
| 9,562,056 B2 | 2/2017 | Blomgren et al. |
| 9,567,348 B2 | 2/2017 | Mitchell et al. |
| 9,657,023 B2 | 5/2017 | Elford et al. |
| 9,687,492 B2 | 6/2017 | Di Paolo et al. |
| 9,707,236 B2 | 7/2017 | Di Paolo et al. |
| 9,796,718 B2 | 10/2017 | Mitchell et al. |
| 2003/0089434 A1 | 5/2003 | Flynn et al. |
| 2003/0212073 A1 | 11/2003 | Currie et al. |
| 2004/0022562 A1 | 2/2004 | Nakamura et al. |
| 2004/0026310 A1 | 2/2004 | Larsen |
| 2004/0026867 A1 | 2/2004 | Adams et al. |
| 2004/0026877 A1 | 2/2004 | Taylor et al. |
| 2004/0063715 A1 | 4/2004 | Paruch et al. |
| 2004/0067951 A1 | 4/2004 | DeSimone et al. |
| 2004/0072080 A1 | 4/2004 | Iwanaga et al. |
| 2004/0072081 A1 | 4/2004 | Coleman et al. |
| 2004/0072835 A1 | 4/2004 | Paruch et al. |
| 2004/0102455 A1 | 5/2004 | Burns et al. |
| 2004/0220189 A1 | 11/2004 | Sun et al. |
| 2005/0005429 A1 | 1/2005 | Yi et al. |
| 2005/0009832 A1 | 1/2005 | Sun et al. |
| 2005/0014599 A1 | 1/2005 | Tay |
| 2005/0019220 A1 | 1/2005 | Napoli |
| 2005/0047290 A1 | 3/2005 | Okada et al. |
| 2005/0054648 A1 | 3/2005 | Mitchell et al. |
| 2005/0054649 A1 | 3/2005 | Currie et al. |
| 2005/0085252 A1 | 4/2005 | Reyes |
| 2005/0085484 A1 | 4/2005 | Mitchell et al. |
| 2005/0090499 A1 | 4/2005 | Currie et al. |
| 2005/0101604 A1 | 5/2005 | Currie et al. |
| 2005/0288295 A1 | 12/2005 | Currie et al. |
| 2006/0044687 A1 | 3/2006 | Soeno et al. |
| 2006/0053121 A1 | 3/2006 | Zizys et al. |
| 2006/0069084 A1* | 3/2006 | Burns ............... A61K 31/435 514/218 |
| 2006/0084650 A1 | 4/2006 | Dong et al. |
| 2006/0148796 A1 | 7/2006 | Zimmermann et al. |
| 2006/0183746 A1 | 8/2006 | Currie et al. |
| 2007/0105864 A1 | 5/2007 | Guzi et al. |
| 2007/0117804 A1 | 5/2007 | Zhao et al. |
| 2008/0025821 A1 | 1/2008 | White et al. |
| 2009/0077334 A1 | 3/2009 | Ishida et al. |
| 2009/0102468 A1 | 4/2009 | Takahashi et al. |
| 2009/0221612 A1 | 9/2009 | Mitchell et al. |
| 2010/0006947 A1 | 1/2010 | Becker et al. |
| 2010/0027500 A1 | 2/2010 | Schulz et al. |
| 2010/0068257 A1 | 3/2010 | Boni et al. |
| 2010/0068258 A1 | 3/2010 | Cardona Iglesias et al. |
| 2010/0152159 A1 | 6/2010 | Mitchell et al. |
| 2010/0222323 A1 | 9/2010 | Mitchell et al. |
| 2011/0112995 A1 | 5/2011 | Chang et al. |
| 2012/0220582 A1 | 8/2012 | Mitchell et al. |
| 2013/0023499 A1 | 1/2013 | Mitchell et al. |
| 2013/0210802 A1 | 8/2013 | Blomgren et al. |
| 2013/0231330 A1 | 9/2013 | Mitchell et al. |
| 2013/0237520 A1 | 9/2013 | Mitchell et al. |
| 2013/0237521 A1 | 9/2013 | Mitchell et al. |
| 2013/0267496 A1 | 10/2013 | Mitchell et al. |
| 2013/0310363 A1 | 11/2013 | Mitchell et al. |
| 2014/0148430 A1 | 5/2014 | Blomgren et al. |
| 2015/0038488 A1 | 2/2015 | Currie et al. |
| 2015/0175616 A1 | 6/2015 | Blomgren et al. |
| 2016/0166580 A1 | 6/2016 | Casteel et al. |
| 2016/0168155 A1 | 6/2016 | Casteel et al. |
| 2016/0220573 A1 | 8/2016 | Di Paolo et al. |
| 2016/0310490 A1 | 10/2016 | Blomgren et al. |
| 2016/0368918 A1 | 12/2016 | Blomgren et al. |
| 2016/0375019 A1 | 12/2016 | Di Paolo et al. |
| 2017/0020821 A1 | 1/2017 | Casteel et al. |
| 2017/0035755 A1 | 2/2017 | Blomgren et al. |
| 2017/0095490 A1 | 4/2017 | Blomgren et al. |
| 2017/0121350 A1 | 5/2017 | Blomgren et al. |
| 2017/0217967 A1 | 8/2017 | Elford et al. |
| 2017/0258804 A1 | 9/2017 | Di Paolo et al. |
| 2018/0008608 A1 | 1/2018 | Di Paolo et al. |
| 2018/0071302 A1 | 3/2018 | Abella et al. |
| 2018/0071303 A1 | 3/2018 | Abella et al. |
| 2018/0086769 A1 | 3/2018 | Armistead et al. |
| 2018/0099971 A1 | 4/2018 | Elford et al. |
| 2018/0117052 A1 | 5/2018 | Di Paolo et al. |

FOREIGN PATENT DOCUMENTS

| | | |
|---|---|---|
| CN | 101124227 A | 2/2008 |
| CN | 101287736 A2 | 10/2008 |
| DE | 4337609 A1 | 5/1995 |
| EA | 2005-01229 A1 | 4/2006 |
| EP | 480713 A1 | 4/1992 |
| JP | 2001-302667 A | 10/2001 |
| JP | 2004-0528295 | 9/2004 |
| JP | 2004-528295 A | 9/2004 |
| JP | 2005-0530739 | 10/2005 |
| JP | 2005-530739 A | 10/2005 |
| JP | 2007-504241 A | 3/2007 |
| JP | 2008-0519843 | 6/2008 |
| JP | 2008-519843 A | 6/2008 |
| JP | 2010-546786 | 4/2011 |
| JP | 2011-0511835 | 4/2011 |
| JP | 2011-511835 A | 4/2011 |
| JP | 2012-510997 | 5/2012 |
| JP | 2012-510998 A | 5/2012 |
| NZ | 593460 A | 11/2013 |
| WO | WO-88/04298 A1 | 6/1988 |
| WO | WO-95/12594 A1 | 5/1995 |
| WO | WO-96/04298 A1 | 2/1996 |
| WO | WO-96/34866 A1 | 11/1996 |
| WO | WO-99/28322 A1 | 6/1999 |
| WO | WO-01/027119 A2 | 4/2001 |
| WO | WO-2001/27119 | 4/2001 |
| WO | WO-01/083485 A1 | 11/2001 |
| WO | WO-02/010170 A1 | 2/2002 |
| WO | WO-02/030428 A1 | 4/2002 |
| WO | WO-02/066481 A1 | 8/2002 |
| WO | WO-2002/060492 | 8/2002 |
| WO | WO-02/076985 A1 | 10/2002 |
| WO | WO-03/070732 A1 | 8/2003 |
| WO | WO-2003/089434 A2 | 10/2003 |
| WO | WO-2004/022562 A1 | 3/2004 |
| WO | WO-2004/026310 A1 | 4/2004 |
| WO | WO-2004/026867 A2 | 4/2004 |
| WO | WO-2004/026877 A1 | 4/2004 |
| WO | WO-2004/072080 A1 | 8/2004 |
| WO | WO-2004/072081 A1 | 8/2004 |
| WO | WO-2005/005429 A1 | 1/2005 |
| WO | WO-2005/014599 A1 | 2/2005 |
| WO | WO-2005/019220 A2 | 3/2005 |
| WO | WO-2005-023759 | 3/2005 |
| WO | WO-2005/047290 A2 | 5/2005 |
| WO | WO-2005/085252 A1 | 9/2005 |
| WO | WO-2006/044687 A2 | 4/2006 |
| WO | WO-2006/053121 A2 | 5/2006 |
| WO | WO-2007-008541 | 1/2007 |
| WO | WO-2008/025821 A1 | 3/2008 |
| WO | WO-2008-065199 | 6/2008 |
| WO | WO-2009/077334 A1 | 6/2009 |
| WO | WO-2009/102468 A1 | 8/2009 |
| WO | WO-2009-155388 | 12/2009 |
| WO | WO-2010/006947 A1 | 1/2010 |
| WO | WO-2010/006970 A1 | 1/2010 |
| WO | WO-2010/027500 A1 | 3/2010 |
| WO | WO-2010/068257 A1 | 6/2010 |

(56) References Cited

FOREIGN PATENT DOCUMENTS

| | | |
|---|---|---|
| WO | WO-2010/068258 A1 | 6/2010 |
| WO | WO-2011/112995 A1 | 9/2011 |

OTHER PUBLICATIONS

Al-Dabbagh, S. G. et al. (1984). "Species Differences in Oxidative Drug Metabolism: Some Basic Considerations." Archives of Toxicology. Supplement. Archive fur Toxikologie. Supplement, 7:219-231.

Bundgaard, H., (1985). *Design of Prodrugs*, Elsevier Science Publishers, B.V., The Netherlands, p. 1.

Dean, D.C. (2000). "Recent Advances in the Synthesis and Applications of Radiolabeled Compounds for Drug Discovery and Development," *Curr. Pharm Des.* 6(10): Preface, 1 page.

Ding, S. et al. (2002) "A Combinatorial Scaffold Approach Toward Kinase-Directed Heterocycle Libraries," *J. Am Chem Soc.,* 124(8):1594-1596.

European Communication dated Jun. 18, 2013, for EP Patent Application No. 11 709 600.8 filed on Mar. 11, 2011, 6 pages.

European Communication dated Jun. 6, 2013, for EP Patent Application No. 09 832 228.2 filed on Jun. 21, 2011, 5 pages.

European Communication dated Oct. 24, 2012, for European Patent Application No. 09710901.1, filed on Feb. 12, 2009, five pages.

Evans, E.A. (1981). "Synthesis of Radiolabeled Compounds," *J. Radioanal. Chem.* 64(1-2):9-32.

Extended European Search Report dated Apr. 26, 2012, for EP 09 83 2229, filed on Jun. 21, 2011, 6 pages.

Extended European Search Report dated Jul. 27, 2012, for EP 09 83 2228.2, filed on Jun. 21, 2011, 12 pages.

Extended European Search Report dated Mar. 12, 2014, for EP 13005979.3, filed on Dec. 20, 2013, 5 pages.

Final Office Action dated Jan. 27, 2012, for U.S. Appl. No. 12/632,151, filed Dec. 7, 2009, 15 pages.

Final Office Action dated May 2, 2013 for U.S. Appl. No. 13/343,624, filed Jan. 4, 2012, 9 pages.

Final Office Action dated May 25, 2012, for U.S. Appl. No. 12/632,140, filed Dec. 7, 2009, 9 pages.

Final Office Action dated Oct. 30, 2012, for U.S. Appl. No. 12/632,140, filed Dec. 7, 2009, 9 pages.

Final Office Action dated Sep. 15, 2011, for U.S. Appl. No. 12/632,140, filed Dec. 7, 2009, 15 pages.

Final Office Action dated Sep. 5, 2012, for U.S. Appl. No. 12/632,151, filed Dec. 7, 2009, 11 pages.

GenBank Accession No. AY050647.1, created on Oct. 7, 2001, located at <http://www.ncbi.nlm.nih.gov/nuccore/AY050647.1>, last visited on Dec. 28, 2011, 1 page.

International Preliminary Examination Report dated Aug. 5, 2004, for PCT Application No. PCT/US2003/12222, filed Apr. 21, 2003, 11 pages.

International Preliminary Examination Report dated Oct. 27, 2004, for PCT Application No. PCT/US2003/28329, filed on Sep. 9, 2003, 5 pages.

International Preliminary Report on Patentability dated Jan. 5, 2011, for PCT Application No. PCT/US2009/006445, filed on Dec. 7, 2009, 6 pages.

International Preliminary Report on Patentability dated Jun. 8, 2011, for PCT Application No. PCT/US/2009/006446, filed on Dec. 7, 2009, 6 pages.

International Preliminary Report on Patentability dated May 12, 2009, for PCT Application No. PCT/US2009/000919, filed on Feb. 12, 2009, 8 pages.

International Search Report and Written Opinion dated Dec. 30, 2004, for PCT Application No. PCT/US2004/018227, filed on Jun. 4, 2004, 10 pages.

International Search Report and Written Opinion dated Dec. 8, 2004, for PCT Application No. PCT/US2004/021150, filed on Jun. 30, 2004, 10 pages.

International Search Report and Written Opinion dated Feb. 1, 2005 for PCT Application No. PCT/US2004/025884, filed on Aug. 11, 2004, 8 pages.

International Search Report and Written Opinion dated Jul. 7, 2004, for PCT Application No. PCT/US2004/003922, filed on Feb. 10, 2004, 12 pages.

International Search Report and Written Opinion dated Jul. 7, 2004, for PCT Application No. PCT/US2004/003923, filed on Feb. 10, 2004, 12 pages.

International Search Report and Written Opinion dated Jun. 23, 2005, for PCT Application No. PCT/US2004/037433, filed on Nov. 10, 2004, 15 pages.

International Search Report dated Apr. 26, 2011, for Application No. PCT/US2011/028194, filed on Mar. 11, 2011, 5 pages.

International Search Report dated Feb. 12, 2010, for PCT Application No. PCT/US/2009/006446, filed on Dec. 7, 2009, 3 pages.

International Search Report dated Feb. 12, 2010, for PCT Application No. PCT/US2009/006445, filed on Dec. 7, 2009, 3 pages.

International Search Report dated Feb. 9, 2004, for PCT Application No. PCT/US2003/28329, filed on Sep. 9, 2003.

International Search Report dated May 12, 2009, for PCT Application No. PCT/US2009/000919, filed on Feb. 12, 2009, 5 pages.

International Search Report dated Oct. 22, 2003, for PCT Application No. PCT/US2003/12222, filed on Apr. 21, 2003.

Invitation to Pay Additional Fees with Partial International Search Report dated May 3, 2005, for PCT Application No. PCT/US2004/037433, filed on Nov. 10, 2004, 9 pages.

Japanese Decision of Patent dated Feb. 4, 2014, for Japanese Patent Application No. 2010-546786, filed on Aug. 1, 2010, 4 pages. (with English translation).

Japanese Notice of Reasons for Rejection dated Feb. 4, 2014 for Japanese Patent Application No. 2011-539524, filed on Jun. 6, 2011, 10 pages. (with English translation).

Japanese Notice of Reasons for Rejection dated Feb. 6, 2014, for Japanese Patent Application No. 2011-539525, filed on Jun. 6, 2011, 11 pages. (with English translation).

Jeffrey,T.K. et al. (1998). "Phosphodiesterase III and V Inhibitors on Pulmonary Artery from Pulmonary Hypertensive Rats: Differences Between Early and established Pulmonary Hypertension", *J. Cardiovascular Pharmacology,* 32(2): 213-219.

Jordan, V.C. (Mar. 2003). "Tamoxifen: A Most Unlikely Pioneering Medicine" *Nature Reviews: Drug Discovery* 2:205-213.

Kabalka, G.W. et al. (1989). "The Synthesis of Radiolabeled Compounds via Organometallic Intermediates," *Tetrahedron* 45(21):6601-21.

Kuhnz, W. et al. (Jun. 11, 1998). "Predicting the Oral Bioavailability of 19-Nortestosterone Progestins In Vivo From Their Metabolic Stability in Human Liver Microsomal Preparation In Vitro," *The American Society for Pharmacology and Experimental Therapeutics* 26(11)1120-1127.

Lumma, Jr., W.C. et al. (1983) "Piperazinylimidazo [1,2-a]pyrazines with Selective affinity for in Vitro a-Adrenergic Receptor Subtypes," *J. Med. Chem.* 26(3):357-363.

Non-Final Office Action dated Apr. 13, 2011 for U.S. Appl. No. 12/370,103, filed Feb. 12, 2009, 11 pages.

Non-Final Office Action dated Apr. 3, 2006, for U.S. Appl. No. 10/776,002, filed Feb. 10, 2004, 13 pages.

Non-Final Office Action dated Dec. 31, 2013, for U.S. Appl. No. 13/901,523, filed May 23, 2013, 22 pages.

Non-Final Office Action dated Feb. 17, 2012 for U.S. Appl. No. 12/632,140, filed Dec. 7, 2009, 11 pages.

Non-Final Office Action dated Jan. 25, 2013, for U.S. Appl. No. 13/343,624, filed Jan. 4, 2012, 18 pages.

Non-Final Office Action dated Jan. 8, 2007, for U.S. Appl. No. 10/915,696, filed Aug. 11, 2004, 8 pages.

Non-Final Office Action dated Jun. 29, 2011, for U.S. Appl. No. 12/632,151, filed Dec. 7, 2009, 17 pages.

Non-Final Office Action dated May 10, 2011 for U.S. Appl. No. 12/632,140, filed Dec. 7, 2009, 18 pages.

Non-Final Office Action dated May 17, 2012, for U.S. Appl. No. 12/632,151, filed Dec. 7, 2009, 15 pages.

Non-Final Office Action dated May 24, 2006, for U.S. Appl. No. 10/776,631, filed Feb. 10, 2004, 10 pages.

(56) References Cited

OTHER PUBLICATIONS

Non-Final Office Action dated Nov. 4, 2013, for U.S. Appl. No. 13/862,147, filed Apr. 12, 2013, 18 pages.
Non-Final Office Action dated Oct. 11, 2012, for U.S. Appl. No. 13/441,441, filed Apr. 6, 2012, 8 pages.
Non-Final Office Action dated Oct. 11, 2013, for U.S. Appl. No. 13/868,967, filed Apr. 23, 2013, 17 pages.
Non-Final Office Action dated Oct. 16, 2013, for U.S. Appl. No. 13/868,971, filed Apr. 23, 2013, 16 pages.
Non-Final Office Action dated Sep. 26, 2006, for U.S. Appl. No. 10/658,121, filed Sep. 9, 2003, 7 pages.
Notice of Allowance dated Apr. 20, 2007, for U.S. Appl. No. 10/915,696, filed Aug. 11, 2004, 7 pages.
Notice of Allowance dated Aug. 11, 2006, for U.S. Appl. No. 10/776,002, filed Feb. 10, 2004, 10 pages.
Notice of Allowance dated Aug. 8, 2007, for U.S. Appl. No. 10/658,121, filed Sep. 9, 2003, 4 pages.
Notice of Allowance dated Mar. 6, 2007, for U.S. Appl. No. 10/658,121, filed Sep. 9, 2003, 6 pages.
Notice of Allowance dated Aug. 12, 2013, for U.S. Appl. No. 13/343,624, filed Jan. 4, 2012, 9 pages.
Notice of Allowance dated Dec. 26, 2013, for U.S. Appl. No. 13/343,624, filed Jan. 4, 2012, 10 pages.
Notice of Allowance dated Feb. 12, 2014, for U.S. Appl. No. 13/862,147, filed Apr. 12, 2013, 9 pages.
Notice of Allowance dated Feb. 5, 2014, for U.S. Appl. No. 13/868,967, filed Apr. 23, 2013, 8 pages.
Notice of Allowance dated Jan. 14, 2013, for U.S. Appl. No. 12/632,151, filed Dec. 7, 2009, 8 pages.
Notice of Allowance dated Jan. 25, 2013, for U.S. Appl. No. 12/632,140, filed Dec. 7, 2009, 8 pages.
Notice of Allowance dated Jan. 28, 2013, for U.S. Appl. No. 13/441,441, filed Apr. 6, 2012, 8 pages.
Notice of Allowance dated Jan. 30, 2014, for U.S. Appl. No. 13/868,971, filed Apr. 23, 2013, 8 pages.
Notice of Allowance dated Sep. 7, 2006, for U.S. Appl. No. 10/776,631, filed Feb. 10, 2004, 7 pages.
Office Action dated May 19, 2016 for Israeli Appl. No. 242955 (not translated).
Oravcova, J. et al. (1996). "Drug-Protein Binding Studies New Trends in Analytical and Experimental Methodology," *J Chromatogr B* 677:1-28.
Restriction Requirement dated Dec. 8, 2010, for U.S. Appl. No. 12/632,140, filed Dec. 7, 2009, 10 pages.
Restriction Requirement dated Jan. 27, 2006, for U.S. Appl. No. 10/776,631, filed Feb. 10, 2004, 6 pages.
Restriction Requirement dated Jan. 30, 2006, for U.S. Appl. No. 10/658,121, filed Sep. 9, 2003, 5 pages.
Restriction Requirement dated Jan. 4, 2006, for U.S. Appl. No. 10/776,002, filed Feb. 10, 2004, 7 pages.
Restriction Requirement dated May 18, 2006, for U.S. Appl. No. 10/658,121, filed Sep. 9, 2003, 5 pages.
Restriction Requirement dated Oct. 13, 2006, for U.S. Appl. No. 10/915,696, filed Aug. 11, 2004, 5 pages.
Restriction Requirement dated Oct. 20, 2004, for U.S. Appl. No. 10/419,682, filed Apr. 21, 2003, 9 pages.
Restriction Requirement dated Apr. 14, 2014, for U.S. Appl. No. 13/862,194, filed Apr. 12, 2013, 5 pages.
Restriction Requirement dated Dec. 8, 2010, for U.S. Appl. No. 12/632,151, filed Dec. 7, 2009, 10 pages.
Restriction Requirement dated Feb. 17, 2011, for U.S. Appl. No. 12/370,103, filed Feb. 12, 2009, 10 pages.
Restriction Requirement dated Jan. 27, 2014, for U.S. Appl. No. 13/609,068, filed Nov. 26, 2012, 8 pages.
Restriction Requirement dated Jul. 26, 2012, for U.S. Appl. No. 13/441,441, filed Apr. 6, 2012, 9 pages.
Restriction Requirement dated Jul. 3, 2013, for U.S. Appl. No. 13/868,971, filed Apr. 23, 2013, 5 pages.
Restriction Requirement dated Jun. 14, 2013, for U.S. Appl. No. 13/862,147, filed Apr. 12, 2013, 10 pages.
Restriction Requirement dated Jun. 24, 2013, for U.S. Appl. No. 13/868,967, filed Apr. 23, 2013, 10 pages.
Restriction Requirement dated Nov. 27, 2012, for U.S. Appl. No. 13/343,624, filed Jan. 4, 2012, 10 pages.
Restriction Requirement dated Oct. 15, 2013, for U.S. Appl. No. 13/901,523, filed May 23, 2013, 5 pages.
Restriction Requirement dated Sep. 8, 2014, for U.S. Appl. No. 14/274,618, filed May 9, 2014, 6 pages.
Search Report and Written Opinion dated Mar. 9, 2016 for Singapore Appl. No. 2013090949.
Second Written Opinion dated Apr. 13, 2004, for PCT Application No. PCT/US2003/12222, filed Apr. 21, 2003, 7 pages.
Silverman, R.B. (1992), *The Organic Chemistry of Drug Design and Drug Action,* Academic Press, Inc. San Diego, CA, pp. 352-400.
Stenberg, K.A.E. et al., (2000). "KinMutBase, a Database of Human Disease-Causing Protein Kinase Mutations", *Nucleic Acids Research* 28(1):369-371.
Taylor, R. et al., (1984). "Hydrogen-Bond Geometry in Organic Crystals", *Acc. Chem Res.* 17:320-326.
Vitse, O. et al. (1999). "New Imidazo [1,2-α]pyrazine Derivatives with Bronchodilatory and Cyclic Nucleotide Phosphodiesterase Inhibitory Activities," *Bioorganic and Medicinal Chemistry* 7:1059-1065.
Written Opinion dated Apr. 26, 2011, for Application No. PCT/US2011/028194, filed on Mar. 11, 2011, 6 pages.
Written Opinion dated Dec. 5, 2003, for PCT Application No. PCT/US2003/12222, filed Apr. 21, 2003, 6 pages.
Written Opinion dated Jul. 6, 2004, for PCT Application No. PCT/US2003/28329, filed on Sep. 9, 2003, 5 pages.
Written Opinion dated Feb. 12, 2010, for PCT Application No. PCT/US2009/006445, filed on Dec. 7, 2009, 4 pages.
Written Opinion dated Feb. 12, 2010, for PCT Application No. PCT/US/2009/006446, filed on Dec. 7, 2009, 4 pages.
Written Opinion dated May 12, 2009, for PCT Application No. PCT/US2009/000919, filed on Feb. 12, 2009, 7 pages.
Zaragoza, Design, D.F. (2005). *Side Reactions in Organic Synthesis: A Guide to Successful Synthesis Design,* Weinheim;WILEY-VCH Verlag GmbH &Co. KGaA, Preface, 2 pages.
U.S. Appl. No. 15/622,737, filed Jun. 14, 2017, Gilead Sciences, Inc.
U.S. Appl. No. 15/705,139, filed Sep. 14, 2017, Gilead Sciences, Inc.
U.S. Appl. No. 15/705,159, filed Sep. 14, 2017, Gilead Sciences, Inc.
U.S. Appl. No. 15/719,399, filed Sep. 28, 2017, Gilead Connecticut, Inc.
U.S. Appl. No. 15/788,583, filed Oct. 19, 2017, Gilead Connecticut, Inc.
Hackam, D.G. et al. (2006). "Translation of Research Evidence from Animals to Humans," JAMA 296(14):1731-1732.
Non-Final Office Action dated Dec. 8, 2014 for U.S. Appl. No. 14/274,518, filed May 9, 2014, 9 pages.
Examination Report dated Jul. 10, 2017 for Australian Application No. 2016202807.

* cited by examiner

SUBSTITUTED IMIDAZO[1,2-A]PYRAZINES AS SYK INHIBITORS

CROSS-REFERENCE TO RELATED APPLICATIONS

This application is a continuation of U.S. patent application Ser. No. 14/629,390, filed Feb. 23, 2015, which is a divisional of U.S. patent application Ser. No. 13/862,194 (now U.S. Pat. No. 8,962,835), filed Apr. 12, 2013, which is a divisional of U.S. patent application Ser. No. 12/632,151 (now U.S. Pat. No. 8,440,667), filed Dec. 7, 2009, which claims priority to and the benefit of provisional U.S. Patent Application No. 61/120,590, filed Dec. 8, 2008, provisional U.S. Patent Application No. 61/140,535, filed Dec. 23, 2008, and provisional U.S. Patent Application No. 61/240,983, filed Sep. 9, 2009, each of which is hereby incorporated by reference.

FIELD

Provided herein are certain imidazopyrazines, compositions, and methods of their manufacture and use.

BACKGROUND

Protein kinases, the largest family of human enzymes, encompass well over 500 proteins. Spleen Tyrosine Kinase (Syk) is a member of the Syk family of tyrosine kinases, and is a regulator of early B-cell development as well as mature B-cell activation, signaling, and survival.

Syk is a non-receptor tyrosine kinase that plays critical roles in immunoreceptor- and integrin-mediated signaling in a variety of cell types, including B cells, macrophages, monocytes, mast cells, eosinophils, basophils, neutrophils, dendritic cells, T cells, natural killer cells, platelets, and osteoclasts. Immunoreceptors as described here include classical immunoreceptors and immunoreceptor-like molecules. Classical immunoreceptors include B-cell and T-cell antigen receptors as well as various immunoglobulin receptors (Fc receptors). Immunoreceptor-like molecules are either structurally related to immunoreceptors or participate in similar signal transduction pathways and are primarily involved in non-adaptive immune functions, including neutrophil activation, natural killer cell recognition, and osteoclast activity. Integrins are cell surface receptors that play key roles in the control of leukocyte adhesion and activation in both innate and adaptive immunity.

Ligand binding leads to activation of both immunoreceptors and integrins, which results in Src family kinases being activated, and phosphorylation of immunoreceptor tyrosine-based activation motifs (ITAMs) in the cytoplasmic face of receptor-associated transmembrane adaptors. Syk binds to the phosphorylated ITAM motifs of the adaptors, leading to activation of Syk and subsequent phosphorylation and activation of downstream signaling pathways.

Syk is essential for B-cell activation through B-cell receptor (BCR) signaling. SYK becomes activated upon binding to phosphoryated BCR and thus initiates the early signaling events following BCR activation. B-cell signaling through BCR can lead to a wide range of biological outputs, which in turn depend on the developmental stage of the B-cell. The magnitude and duration of BCR signals must be precisely regulated. Aberrant BCR-mediated signaling can cause disregulated B-cell activation and/or the formation of pathogenic auto-antibodies leading to multiple autoimmune and/or inflammatory diseases. Mice lacking Syk show impaired maturation of B-cells, diminished immunoglobulin production, compromised T-cell-independent immune responses and marked attenuation of the sustained calcium sign upon BCR stimulation.

A large body of evidence supports the role of B-cells and the humoral immune system in the pathogenesis of autoimmune and/or inflammatory diseases. Protein-based therapeutics (such as Rituxan) developed to deplete B-cells represent an approach to the treatment of a number of autoimmune and inflammatory diseases. Auto-antibodies and their resulting immune complexes are known to play pathogenic roles in autoimmune disease and/or inflammatory disease. The pathogenic response to these antibodies is dependent on signaling through Fc Receptors, which is, in turn, dependent upon Syk. Because of Syk's role in B-cell activation, as well as FcR dependent signaling, inhibitors of Syk can be useful as inhibitors of B-cell mediated pathogenic activity, including autoantibody production. Therefore, inhibition of Syk enzymatic activity in cells is proposed as a treatment for autoimmune disease through its effects on autoantibody production.

Syk also plays a key role in FCεRI mediated mast cell degranulation and eosinophil activation. Thus, Syk is implicated in allergic disorders including asthma. Syk binds to the phosphorylated gamma chain of FCεRI via its SH2 domains and is essential for downstream signaling. Syk deficient mast cells demonstrate defective degranulation, arachidonic acid and cytokine secretion. This also has been shown for pharmacologic agents that inhibit Syk activity in mast cells. Treatment with Syk antisense oligonucleotides inhibits antigen-induced infiltration of eosinophils and neutrophils in an animal model of asthma. Syk deficient eosinophils also show impaired activation in response to FCεRI stimulation. Therefore, small molecule inhibitors of Syk will be useful for treatment of allergy-induced inflammatory diseases including asthma.

Syk is also expressed in mast cells and monocytes and has been shown to be important for the function of these cells. For example, Syk deficiency in mice is associated with impaired IgE-mediated mast cell activation, which is marked diminution of TNF-alpha and other inflammatory cytokine release Syk kinase inhibitors have also been shown to inhibit mast cell degranulation in cell based assays. Additionally, a Syk inhibitors have been shown to inhibit antigen-induced passive cutaneous anaphylaxsis, bronchoconstriction and bronchial edema in rats.

Thus, the inhibition of Syk activity can be useful for the treatment of allergic disorders, autoimmune diseases and inflammatory diseases such as: SLE, rheumatoid arthritis, multiple vasculitides, idiopathic thrombocytopenic purpura (ITP), myasthenia gravis, allergic rhinitis, chronic obstructive pulmonary disease (COPD), adult respiratory distress syndrome (ARDs) and asthma. In addition, Syk has been reported to play an important role in ligand-independent tonic signaling through the B-cell receptor, known to be an important survival signal in B-cells. Thus, inhibition of Syk activity may be useful in treating certain types of cancer, including B-cell lymphoma and leukemia.

BRIEF SUMMARY

Provided is at least one chemical entity chosen from compounds of Formula I:

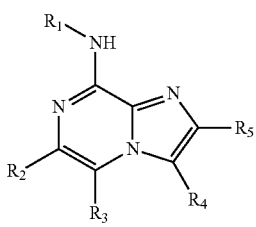

(I)

and pharmaceutically acceptable salts thereof, wherein
$R_1$ is pyridinyl, pyridazinyl, or pyrazolyl, each of which is optionally substituted, or
$R_1$ is

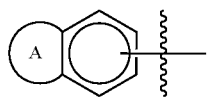

wherein A is an optionally substituted heteroaryl group having from 5 to 7 ring atoms including the atoms shared with the 6 membered aromatic ring;
$R_2$ is chosen from substituted aryl and optionally substituted heteroaryl;
$R_3$ is hydrogen;
$R_4$ is hydrogen; and
$R_5$ is hydrogen,
provided that
if $R_1$ is 2-methoxy-pyridin-5-yl, then $R_2$ is not 2,6-dimethylphenyl, 2-methoxyphenyl, 2-chlorophenyl, or 2-fluorophenyl;
if $R_1$ is indol-5-yl, then $R_2$ is not 2-chlorophenyl, furan-2-yl, or 3-chloro-4-fluorophenyl;
if $R_1$ is 1H-indazol-5-yl, 1H-indol-6-yl, benzo[d]oxazole-6-yl, benzo[d]isoxazole-6-yl, benzothiazol-6-yl, or 3H-benzoimidazol-5-yl, then $R_2$ is not 3-aminophenyl; and
if $R_1$ is 1H-indazol-6-yl, then $R_2$ is not 3-carboxyphenyl or 4-carboxyphenyl.

Also provided is a pharmaceutical composition, comprising at least one chemical entity described herein, together with at least one pharmaceutically acceptable vehicle chosen from carriers, adjuvants, and excipients.

Also provided is a method for treating a patient having a disease responsive to inhibition of Syk activity, comprising administering to the patient an effective amount of at least one chemical entity described herein.

Also provided is a method for treating a patient having a disease chosen from cancer, autoimmune diseases, inflammatory diseases, acute inflammatory reactions, and allergic disorders comprising administering to the patient an effective amount of at least one chemical entity described herein.

Also provided is a method for treating a patient having polycystic kidney disease comprising administering to the patient an effective amount of at least one chemical entity described herein.

Also provided is a method for increasing sensitivity of cancer cells to chemotherapy, comprising administering to a patient undergoing chemotherapy with a chemotherapeutic agent an amount of at least one chemical entity described herein, sufficient to increase the sensitivity of cancer cells to the chemotherapeutic agent.

Also provided is a method for inhibiting ATP hydrolysis, the method comprising contacting cells expressing Syk with at least one chemical entity described herein in an amount sufficient to detectably decrease the level of ATP hydrolysis in vitro.

Also provided is a method for determining the presence of Syk in a sample, comprising contacting the sample with at least one chemical entity described herein under conditions that permit detection of Syk activity, detecting a level of Syk activity in the sample, and therefrom determining the presence or absence of Syk in the sample.

Also provided is a method for inhibiting B-cell activity comprising contacting cells expressing Syk with at least one chemical entity described herein in an amount sufficient to detectably decrease B-cell activity in vitro.

DETAILED DESCRIPTION

As used herein, when any variable occurs more than one time in a chemical formula, its definition on each occurrence is independent of its definition at every other occurrence. In accordance with the usual meaning of "a" and "the" in patents, reference, for example, to "a" kinase or "the" kinase is inclusive of one or more kinases.

As used in the present specification, the following words, phrases and symbols are generally intended to have the meanings as set forth below, except to the extent that the context in which they are used indicates otherwise. The following abbreviations and terms have the indicated meanings throughout:

A dash ("-") that is not between two letters or symbols is used to indicate a point of attachment for a substituent. For example, —CONH$_2$ is attached through the carbon atom.

By "optional" or "optionally" is meant that the subsequently described event or circumstance may or may not occur, and that the description includes instances where the event or circumstance occurs and instances in which it does not.

For example, "optionally substituted alkyl" encompasses both "alkyl" and "substituted alkyl" as defined below. It will be understood by those skilled in the art, with respect to any group containing one or more substituents, that such groups are not intended to introduce any substitution or substitution patterns that are sterically impractical, synthetically non-feasible and/or inherently unstable.

"Alkyl" encompasses straight chain and branched chain having the indicated number of carbon atoms, usually from 1 to 20 carbon atoms, for example 1 to 8 carbon atoms, such as 1 to 6 carbon atoms. For example $C_1$-$C_6$ alkyl encompasses both straight and branched chain alkyl of from 1 to 6 carbon atoms. Examples of alkyl groups include methyl, ethyl, propyl, isopropyl, n-butyl, sec-butyl, tert-butyl, pentyl, 2-pentyl, isopentyl, neopentyl, hexyl, 2-hexyl, 3-hexyl, 3-methylpentyl, and the like. Alkylene is another subset of alkyl, referring to the same residues as alkyl, but having two points of attachment. Alkylene groups will usually have from 2 to 20 carbon atoms, for example 2 to 8 carbon atoms, such as from 2 to 6 carbon atoms. For example, $C_0$ alkylene indicates a covalent bond and $C_1$ alkylene is a methylene group. When an alkyl residue having a specific number of carbons is named, all geometric isomers having that number of carbons are intended to be encompassed; thus, for example, "butyl" is meant to include n-butyl, sec-butyl, isobutyl and t-butyl; "propyl" includes n-propyl and isopropyl. "Lower alkyl" refers to alkyl groups having 1 to 4 carbons.

"Alkenyl" indicates an unsaturated branched or straight-chain alkyl group having at least one carbon-carbon double bond derived by the removal of one molecule of hydrogen from adjacent carbon atoms of the parent alkyl. The group may be in either the cis or trans configuration about the double bond(s). Typical alkenyl groups include, but are not limited to, ethenyl; propenyls such as prop-1-en-1-yl, prop-1-en-2-yl, prop-2-en-1-yl (allyl), prop-2-en-2-yl; butenyls such as but-1-en-1-yl, but-1-en-2-yl, 2-methyl-prop-1-en-1-yl, but-2-en-1-yl, but-2-en-1-yl, but-2-en-2-yl, buta-1,3-dien-1-yl, buta-1,3-dien-2-yl; and the like. In some embodiments, an alkenyl group has from 2 to 20 carbon atoms and in other embodiments, from 2 to 6 carbon atoms.

"Cycloalkyl" indicates a saturated hydrocarbon ring group, having the specified number of carbon atoms, usually from 3 to 7 ring carbon atoms. Examples of cycloalkyl groups include cyclopropyl, cyclobutyl, cyclopentyl, and cyclohexyl as well as bridged and caged saturated ring groups such as norbornane.

By "alkoxy" is meant an alkyl group of the indicated number of carbon atoms attached through an oxygen bridge such as, for example, methoxy, ethoxy, propoxy, isopropoxy, n-butoxy, sec-butoxy, tert-butoxy, pentoxy, 2-pentyloxy, isopentoxy, neopentoxy, hexoxy, 2-hexoxy, 3-hexoxy, 3-methylpentoxy, and the like.

Alkoxy groups will usually have from 1 to 6 carbon atoms attached through the oxygen bridge. "Lower alkoxy" refers to alkoxy groups having 1 to 4 carbons.

"Aminocarbonyl" encompasses a group of the formula —(C=O)NR$_a$R$_b$ where R$_a$ and R$_b$ are independently chosen from hydrogen and the optional substituents for "substituted amino" described below.

"Acyl" refers to the groups (alkyl)-C(O)—; (cycloalkyl)-C(O)—; (aryl)-C(O)—; (heteroaryl)-C(O)—; and (heterocycloalkyl)-C(O)—, wherein the group is attached to the parent structure through the carbonyl functionality and wherein alkyl, cycloalkyl, aryl, heteroaryl, and heterocycloalkyl are as described herein. Acyl groups have the indicated number of carbon atoms, with the carbon of the keto group being included in the numbered carbon atoms. For example a $C_2$ acyl group is an acetyl group having the formula $CH_3(C=O)$—.

By "alkoxycarbonyl" is meant an ester group of the formula (alkoxy)(C=O)-attached through the carbonyl carbon wherein the alkoxy group has the indicated number of carbon atoms. Thus a $C_1$-$C_6$alkoxycarbonyl group is an alkoxy group having from 1 to 6 carbon atoms attached through its oxygen to a carbonyl linker.

By "amino" is meant the group —NH$_2$.

"Aryl" encompasses:
5- and 6-membered carbocyclic aromatic rings, for example, benzene; bicyclic ring systems wherein at least one ring is carbocyclic and aromatic, for
example, naphthalene, indane, and tetralin; and tricyclic ring systems wherein at least one ring is carbocyclic and aromatic, for example, fluorene.

For example, aryl includes 5- and 6-membered carbocyclic aromatic rings fused to a 5- to 7-membered heterocycloalkyl ring containing 1 or more heteroatoms chosen from N, O, and S. For such fused, bicyclic ring systems wherein only one of the rings is a carbocyclic aromatic ring, the point of attachment may be at the carbocyclic aromatic ring or the heterocycloalkyl ring. Bivalent radicals formed from substituted benzene derivatives and having the free valences at ring atoms are named as substituted phenylene radicals. Bivalent radicals derived from univalent polycyclic hydrocarbon radicals whose names end in "-yl" by removal of one hydrogen atom from the carbon atom with the free valence are named by adding "-idene" to the name of the corresponding univalent radical, e.g., a naphthyl group with two points of attachment is termed naphthylidene. Aryl, however, does not encompass or overlap in any way with heteroaryl, separately defined below. Hence, if one or more carbocyclic aromatic rings is fused with a heterocycloalkyl aromatic ring, the resulting ring system is heteroaryl, not aryl, as defined herein.

The term "aryloxy" refers to the group —O-aryl.

The term "halo" includes fluoro, chloro, bromo, and iodo, and the term "halogen" includes fluorine, chlorine, bromine, and iodine.

"Heteroaryl" encompasses:
5- to 7-membered aromatic, monocyclic rings containing one or more, for example, from 1 to 4, or In some embodiments, from 1 to 3, heteroatoms chosen from N, O, and S, with the remaining ring atoms being carbon; and
bicyclic heterocycloalkyl rings containing one or more, for example, from 1 to 4, or In some embodiments, from 1 to 3, heteroatoms chosen from N, O, and S, with the remaining ring atoms being carbon and wherein at least one heteroatom is present in an aromatic ring.

For example, heteroaryl includes a 5- to 7-membered heterocycloalkyl, aromatic ring fused to a 5- to 7-membered cycloalkyl ring. For such fused, bicyclic heteroaryl ring systems wherein only one of the rings contains one or more heteroatoms, the point of attachment may be at the heteroaromatic ring or the cycloalkyl ring. When the total number of S and O atoms in the heteroaryl group exceeds 1, those heteroatoms are not adjacent to one another. In some embodiments, the total number of S and O atoms in the heteroaryl group is not more than 2. In some embodiments, the total number of S and O atoms in the aromatic heterocycle is not more than 1. Examples of heteroaryl groups include, but are not limited to, (as numbered from the linkage position assigned priority 1), 2-pyridyl, 3-pyridyl, 4-pyridyl, 2,3-pyrazinyl, 3,4-pyrazinyl, 2,4-pyrimidinyl, 3,5-pyrimidinyl, 2,3-pyrazolinyl, 2,4-imidazolinyl, isoxazolinyl, oxazolinyl, thiazolinyl, thiadiazolinyl, tetrazolyl, thienyl, benzothiophenyl, furanyl, benzofuranyl, benzoimidazolinyl, indolinyl, pyridizinyl, triazolyl, quinolinyl, pyrazolyl, and 5,6,7,8-tetrahydroisoquinoline. Bivalent radicals derived from univalent heteroaryl radicals whose names end in "-yl" by removal of one hydrogen atom from the atom with the free valence are named by adding "-idene" to the name of the corresponding univalent radical, e.g., a pyridyl group with two points of attachment is a pyridylidene. Heteroaryl does not encompass or overlap with aryl as defined above.

Substituted heteroaryl also includes ring systems substituted with one or more oxide (—O—) substituents, such as pyridinyl N-oxides.

The term "heteroaryloxy" refers to the group —O-heteroaryl.

By "heterocycloalkyl" is meant a single aliphatic ring, usually with 3 to 7 ring atoms, containing at least 2 carbon atoms in addition to 1-3 heteroatoms independently selected from oxygen, sulfur, and nitrogen, as well as combinations comprising at least one of the foregoing heteroatoms. Suitable heterocycloalkyl groups include, for example (as numbered from the linkage position assigned priority 1), 2-pyrrolinyl, 2,4-imidazolidinyl, 2,3-pyrazolidinyl, 2-piperidyl, 3-piperidyl, 4-piperdyl, and 2,5-piperzinyl. Morpholinyl groups are also contemplated, including 2-morpholinyl and 3-morpholinyl (numbered wherein the oxygen is assigned priority 1). Substituted heterocycloalkyl also includes ring systems substituted with one or more oxo moieties, such as piperidinyl N-oxide, morpholinyl-N-oxide, 1-oxo-1-thiomorpholinyl and 1,1-dioxo-1-thiomorpholinyl.

The term "heterocycloalkyloxy" refers to the group —O-heterocylcoalkyl.

The term "nitro" refers to the group —NO$_2$.

The term "phosphono" refers to the group —PO$_3$H$_2$.

"Thiocarbonyl" refers to the group —C(=O)SH.

The term "optionally substituted thiocarbonyl" includes the following groups: —C(=O)S-(optionally substituted (C$_1$-C$_6$)alkyl), —C(=O)S-(optionally substituted aryl), —C(=O)S-(optionally substituted heteroaryl), and —C(=O)S-(optionally substituted heterocycloalkyl).

The term "sulfanyl" includes the groups: —S-(optionally substituted (C$_1$-C$_6$)alkyl), —S-(optionally substituted aryl), —S-(optionally substituted heteroaryl), and —S-(optionally substituted heterocycloalkyl). Hence, sulfanyl includes the group C$_1$-C$_6$ alkylsulfanyl.

The term "sulfinyl" includes the groups: —S(O)—H, —S(O)-(optionally substituted (C$_1$-C$_6$)alkyl), —S(O)-optionally substituted aryl), —S(O)-optionally substituted heteroaryl), —S(O)-(optionally substituted heterocycloalkyl); and —S(O)-(optionally substituted amino).

The term "sulfonyl" includes the groups: —S(O$_2$)—H, —S(O$_2$)-(optionally substituted (C$_1$-C$_6$)alkyl), —S(O$_2$)-optionally substituted aryl), —S(O$_2$)-optionally substituted heteroaryl), —S(O$_2$)-(optionally substituted heterocycloalkyl), —S(O$_2$)-(optionally substituted alkoxy), —S(O$_2$)-optionally substituted aryloxy), —S(O$_2$)-optionally substituted heteroaryloxy), —S(O$_2$)-(optionally substituted heterocyclyloxy); and —S(O$_2$)-(optionally substituted amino).

The term "substituted", as used herein, means that any one or more hydrogens on the designated atom or group is replaced with a selection from the indicated group, provided that the designated atom's normal valence is not exceeded. When a substituent is oxo (i.e., =O) then 2 hydrogens on the atom are replaced. Combinations of substituents and/or variables are permissible only if such combinations result in stable compounds or useful synthetic intermediates. A stable compound or stable structure is meant to imply a compound that is sufficiently robust to survive isolation from a reaction mixture, and subsequent formulation as an agent having at least practical utility. Unless otherwise specified, substituents are named into the core structure. For example, it is to be understood that when (cycloalkyl)alkyl is listed as a possible substituent, the point of attachment of this substituent to the core structure is in the alkyl portion.

The terms "substituted" alkyl, cycloalkyl, aryl, heterocycloalkyl, and heteroaryl (including without limitation pyridinyl, pyridazinyl, pyrazolyl, oxazolyl, pyrrolyl, thiazolyl, and imidazolyl group), unless otherwise expressly defined, refer respectively to alkyl, cycloalkyl, aryl, heterocycloalkyl, and heteroaryl (including without limitation pyridinyl, pyridazinyl, pyrazolyl, oxazolyl, pyrrolyl, thiazolyl, and imidazolyl group) wherein one or more (such as up to 5, for example, up to 3) hydrogen atoms are replaced by a substituent independently chosen from:

—R$^a$, —OR$^b$, —O(C$_1$-C$_2$ alkyl)O— (e.g., methylenedioxy-), —SR$^b$, guanidine, guanidine wherein one or more of the guanidine hydrogens are replaced with a lower-alkyl group, —NR$^b$R$^c$, halo, cyano, oxo (as a substituent for heterocycloalkyl), nitro, —COR$^b$, —CO$_2$R$^b$, —CONR$^b$R$^c$, —OCOR$^b$, —OCO$_2$R$^a$, —OCONR$^b$R$^c$, —NR$^c$COR$^b$, —NR$^c$O$_2$R$^a$, —NR$^c$CONR$^b$R$^c$, —SOR$^a$, —SO$_2$R$^a$, —SO$_2$NR$^b$R$^c$, and —NR$^c$SO$_2$R$^a$, where R$^a$ is chosen from optionally substituted C$_1$-C$_6$ alkyl, optionally substituted cycloalkyl, optionally substituted aryl, optionally substituted heterocycloalkyl, and optionally substituted heteroaryl;

R$^b$ is chosen from H, optionally substituted C$_1$-C$_6$ alkyl, optionally substituted aryl, and optionally substituted heteroaryl; and R$^c$ is chosen from hydrogen and optionally substituted C$_1$-C$_4$ alkyl; or R$^b$ and R$^c$, and the nitrogen to which they are attached, form an optionally substituted heterocycloalkyl group; and where each optionally substituted group is unsubstituted or independently substituted with one or more, such as one, two, or three, substituents independently selected from C$_1$-C$_4$ alkyl, C$_3$-C$_6$ cycloalkyl, aryl, heteroaryl, aryl-C$_1$-C$_4$ alkyl-, heteroaryl-C$_1$-C$_4$ alkyl-, C$_1$-C$_4$ haloalkyl-, —OC$_1$-C$_4$ alkyl, —OC$_1$-C$_4$ alkylphenyl, —C$_1$-C$_4$ alkyl-OH, —C$_1$-C$_4$ alkyl-O—C$_1$-C$_4$ alkyl, —OC$_1$-C$_4$ haloalkyl, halo, —OH, —NH$_2$, —C$_1$-C$_4$ alkyl-NH$_2$, —N(C$_1$-C$_4$ alkyl)(C$_1$-C$_4$ alkyl), —NH(C$_1$-C$_4$ alkyl), —N(C$_1$-C$_4$ alkyl)(C$_1$-C$_4$ alkylphenyl), —NH(C$_1$-C$_4$ alkylphenyl), cyano, nitro, oxo (as a substitutent for heteroaryl), —CO$_2$H, —C(O)OC$_1$-C$_4$ alkyl, —CON(C$_1$-C$_4$ alkyl)(C$_1$-C$_4$ alkyl), —CONH(C$_1$-C$_4$ alkyl), —CONH$_2$, —NHC(O)(C$_1$-C$_4$ alkyl), —NHC(O)(phenyl), —N(C$_1$-C$_4$ alkyl)C(O)(C$_1$-C$_4$ alkyl), —N(C$_1$-C$_4$ alkyl)C(O)(phenyl), —C(O)C$_1$-C$_4$ alkyl, —C(O)C$_1$-C$_4$ phenyl, —C(O)C$_1$-C$_4$ haloalkyl, —OC(O)C$_1$-C$_4$ alkyl, —SO$_2$(C$_1$-C$_4$ alkyl), —SO$_2$(phenyl), —SO$_2$(C$_1$-C$_4$ haloalkyl), —SO$_2$NH$_2$, —SO$_2$NH(C$_1$-C$_4$ alkyl), —SO$_2$NH(phenyl), —NHSO$_2$(C$_1$-C$_4$ alkyl), —NHSO$_2$(phenyl), and —NHSO$_2$(C$_1$-C$_4$ haloalkyl).

The term "substituted acyl" refers to the groups (substituted alkyl)-C(O)—; (substituted cycloalkyl)-C(O)—; (substituted aryl)-C(O)—; (substituted heteroaryl)-C(O)—; and (substituted heterocycloalkyl)-C(O)—, wherein the group is attached to the parent structure through the carbonyl functionality and wherein substituted alkyl, cycloalkyl, aryl, heteroaryl, and heterocycloalkyl are as described herein.

The term "substituted alkoxy" refers to alkoxy wherein the alkyl constituent is substituted (i.e., —O-(substituted alkyl)) wherein "substituted alkyl" is as described herein.

The term "substituted alkoxycarbonyl" refers to the group (substituted alkyl)-O—C(O)— wherein the group is attached to the parent structure through the carbonyl functionality and wherein substituted alkyl is as described herein.

The term "substituted aryloxy" refers to aryloxy wherein the aryl constituent is substituted (i.e., —O-(substituted aryl)) wherein "substituted aryl" is as described herein.

The term "substituted heteroaryloxy" refers to heteroaryloxy wherein the aryl constituent is substituted (i.e., —O-(substituted heteroaryl)) wherein "substituted heteroaryl" is as described herein.

The term "substituted cycloalkyloxy" refers to cycloalkyloxy wherein the cycloalkyl constituent is substituted (i.e., —O-(substituted cycloalkyl)) wherein "substituted cycloalkyl" is as described herein.

The term "substituted heterocycloalkyloxy" refers to heterocycloalkyloxy wherein the alkyl constituent is substituted (i.e., —O-(substituted heterocycloalkyl)) wherein "substituted heterocycloalkyl" is as described herein.

The term "substituted amino" refers to the group —NHR$^d$ or —NR$^d$R$^d$ where each R$^d$ is independently chosen from: hydroxy, optionally substituted alkyl, optionally substituted cycloalkyl, optionally substituted acyl, aminocarbonyl, optionally substituted aryl, optionally substituted heteroaryl, optionally substituted heterocycloalkyl, alkoxycarbonyl, sulfinyl and sulfonyl, each as described herein, and provided that only one R$^d$ may be hydroxyl. The term "substituted amino" also refers to N-oxides of the groups —NHR$^d$, and NR$^d$R$^d$ each as described above. N-oxides can be prepared by treatment of the corresponding amino group with, for example, hydrogen peroxide or m-chloroperoxybenzoic acid. The person skilled in the art is familiar with reaction conditions for carrying out the N-oxidation.

Compounds described herein include, but are not limited to, their optical isomers, racemates, and other mixtures thereof. In those situations, the single enantiomers or diastereomers, i.e., optically active forms, can be obtained by asymmetric synthesis or by resolution of the racemates. Resolution of the racemates can be accomplished, for example, by conventional methods such as crystallization in the presence of a resolving agent, or chromatography, using, for example a chiral high-pressure liquid chromatography (HPLC) column. In addition, such compounds include Z- and E-forms (or cis- and trans-forms) of compounds with carbon-carbon double bonds. Where compounds described herein exist in various tautomeric forms, chemical entities include all tautomeric forms of the compound. Such compounds also include crystal forms including polymorphs and clathrates.

Compounds of Formula I also include crystalline and amorphous forms of those compounds, including, for example, polymorphs, pseudopolymorphs, solvates, hydrates, unsolvated polymorphs (including anhydrates), conformational polymorphs, and amorphous forms of the compounds, as well as mixtures thereof. "Crystalline form," "polymorph," and "novel form" may be used interchangeably herein, and are meant to include all crystalline and amorphous forms of the compound, including, for example, polymorphs, pseudopolymorphs, solvates, hydrates, unsolvated polymorphs (including anhydrates), conformational polymorphs, and amorphous forms, as well as mixtures thereof, unless a particular crystalline or amorphous form is referred to. Compounds of Formula I also include pharmaceutically acceptable forms of the recited compounds, including chelates, non-covalent complexes, prodrugs, and mixtures thereof.

Compounds of Formula I also include different enriched isotopic forms, e.g., compounds enriched in the content of $^2$H, $^3$H, $^{11}$C, $^{13}$C and/or $^{14}$C. In some embodiments, the compounds are deuterated. Such deuterated forms can be made by the procedure described in U.S. Pat. Nos. 5,846,514 and 6,334,997. As described in U.S. Pat. Nos. 5,846,514 and 6,334,997, deuteration may improve the efficacy and increase the duration of action of drugs.

Deuterium substituted compounds can be synthesized using various methods such as described in: Dean, Dennis C.; Editor. Recent Advances in the Synthesis and Applications of Radiolabeled Compounds for Drug Discovery and Development. [In: Curr., Pharm. Des., 2000; 6(10)] 2000, 110 pp. CAN 133:68895 AN 2000:473538 CAPLUS; Kabalka, George W.; Varma, Rajender S. The Synthesis of Radiolabeled Compounds via Organometallic Intermediates, Tetrahedron, 1989, 45(21), 6601-21, CODEN: TETRAB ISSN:0040-4020. CAN 112:20527 AN 1990:20527 CAPLUS; and Evans, E. Anthony. Synthesis of radiolabeled compounds, J. Radioanal. Chem., 1981, 64(1-2), 9-32. CODEN: JRACBN ISSN:0022-4081, CAN 95:76229 AN 1981:476229 CAPLUS.

Chemical entities include, but are not limited to compounds described herein and all pharmaceutically acceptable forms thereof. Hence, the terms "chemical entity" and "chemical entities" also encompass pharmaceutically acceptable salts.

"Pharmaceutically acceptable salts" include, but are not limited to salts with inorganic acids, such as hydrochlorate, phosphate, diphosphate, hydrobromate, sulfate, sulfinate, nitrate, and like salts; as well as salts with an organic acid, such as malate, maleate, fumarate, tartrate, succinate, citrate, acetate, lactate, methanesulfonate, p-toluenesulfonate, 2-hydroxyethylsulfonate, benzoate, salicylate, stearate, and alkanoate such as acetate, HOOC—(CH$_2$)$_n$—COOH where n is 0-4, and like salts. Similarly, pharmaceutically acceptable cations include, but are not limited to sodium, potassium, calcium, aluminum, lithium, and ammonium.

In addition, if the compounds described herein are obtained as an acid addition salt, the free base can be obtained by basifying a solution of the acid salt. Conversely, if the product is a free base, an addition salt, particularly a pharmaceutically acceptable addition salt, may be produced by dissolving the free base in a suitable organic solvent and treating the solution with an acid, in accordance with conventional procedures for preparing acid addition salts from base compounds. Those skilled in the art will recognize various synthetic methodologies that may be used to prepare non-toxic pharmaceutically acceptable addition salts.

As noted above, prodrugs also fall within the scope of compounds of Formula I. In some embodiments, the "prodrugs" described herein include any compound that becomes a compound of Formula I when administered to a patient, e.g., upon metabolic processing of the prodrug. Examples of prodrugs include derivatives of functional groups, such as a carboxylic acid group, in the compounds of Formula I. Exemplary prodrugs of a carboxylic acid group include, but are not limited to, carboxylic acid esters such as alkyl esters, hydroxyalkyl esters, arylalkyl esters, and aryloxyalkyl esters.

A "solvate" is formed by the interaction of a solvent and a compound. The term "compound" is intended to include solvates of compounds. Similarly, "salts" includes solvates of salts. Suitable solvates are pharmaceutically acceptable solvates, such as hydrates, including monohydrates and hemi-hydrates.

A "chelate" is formed by the coordination of a compound to a metal ion at two (or more) points. The term "compound" is intended to include chelates of compounds. Similarly, "salts" includes chelates of salts.

A "non-covalent complex" is formed by the interaction of a compound and another molecule wherein a covalent bond is not formed between the compound and the molecule. For example, complexation can occur through van der Waals interactions, hydrogen bonding, and electrostatic interactions (also called ionic bonding). Such non-covalent complexes are included in the term "compound".

The term "hydrogen bond" refers to a form of association between an electronegative atom (also known as a hydrogen bond acceptor) and a hydrogen atom attached to a second, relatively electronegative atom (also known as a hydrogen bond donor). Suitable hydrogen bond donor and acceptors are well understood in medicinal chemistry (G. C. Pimentel and A. L. McClellan, The Hydrogen Bond, Freeman, San Francisco, 1960; R. Taylor and O. Kennard, "Hydrogen Bond Geometry in Organic Crystals", Accounts of Chemical Research, 17, pp. 320-326 (1984)).

"Hydrogen bond acceptor" refers to a group comprising an oxygen or nitrogen, especially an oxygen or nitrogen that is sp$^2$-hybridized, an ether oxygen, or the oxygen of a sulfoxide or N-oxide.

The term "hydrogen bond donor" refers to an oxygen, nitrogen, or heteroaromatic carbon that bears a hydrogen-.group containing a ring nitrogen or a heteroaryl group containing a ring nitrogen.

As used herein the terms "group", "radical" or "fragment" are synonymous and are intended to indicate functional groups or fragments of molecules attachable to a bond or other fragments of molecules.

The term "active agent" is used to indicate a chemical entity which has biological activity. In some embodiments, an "active agent" is a compound having pharmaceutical utility. For example an active agent may be an anti-cancer therapeutic.

The term "therapeutically effective amount" of a chemical entity described herein means an amount effective, when administered to a human or non-human patient, to provide a therapeutic benefit such as amelioration of symptoms, slowing of disease progression, or prevention of disease e.g., a therapeutically effective amount may be an amount sufficient to decrease the symptoms of a disease responsive to inhibition of Syk activity. In some embodiments, a therapeutically effective amount is an amount sufficient to reduce cancer symptoms, the symptoms of an allergic disorder, the symptoms of an autoimmune and/or inflammatory disease, or the symptoms of an acute inflammatory reaction. In some embodiments a therapeutically effective amount is an amount sufficient to decrease the number of detectable cancerous cells in an organism, detectably slow, or stop the growth of a cancerous tumor. In some embodiments, a therapeutically effective amount is an amount sufficient to shrink a cancerous tumor. In some embodiments, a patient suffering from cancer may not present symptoms of being affected. In some embodiments, a therapeutically effective amount of a chemical entity is an amount sufficient to prevent a significant increase or significantly reduce the detectable level of cancerous cells or cancer markers in the patient's blood, serum, or tissues. In some embodiments, a therapeutically effective amount may also be an amount sufficient, when administered to a patient, to detectably slow progression of the disease, or prevent the patient to whom the chemical entity is given from presenting symptoms of the allergic disorders and/or autoimmune and/or inflammatory disease, and/or acute inflammatory response. In some embodiments, a therapeutically effective amount may also be an amount sufficient to produce a detectable decrease in the amount of a marker protein or cell type in the patient's blood or serum. In some embodiments a therapeutically effective amount is an amount of a chemical entity described herein sufficient to significantly decrease the activity of B-cells. In some embodiments, a therapeutically effective amount is an amount of a chemical entity described herein sufficient to significantly decrease the number of B-cells. In some embodiments, a therapeutically effective amount is an amount of a chemical entity described herein sufficient to decrease the level of anti-acetylcholine receptor antibody in a patient's blood with the disease myasthenia gravis.

The term "inhibition" indicates a significant decrease in the baseline activity of a biological activity or process. "Inhibition of Syk activity" refers to a decrease in Syk activity as a direct or indirect response to the presence of at least one chemical entity described herein, relative to the activity of Syk in the absence of the at least one chemical entity. The decrease in activity may be due to the direct interaction of the compound with Syk, or due to the interaction of the chemical entity(ies) described herein with one or more other factors that in turn affect Syk activity. For example, the presence of the chemical entity(ies) may decrease Syk activity by directly binding to the Syk, by causing (directly or indirectly) another factor to decrease Syk activity, or by (directly or indirectly) decreasing the amount of Syk present in the cell or organism.

Inhibition of Syk activity also refers to observable inhibition of Syk activity in a standard biochemical assay for Syk activity, such as the ATP hydrolysis assay described below. In some embodiments, the chemical entity described herein has an $IC_{50}$ value less than or equal to 1 micromolar. In some embodiments, the chemical entity has an $IC_{50}$ value less than or equal to less than 100 nanomolar. In some embodiments, the chemical entity has an $IC_{50}$ value less than or equal to 10 nanomolar.

"Inhibition of B-cell activity" refers to a decrease in B-cell activity as a direct or indirect response to the presence of at least one chemical entity described herein, relative to the activity of B-cells in the absence of the at least one chemical entity. The decrease in activity may be due to the direct interaction of the compound with Syk or with one or more other factors that in turn affect B-cell activity.

Inhibition of B-cell activity also refers to observable inhibition of CD86 expression in a standard assay such as the assay described below. In some embodiments, the chemical entity described herein has an $IC_{50}$ value less than or equal to 10 micromolar. In some embodiments, the chemical entity has an $IC_{50}$ value less than or equal to less than 1 micromolar. In some embodiments, the chemical entity has an $IC_{50}$ value less than or equal to 500 nanomolar.

"B cell activity" also includes activation, redistribution, reorganization, or capping of one or more various B cell membrane receptors, or membrane-bound immunoglobulins, e.g, IgM, IgG, and IgD. Most B cells also have membrane receptors for Fc portion of IgG in the form of either antigen-antibody complexes or aggregated IgG. B cells also carry membrane receptors for the activated components of complement, e.g., C3b, C3d, C4, and C1q. These various membrane receptors and membrane-bound immunoglobulins have membrane mobility and can undergo redistribution and capping that can initiate signal transduction.

B cell activity also includes the synthesis or production of antibodies or immunoglobulins. Immunoglobulins are synthesized by the B cell series and have common structural features and structural units. Five immunoglobulin classes, i.e., IgG, IgA, IgM, IgD, and IgE, are recognized on the basis of structural differences of their heavy chains including the amino acid sequence and length of the polypeptide chain. Antibodies to a given antigen may be detected in all or several classes of immunoglobulins or may be restricted to a single class or subclass of immunoglobulin. Autoantibodies or autoimmune antibodies may likewise belong to one or several classes of immunoglobulins. For example, rheumatoid factors (antibodies to IgG) are most often recognized as an IgM immunoglobulin, but can also consist of IgG or IgA.

In addition, B cell activity also is intended to include a series of events leading to B cell clonal expansion (proliferation) from precursor B lymphocytes and differentiation into antibody-synthesizing plasma cells which takes place in conjunction with antigen-binding and with cytokine signals from other cells.

"Inhibition of B-cell proliferation" refers to inhibition of proliferation of abnormal B-cells, such as cancerous B-cells, e.g. lymphoma B-cells and/or inhibition of normal, non-diseased B-cells. The term "inhibition of B-cell proliferation" indicates any significant decrease in the number of B-cells, either in vitro or in vivo. Thus an inhibition of B-cell proliferation in vitro would be any significant decrease in the number of B-cells in an in vitro sample contacted with at least one chemical entity described herein as compared to a matched sample not contacted with the chemical entity(ies).

Inhibition of B-cell proliferation also refers to observable inhibition of B-cell proliferation in a standard thymidine incorporation assay for B-cell proliferation, such as the assay described herein. In some embodiments, the chemical entity has an $IC_{50}$ value less than or equal to 10 micromolar. In some embodiments, the chemical entity has an $IC_{50}$ value less than or equal to less than 1 micromolar. In some embodiments, the chemical entity has an $IC_{50}$ value less than or equal to 500 nanomolar.

An "allergy" or "allergic disorder" refers to acquired hypersensitivity to a substance (allergen). Allergic conditions include eczema, allergic rhinitis or coryza, hay fever, bronchial asthma, urticaria (hives) and food allergies, and other atopic conditions.

"Asthma" refers to a disorder of the respiratory system characterized by inflammation, narrowing of the airways and increased reactivity of the airways to inhaled agents. Asthma is frequently, although not exclusively associated with atopic or allergic symptoms.

By "significant" is meant any detectable change that is statistically significant in a standard parametric test of statistical significance such as Student's T-test, where $p<0.05$.

A "disease responsive to inhibition of Syk activity" is a disease in which inhibiting Syk kinase provides a therapeutic benefit such as an amelioration of symptoms, decrease in disease progression, prevention or delay of disease onset, or inhibition of aberrant activity of certain cell-types (monocytes, B-cells, and mast cells).

"Treatment or treating means any treatment of a disease in a patient, including:
a) preventing the disease, that is, causing the clinical symptoms of the disease not to develop;
b) inhibiting the disease;
c) slowing or arresting the development of clinical symptoms; and/or
d) relieving the disease, that is, causing the regression of clinical symptoms.

"Patient" refers to an animal, such as a mammal, that has been or will be the object of treatment, observation or experiment. The methods described herein may be useful in both human therapy and veterinary applications. In some embodiments, the patient is a mammal; in some embodiments the patient is human; and in some embodiments the patient is chosen from cats and dogs.

Provided is at least one chemical entity chosen from compounds of Formula I:

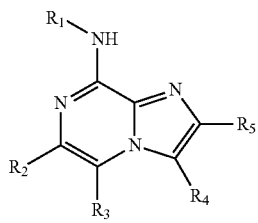

(I)

and pharmaceutically acceptable salts thereof, wherein
$R_1$ is pyridinyl, pyridazinyl, or pyrazolyl, each of which is optionally substituted, or $R_1$ is

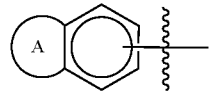

wherein A is an optionally substituted heteroaryl group having from 5 to 7 ring atoms including the atoms shared with the 6 membered aromatic ring;
$R_2$ is chosen from substituted aryl and optionally substituted heteroaryl;
$R_3$ is hydrogen;
$R_4$ is hydrogen; and
$R_5$ is hydrogen,
provided that
if $R_1$ is 2-methoxy-pyridin-5-yl, then $R_2$ is not 2,6-dimethylphenyl, 2-methoxyphenyl, 2-chlorophenyl, or 2-fluorophenyl;
if $R_1$ is indol-5-yl, then $R_2$ 2-chlorophenyl, furan-2-yl, or 3-chloro-4-fluorophenyl;
if $R_1$ is 1H-indazol-5-yl, 1H-indol-6-yl, benzo[d]oxazole-6-yl, benzo[d]isoxazole-6-yl, benzothiazol-6-yl, or 3H-benzoimidazol-5-yl, then $R_2$ is not 3-aminophenyl; and
if $R_1$ is 1H-indazol-6-yl, then $R_2$ is not 3-carboxyphenyl or 4-carboxyphenyl.

In some embodiments, $R_1$ is pyridinyl substituted with one or more groups chosen from hydroxy;
—$NR^bR^c$ wherein $R^b$ is chosen from hydrogen and $C_1$-$C_6$ alkyl optionally substituted with one or two groups chosen from hydroxy and —$OC_1$-$C_4$ alkyl and $R^c$ is independently chosen from hydrogen and $C_1$-$C_4$ alkyl optionally substituted with one or two groups chosen from hydroxy and —$OC_1$-$C_4$ alkyl;
heterocycloalkyl optionally substituted with one or two groups chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl;
—$OC_1$-$C_6$ alkyl optionally substituted with one or two groups chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl;
$C_1$-$C_6$ alkyl optionally substituted with one or two groups chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl; and
pyrazolyl optionally substituted with one or two groups chosen from hydroxy, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl.

In some embodiments, $R_1$ is pyridinyl substituted with one or more groups chosen from:
hydroxy;
—$NR^bR^c$ wherein $R^b$ is chosen from hydrogen and $C_1$-$C_6$ alkyl optionally substituted with one or two groups chosen from hydroxy and —$OC_1$-$C_4$ alkyl and $R^c$ is independently chosen from hydrogen and $C_1$-$C_4$ alkyl optionally substituted with one or two groups chosen from hydroxy and —$OC_1$-$C_4$ alkyl;
heterocycloalkyl optionally substituted with one or two groups chosen from hydroxy, —$OC_1$-$C_4$ alkyl, and $C_1$-$C_4$ alkyl;

—OC₁-C₆ alkyl optionally substituted with one or two groups chosen from hydroxy, —OC₁-C₄ alkyl, —NH₂, —N(C₁-C₄ alkyl)H, and —N(C₁-C₄ alkyl)(C₁-C₄ alkyl); and C₁-C₆ alkyl optionally substituted with hydroxy.

In some embodiments, R₁ is chosen from (2-methyl-2-hydroxypropoxy)pyridin-6-yl, (2-methoxyethoxy)pyridinyl, 2-(dimethylamino)ethoxy-3-pyridinyl, hydroxyethoxy-5-pyridinyl, (3-methyl-3-hydroxyazetidine)pyridin-3-yl, (3-methyl-3-hydroxyazetidine)pyridin-2-yl, (3-hydroxyazetidine)pyridin-2-yl, (hydroxy(dimethylethyl))-5-pyridinyl, (4-methyl-4-hydroxypiperidine)pyridin-2-yl, (3-methyl-3-hydroxypiperidine)pyridin-2-yl, 5-morpholinopyridin-2-yl, 6-morpholinopyridin-3-yl, ((2-methoxyethyl)(methyl)amino)pyridin-5-yl, ((2-hydroxyethyl)(methyl)amino)pyridin-5-yl, 2-methoxy-4-pyridinyl, and 2-hydroxy-5-pyridinyl.

In some embodiments, R₁ is pyrazolyl substituted with one or two groups chosen from cycloalkyl, C₁-C₆ alkyl, and C₁-C₆ alkyl substituted with one or more groups chosen from hydroxy and —OC₁-C₄ alkyl.

In some embodiments, R₁ is chosen from (2-hydroxyethyl)-1H-pyrazol-4-yl, (2-hydroxypropyl)-1H-pyrazol-4-yl, (2-methoxyethyl)-1H-pyrazol-4-yl, 1-ethyl-1H-pyrazol-4-yl, 1-isopropyl-1H-pyrazol-4-yl, 3-cyclopropyl-1H-pyrazol-5-yl, and 1-ethyl-5-methyl-1H-pyrazol-3-yl.

In some embodiments, R₁ is

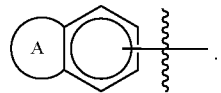

In some embodiments, A is an optionally substituted pyrazolyl, oxazolyl, pyrrolyl, thiazolyl, or imidazolyl group. In some embodiments, the imidazolyl group is substituted with C₁-C₆ alkyl.

In some embodiments, R₁ is chosen from 1H-benzo[d]imidazol-6-yl, 1H-benzo[d]imidazol-5-yl, 1H-indazol-6-yl, 1H-indazol-5-yl, 1-methyl-1H-benzo[d]imidazol-6-yl, benzoxazol-6-yl, benzoxazol-5-yl, imidazo[1,2-a]pyridine-6-yl, 1H-indole-6-yl, 1H-indole-5-yl, benzothiazol-6-yl, and benzothiazol-5-yl.

In some embodiments, R₂ is chosen from optionally substituted heteroaryl, dihydroindolyl optionally substituted with oxo and C₁-C₆ alkyl, and dihydrobenzoxazinyl optionally substituted with oxo.

In some embodiments, R₂ is chosen from 2,3-dimethyl-2H-indazol-6-yl, 1H-indazolyl-6-yl, 1-methyl-1H-indazol-5-yl, 1-methyl-1H-indazol-6-yl, 3,4-dihydro-2H-1,4-benzoxazin-3-one-6-yl, 1,3-benzoxazol-6-yl, 3-aminoquinolin-6-yl, 2,3-dihydro-1H-indol-6-yl, 1H,2H,3H-pyrido[2,3-b][1,4]oxazin-2-one, benzothiazolyl, 2-aminoquinazolin-6-yl, 3,3-dimethylindolin-2-one, 2,3-dihydro-1H-indol-2-one, 4-fluoro-1H-indazol-6-yl, 5-fluoro-1H-indazol-6-yl, and 3-amino-1H-indazol-6-yl.

In some embodiments, R₂ is chosen from 1H-indazolyl-6-yl, 1-methyl-1H-indazol-5-yl, 1-methyl-1H-indazol-6-yl, 3,4-dihydro-2H-1,4-benzoxazin-3-one-6-yl, 1,3-benzoxazol-6-yl, 3-aminoquinolin-6-yl, and 2,3-dihydro-1H-indol-2-one-6-yl.

Also provided is at least one chemical entity chosen from:
N-[6-(1H-indazol-6-yl)imidazo[1,2-a]pyrazin-8-yl]-1H-1,3-benzodiazol-6-amine;
N-[6-(1H-indazol-6-yl)imidazo[1,2-a]pyrazin-8-yl]-1H-indazol-6-amine;
N-[6-(1H-indazol-6-yl)imidazo[1,2-a]pyrazin-8-yl]-1-methyl-1H-1,3-benzodiazol-6-amine;
N-[6-(1H-indazol-6-yl)imidazo[1,2-a]pyrazin-8-yl]-1,3-benzoxazol-6-amine;
N-[6-(1H-indazol-6-yl)imidazo[1,2-a]pyrazin-8-yl]-1,3-benzoxazol-5-amine;
5-{[6-(1H-indazol-6-yl)imidazo[1,2-a]pyrazin-8-yl]amino}pyridin-2-ol;
N-{imidazo[1,2-a]pyridin-6-yl}-6-(1H-indazol-6-yl)imidazo[1,2-a]pyrazin-8-amine;
N-[6-(1H-indazol-6-yl)imidazo[1,2-a]pyrazin-8-yl]-1H-indazol-5-amine;
N-[6-(1H-indazol-6-yl)imidazo[1,2-a]pyrazin-8-yl]-1H-indol-6-amine;
N-[6-(1H-indazol-6-yl)imidazo[1,2-a]pyrazin-8-yl]-1H-indol-5-amine;
N-[6-(1H-indazol-6-yl)imidazo[1,2-a]pyrazin-8-yl]-1,3-benzothiazol-6-amine;
N-[6-(1H-indazol-6-yl)imidazo[1,2-a]pyrazin-8-yl]-1,3-benzothiazol-5-amine;
N-[6-(1H-indazol-6-yl)imidazo[1,2-a]pyrazin-8-yl]-2-methoxypyridin-4-amine;
6-[8-(1H-1,3-benzodiazol-5-ylamino)imidazo[1,2-a]pyrazin-6-yl]-3,4-dihydro-2H-1,4-benzoxazin-3-one;
2-(4-{[6-(1H-indazol-6-yl)imidazo[1,2-a]pyrazin-8-yl]amino}-1H-pyrazol-1-yl)ethan-1-ol;
3-(4-{[6-(1H-indazol-6-yl)imidazo[1,2-a]pyrazin-8-yl]amino}-1H-pyrazol-1-yl)propan-1-ol;
N-[6-(1H-indazol-6-yl)imidazo[1,2-a]pyrazin-8-yl]-1-(2-methoxyethyl)-1H-pyrazol-4-amine;
1-ethyl-N-[6-(1H-indazol-6-yl)imidazo[1,2-a]pyrazin-8-yl]-1H-pyrazol-4-amine;
N-[6-(1,3-benzoxazol-6-yl)imidazo[1,2-a]pyrazin-8-yl]-1H-1,3-benzodiazol-6-amine;
N-[6-(1H-1,3-benzodiazol-6-yl)imidazo[1,2-a]pyrazin-8-yl]-1H-indazol-6-amine;
N-[6-(1-methyl-1H-indazol-5-yl)imidazo[1,2-a]pyrazin-8-yl]-1H-indazol-5-amine;
N-[6-(3,4-dihydro-2H-1,4-benzoxazin-6-yl)imidazo[1,2-a]pyrazin-8-yl]-1H-indazol-6-amine;
N-[6-(3-aminoquinolin-6-yl)imidazo[1,2-a]pyrazin-8-yl]-1,3-benzothiazol-5-amine;
6-{8-[(2-methoxypyridin-4-yl)amino]imidazo[1,2-a]pyrazin-6-yl}-3,4-dihydro-2H-1,4-benzoxazin-3-one;
N-[6-(2,3-dihydro-1H-indol-6-yl)imidazo[1,2-a]pyrazin-8-yl]-2-methoxypyridin-4-amine;
N-[6-(1H-indazol-6-yl)imidazo[1,2-a]pyrazin-8-yl]-1-(propan-2-yl)-1H-pyrazol-4-amine;
1-methyl-N-[6-(1-methyl-1H-indazol-6-yl)imidazo[1,2-a]pyrazin-8-yl]-1H-1,3-benzodiazol-6-amine;
3-cyclopropyl-N-[6-(1H-indazol-6-yl)imidazo[1,2-a]pyrazin-8-yl]-1H-pyrazol-5-amine;
N-[6-(1H-indazol-6-yl)imidazo[1,2-a]pyrazin-8-yl]-6-(morpholin-4-yl)pyridin-3-amine;
N-[6-(2,3-dimethyl-2H-indazol-6-yl)imidazo[1,2-a]pyrazin-8-yl]-6-(morpholin-4-yl)pyridin-3-amine;
5-N-[6-(1H-indazol-6-yl)imidazo[1,2-a]pyrazin-8-yl]-2-N-(2-methoxyethyl)-2-N-methylpyridine-2,5-diamine;
2-[(5-{[6-(1H-indazol-6-yl)imidazo[1,2-a]pyrazin-8-yl]amino}pyridin-2-yl)(methyl)amino]ethan-1-ol;
1-[(6-{[6-(1H-indazol-6-yl)imidazo[1,2-a]pyridin-8-yl]amino}pyridin-3-yl)oxy]-2-methylpropan-2-ol;
7-(8-{[1-(2-hydroxyethyl)-1H-pyrazol-4-yl]amino}imidazo[1,2-a]pyrazin-6-yl)-1H,2H,3H-pyrido[2,3-b][1,4]oxazin-2-one;
2-(4-{[6-(3,4-dihydro-2H-1,4-benzoxazin-7-yl)imidazo[1,2-a]pyrazin-8-yl]amino}-1H-pyrazol-1-yl)ethan-1-ol;

6-(8-{[1-(2-hydroxyethyl)-1H-pyrazol-4-yl]amino}imidazo[1,2-a]pyrazin-6-yl)-3,4-dihydro-2H-1,4-benzoxazin-3-one;
2-(4-{[6-(1,3-benzothiazol-5-yl)imidazo[1,2-a]pyrazin-8-yl]amino}-1H-pyrazol-1-yl)ethan-1-ol;
N-[6-(1H-indazol-6-yl)imidazo[1,2-a]pyrazin-8-yl]-6-(2-methoxyethoxy)pyridin-3-amine;
6-(8-{[6-(morpholin-4-yl)pyridin-3-yl]amino}imidazo[1,2-a]pyrazin-6-yl)quinazolin-2-amine;
2-(4-{[6-(3,4-dihydro-2H-1,4-benzoxazin-6-yl)imidazo[1,2-a]pyrazin-8-yl]amino}-1H-pyrazol-1-yl)ethan-1-ol;
6-[2-(dimethylamino)ethoxy]-N-[6-(1H-indazol-6-yl)imidazo[1,2-a]pyrazin-8-yl]pyridin-3-amine;
1-(6-{[6-(1H-indazol-6-yl)imidazo[1,2-a]pyrazin-8-yl]amino}pyridin-3-yl)-3-methylazetidin-3-ol;
2-[(5-{[6-(1H-indazol-6-yl)imidazo[1,2-a]pyrazin-8-yl]amino}pyridin-2-yl)oxy]ethan-1-ol;
3,3-dimethyl-6-(8-{[6-(morpholin-4-yl)pyridin-3-yl]amino}imidazo[1,2-a]pyrazin-6-yl)-2,3-dihydro-1H-indol-2-one;
1-(5-{[6-(1H-indazol-6-yl)imidazo[1,2-a]pyrazin-8-yl]amino}pyridin-2-yl)-3-methylazetidin-3-ol;
1-(6-{[6-(1H-indazol-6-yl)imidazo[1,2-a]pyrazin-8-yl]amino}pyridin-3-yl)azetidin-3-ol;
2-(5-{[6-(1H-indazol-6-yl)imidazo[1,2-a]pyrazin-8-yl]amino}pyridin-2-yl)-2-methylpropan-1-ol;
1-[(5-{[6-(1H-indazol-6-yl)imidazo[1,2-a]pyrazin-8-yl]amino}pyridin-2-yl)oxy]-2-methylpropan-2-ol;
N-[5-(3,4-dihydro-2H-1,4-benzoxazin-6-yl)pyrazolo[1,5-a]pyrimidin-7-yl]-5-(morpholin-4-yl)pyridin-2-amine;
N-[5-(1-methyl-1H-1,3-benzodiazol-6-yl)pyrazolo[1,5-a]pyrimidin-7-yl]-5-(morpholin-4-yl)pyridin-2-amine;
6-(7-{[5-(morpholin-4-yl)pyridin-2-yl]amino}pyrazolo[1,5-a]pyrimidin-5-yl)-2,3-dihydro-1H-indol-2-one;
N-[6-(3,4-dihydro-2H-1,4-benzoxazin-6-yl)imidazo[1,2-a]pyrazin-8-yl]-6-(morpholin-4-yl)pyridin-3-amine;
N-[6-(3,4-dihydro-2H-1,4-benzoxazin-7-yl)imidazo[1,2-a]pyrazin-8-yl]-6-(morpholin-4-yl)pyridin-3-amine;
2-(6-{[5-(1H-indazol-6-yl)pyrazolo[1,5-a]pyrimidin-7-yl]amino}pyridin-3-yl)(methyl)amino]ethan-1-ol;
6-(7-{[5-(morpholin-4-yl)pyridin-2-yl]amino}pyrazolo[1,5-a]pyrimidin-5-yl)-3,4-dihydro-2H-1,4-benzoxazin-3-one;
N-[5-(1H-indol-6-yl)pyrazolo[1,5-a]pyrimidin-7-yl]-5-(morpholin-4-yl)pyridin-2-amine;
6-(8-{[6-(morpholin-4-yl)pyridin-3-yl]amino}imidazo[1,2-a]pyrazin-6-yl)-2,3-dihydro-1H-indol-2-one;
N-[6-(1-methyl-1H-1,3-benzodiazol-5-yl)imidazo[1,2-a]pyrazin-8-yl]-6-(morpholin-4-yl)pyridin-3-amine;
2-[(5-{[6-(3,4-dihydro-2H-1,4-benzoxazin-7-yl)imidazo[1,2-a]pyrazin-8-yl]amino}pyridin-2-yl)(methyl)amino]ethan-1-ol;
N-[6-(1-methyl-1H-1,3-benzodiazol-6-yl)imidazo[1,2-a]pyrazin-8-yl]-6-(morpholin-4-yl)pyridin-3-amine;
1-(5-{[6-(3,4-dihydro-2H-1,4-benzoxazin-6-yl)imidazo[1,2-a]pyrazin-8-yl]amino}pyridin-2-yl)-4-methylpiperidin-4-ol;
N-[6-(1H-1,3-benzodiazol-6-yl)imidazo[1,2-a]pyrazin-8-yl]-6-(morpholin-4-yl)pyridin-3-amine;
1-(5-{[6-(3,4-dihydro-2H-1,4-benzoxazin-6-yl)imidazo[1,2-a]pyrazin-8-yl]amino}pyridin-2-yl)azetidin-3-ol;
N-[5-(1H-1,3-benzodiazol-6-yl)pyrazolo[1,5-a]pyrimidin-7-yl]-5-(morpholin-4-yl)pyridin-2-amine;
1-(5-{[6-(1H-indol-6-yl)imidazo[1,2-a]pyrazin-8-yl]amino}pyridin-2-yl)-4-methylpiperidin-4-ol;
N-[6-(1H-indol-6-yl)imidazo[1,2-a]pyrazin-8-yl]-6-(morpholin-4-yl)pyridin-3-amine;
6-(8-{[6-(morpholin-4-yl)pyridin-3-yl]amino}imidazo[1,2-a]pyrazin-6-yl)-3,4-dihydro-2H-1,4-benzoxazin-3-one;
1-ethyl-N-[6-(1H-indazol-6-yl)imidazo[1,2-a]pyridin-8-yl]-5-methyl-1H-pyrazol-3-amine;
6-[8-({6-[(2-hydroxyethyl)(methyl)amino]pyridin-3-yl}amino)imidazo[1,2-a]pyrazin-6-yl]-3,4-dihydro-2H-1,4-benzoxazin-3-one;
1-(5-{[6-(1H-indazol-6-yl)imidazo[1,2-a]pyrazin-8-yl]amino}pyridin-2-yl)-3-methylpiperidin-3-ol;
N-[6-(1H-indazol-6-yl)imidazo[1,2-a]pyrazin-8-yl]-6-(morpholin-4-yl)pyridazin-3-amine;
7-(8-{[6-(morpholin-4-yl)pyridin-3-yl]amino}imidazo[1,2-a]pyrazin-6-yl)-1H,2H,3H-pyrido[2,3-b][1,4]oxazin-2-one;
N-[6-(1H-indazol-6-yl)imidazo[1,2-a]pyrazin-8-yl]-6-[4-(propan-2-yl)piperazin-1-yl]pyridin-3-amine;
N-[6-(4-fluoro-1H-indazol-6-yl)imidazo[1,2-a]pyrazin-8-yl]-6-(morpholin-4-yl)pyridin-3-amine;
2-N-[6-(1H-indazol-6-yl)imidazo[1,2-a]pyridin-8-yl]-5-N-(2-methoxyethyl)-5-N-methylpyridine-2,5-diamine;
6-(1H-benzo[d]imidazol-6-yl)-N-(5-morpholinopyridin-2-yl)imidazo[1,2-b]pyridazin-8-amine;
6-(3-amino-1H-indazol-6-yl)-N-(5-morpholinopyridin-2-yl)imidazo[1,2-b]pyridazin-8-amine;
2-[(6-{[6-(1H-indazol-6-yl)imidazo[1,2-a]pyridin-8-yl]amino}pyridin-3-yl)(methyl)amino]ethan-1-ol;
1-(5-{[6-(1H-indazol-6-yl)imidazo[1,2-a]pyrazin-8-yl]amino}pyridin-2-yl)-4-methylpiperidin-4-ol;
1-(5-{[6-(1H-indazol-6-yl)imidazo[1,2-a]pyrazin-8-yl]amino}pyridin-2-yl)azetidin-3-ol;
6-(1H-indol-6-yl)-N-(5-morpholinopyridin-2-yl)imidazo[1,2-b]pyridazin-8-amine; and
N-[6-(5-fluoro-1H-indazol-6-yl)imidazo[1,2-a]pyrazin-8-yl]-6-(morpholin-4-yl)pyridin-3-amine,
and pharmaceutically acceptable salts thereof.

Also provided is at least one chemical entity chosen from:
N-[6-(1H-indazol-6-yl)imidazo[1,2-a]pyrazin-8-yl]-6-(morpholin-4-yl)pyridin-3-amine;
N-[6-(2,3-dimethyl-2H-indazol-6-yl)imidazo[1,2-a]pyrazin-8-yl]-6-(morpholin-4-yl)pyridin-3-amine;
5-N-[6-(1H-indazol-6-yl)imidazo[1,2-a]pyrazin-8-yl]-2-N-(2-methoxyethyl)-2-N-methylpyridine-2,5-diamine; and
2-[(5-{[6-(1H-indazol-6-yl)imidazo[1,2-a]pyrazin-8-yl]amino}pyridin-2-yl)(methyl)amino]ethan-1-ol,
and pharmaceutically acceptable salts thereof.

Also provided is at least one chemical entity chosen from:
(3S)-1-(5-{[6-(1H-indazol-6-yl)imidazo[1,2-a]pyrazin-8-yl]amino}pyridin-2-yl)-3-methylpiperidin-3-ol,
(3R)-1-(5-{[6-(1H-indazol-6-yl)imidazo[1,2-a]pyrazin-8-yl]amino}pyridin-2-yl)-3-methylpiperidin-3-ol,
1-(5-{[6-(1H-indol-6-yl)imidazo[1,2-a]pyrazin-8-yl]amino}pyridin-2-yl)-3-methylazetidin-3-ol,
[(2R)-4-(5-{[6-(1H-indazol-6-yl)imidazo[1,2-a]pyrazin-8-yl]amino}pyridin-2-yl)morpholin-2-yl]methanol,
[(2S)-4-(5-{[6-(1H-indazol-6-yl)imidazo[1,2-a]pyrazin-8-yl]amino}pyridin-2-yl)morpholin-2-yl]methanol,
N-[6-(1H-indazol-6-yl)imidazo[1,2-a]pyrazin-8-yl]-2-(morpholin-4-yl)pyrimidin-5-amine,
1-ethyl-N-(6-{1H-pyrrolo[3,2-b]pyridin-6-yl}imidazo[1,2-a]pyrazin-8-yl)-1H-pyrazol-4-amine, and
2-{4-[(6-{1H-pyrrolo[3,2-b]pyridin-6-yl}imidazo[1,2-a]pyrazin-8-yl)amino]-1H-pyrazol-1-yl}ethan-1-ol,
and pharmaceutically acceptable salts thereof.

In all of the foregoing examples, the chemical entities can be administered alone, as mixtures, or in combination with other active agents.

Methods for obtaining the novel compounds described herein will be apparent to those of ordinary skill in the art, suitable procedures being described, for example, in the reaction schemes and examples below, and in the references cited herein.

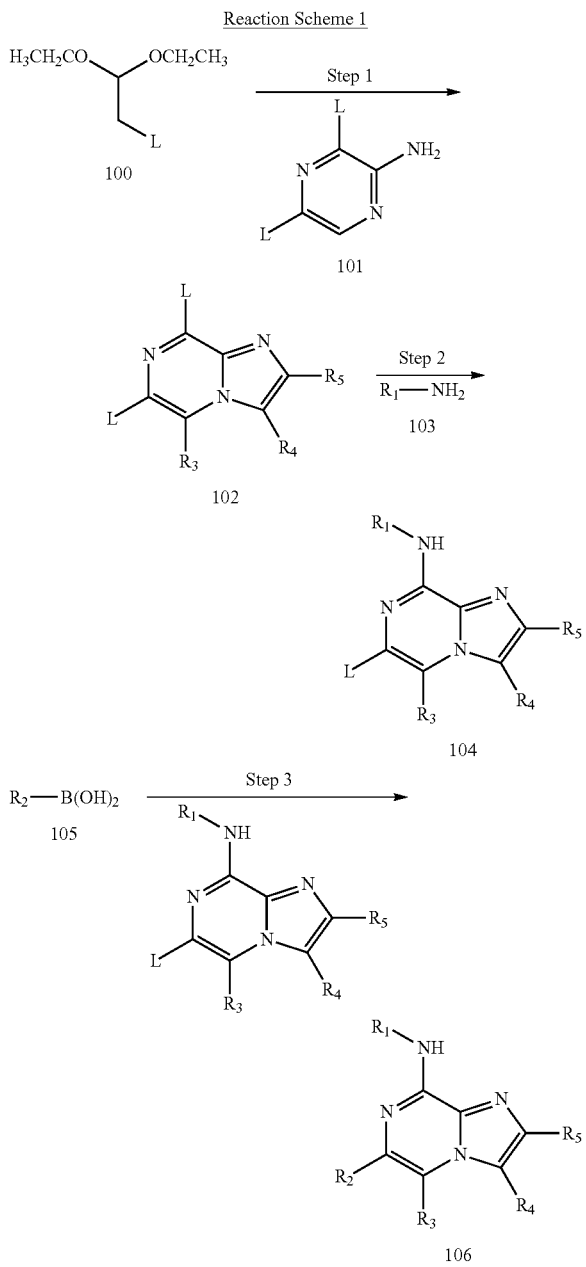

Reaction Scheme 1

Referring to Reaction Scheme 1, Step 1, an excess (such as about 3.5 equivalents) of a compound of Formula 100, where L is a leaving group such as bromide is combined with an aqueous solution of acid (such as 48% aqueous hydrogen bromide), and the mixture is stirred at reflux for about 2 h. The mixture is cooled to about 40° C. and base (such as solid sodium bicarbonate) is added. The reaction mixture is filtered and a compound of Formula 101, where L is a leaving group such as bromide is added, and the reaction mixture is stirred at reflux for about 16 h. The product, a compound of Formula 102, is isolated and optionally purified.

Referring to Reaction Scheme 1, Step 2, a mixture of a compound of Formula 102, where L is a leaving group such as bromide is combined with an excess of a compound of Formula 103 (such as about 3 equivalents) and an excess of an organic base (such as about 1.7 equivalents), such as N,N-diisopropylethylamine in a polar solvent such as N,N-dimethylformamide. The reaction mixture is stirred at about 100° C. for about 3 h. The product, a compound of Formula 104, is isolated and optionally purified.

Referring to Reaction Scheme 1, Step 3, a mixture of a compound of Formula 104, where L is a leaving group such as bromide is combined with an excess of a compound of Formula 105 (such as 1.1 equivalents) and an aqueous solution of base (such as 1 M aqueous sodium carbonate) in an inert solvent, such as 1,4 dioxane. The reaction mixture is sparged with nitrogen and stirred for about 5 min. The resulting mixture is treated with about 0.1 equivalent of tetrakis(triphenylphosphine)palladium(0) and reacted under microwave irradiation at about 135° C. for about 30 min. The resulting product, a compound of Formula 106, is isolated and optionally purified.

Accordingly, provided is a method of treating a patient, for example, a mammal, such as a human, having a disease responsive to inhibition of Syk activity, comprising administrating to the patient having such a disease, an effective amount of at least one chemical entity described herein.

In some embodiments, the chemical entities described herein may also inhibit other kinases, such that disease, disease symptoms, and conditions associated with these kinases is also treated.

Methods of treatment also include inhibiting Syk activity and/or inhibiting B-cell activity, by inhibiting ATP binding or hydrolysis by Syk or by some other mechanism, in vivo, in a patient suffering from a disease responsive to inhibition of Syk activity, by administering an effective concentration of at least one chemical entity chosen described herein. An example of an effective concentration would be that concentration sufficient to inhibit Syk activity in vitro. An effective concentration may be ascertained experimentally, for example by assaying blood concentration of the chemical entity, or theoretically, by calculating bioavailability.

In some embodiments, the condition responsive to inhibition of Syk activity and/or B-cell activity is cancer, an allergic disorder and/or an autoimmune and/or inflammatory disease, and/or an acute inflammatory reaction. Also provided is a method of treating a patient having cancer, an allergic disorder and/or an autoimmune and/or inflammatory disease, and/or an acute inflammatory reaction, by administering an effective amount of at least one chemical entity described herein.

In some embodiments, the conditions and diseases that can be affected using chemical entities described herein, include, but are not limited to: allergic disorders, including but not limited to eczema, allergic rhinitis or coryza, hay fever, bronchial asthma, urticaria (hives) and food allergies, and other atopic conditions; autoimmune and/or inflammatory diseases, including but not limited to psoriasis, Crohn's disease, irritable bowel syndrome, Sjogren's disease, tissue graft rejection, and hyperacute rejection of transplanted organs, asthma, systemic lupus erythematosus (and associated glomerulonephritis), dermatomyositis, multiple sclerosis, scleroderma, vasculitis (ANCA-associated and other vasculitides), autoimmune hemolytic and thrombocytopenic states, Goodpasture's syndrome (and associated glomerulonephritis and pulmonary hemorrhage), atherosclerosis, rheumatoid arthritis, chronic Idiopathic thrombocytopenic purpura (ITP), Addison's disease, Parkinson's disease, Alzheimer's disease, diabetes, septic shock, myasthenia gravis, and the like; acute inflammatory reactions, including but not limited to skin sunburn, inflammatory pelvic disease, inflammatory bowel disease, urethritis, uvitis, sinusitis, pneumonitis, encephalitis, meningitis, myocarditis, nephritis, osteomyelitis, myositis, hepatitis, gastritis, enteritis, dermatitis, gingivitis, appendicitis, pancreatitis, and cholocystitis; polycystic kidney disease, and cancer, including but not limited to, B-cell lymphoma, lymphoma (including Hodgkin's and non-Hodgkins lymphoma), hairy cell leukemia, multiple myeloma, chronic and acute myelogenous leukemia, and chronic and acute lymphocytic leukemia.

Syk is a known inhibitor of apoptosis in lymphoma B-cells. Defective apoptosis contributes to the pathogenesis and drug resistance of human leukemias and lymphomas. Thus, further provided is a method of promoting or inducing apoptosis in cells expressing Syk comprising contacting the cell with at least one chemical entity described herein.

Also provided are methods of treatment in which at least one chemical entity described herein is the only active agent given to a patient and also includes methods of treatment in which at least one chemical entity described herein is given to a patient in combination with one or more additional active agents.

Thus in some embodiments, a method of treating cancer, an allergic disorder and/or an autoimmune and/or inflammatory disease, and/or an acute inflammatory reaction comprises administering to a patient in need thereof an effective amount of at least one chemical entity described herein, together with a second active agent, which can be useful for treating a cancer, an allergic disorder and/or an autoimmune and/or inflammatory disease, and/or an acute inflammatory reaction. For example the second agent may be an anti-inflammatory agent. Treatment with the second active agent may be prior to, concomitant with, or following treatment with at least one chemical entity described herein. In some embodiments, at least one chemical entity described herein is combined with another active agent in a single dosage form. Suitable antitumor therapeutics that may be used in combination with at least one chemical entity described herein include, but are not limited to, chemotherapeutic agents, for example mitomycin C, carboplatin, taxol, cisplatin, paclitaxel, etoposide, doxorubicin, or a combination comprising at least one of the foregoing chemotherapeutic agents. Radiotherapeutic antitumor agents may also be used, alone or in combination with chemotherapeutic agents.

Chemical entities described herein can be useful as chemosensitizing agents, and, thus, can be useful in combination with other chemotherapeutic drugs, in particular, drugs that induce apoptosis.

A method for increasing sensitivity of cancer cells to chemotherapy, comprising administering to a patient undergoing chemotherapy a chemotherapeutic agent together with at least one chemical entity described herein in an amount sufficient to increase the sensitivity of cancer cells to the chemotherapeutic agent is also provided herein.

Examples of other chemotherapeutic drugs that can be used in combination with chemical entities described herein include topoisomerase I inhibitors (camptothesin or topotecan), topoisomerase II inhibitors (e.g. daunomycin and etoposide), alkylating agents (e.g. cyclophosphamide, melphalan and BCNU), tubulin directed agents (e.g. taxol and vinblastine), and biological agents (e.g. antibodies such as anti CD20 antibody, IDEC 8, immunotoxins, and cytokines).

In some embodiments, the chemical entities described herein are used in combination with Rituxan® (Rituximab) or other agents that work by selectively depleting CD20+ B-cells.

Included herein are methods of treatment in which at least one chemical entity described herein is administered in combination with an anti-inflammatory agent. Anti-inflammatory agents include but are not limited to NSAIDs, non-specific and COX-2 specific cyclooxgenase enzyme inhibitors, gold compounds, corticosteroids, methotrexate, tumor necrosis factor receptor (TNF) receptors antagonists, immunosuppressants and methotrexate.

Examples of NSAIDs include, but are not limited to ibuprofen, flurbiprofen, naproxen and naproxen sodium, diclofenac, combinations of diclofenac sodium and misoprostol, sulindac, oxaprozin, diflunisal, piroxicam, indomethacin, etodolac, fenoprofen calcium, ketoprofen, sodium nabumetone, sulfasalazine, tolmetin sodium, and hydroxychloroquine. Examples of NSAIDs also include COX-2 specific inhibitors (i.e., a compound that inhibits COX-2 with an $IC_{50}$ that is at least 50-fold lower than the $IC_{50}$ for COX-1) such as celecoxib, valdecoxib, lumiracoxib, etoricoxib and/or rofecoxib.

In some embodiments, the anti-inflammatory agent is a salicylate. Salicylates include but are not limited to acetylsalicylic acid or aspirin, sodium salicylate, and choline and magnesium salicylates.

The anti-inflammatory agent may also be a corticosteroid. For example, the corticosteroid may be chosen from cortisone, dexamethasone, methylprednisolone, prednisolone, prednisolone sodium phosphate, and prednisone.

In some embodiments, the anti-inflammatory therapeutic agent is a gold compound such as gold sodium thiomalate or auranofin.

In some embodiments, the anti-inflammatory agent is a metabolic inhibitor such as a dihydrofolate reductase inhibitor, such as methotrexate or a dihydroorotate dehydrogenase inhibitor, such as leflunomide.

In some embodiments, combinations in which at least one anti-inflammatory compound is an anti-$C_5$ monoclonal antibody (such as eculizumab or pexelizumab), a TNF antagonist, such as entanercept, or infliximab, which is an anti-TNF alpha monoclonal antibody are used.

In some embodiments, combinations in which at least one active agent is an immunosuppressant compound such as methotrexate, leflunomide, cyclosporine, tacrolimus, azathioprine, or mycophenolate mofetil are used.

Dosage levels of the order, for example, of from 0.1 mg to 140 mg per kilogram of body weight per day can be useful in the treatment of the above-indicated conditions (0.5 mg to 7 g per patient per day). The amount of active ingredient that may be combined with the vehicle to produce a single dosage form will vary depending upon the host treated and the particular mode of administration. Dosage unit forms will generally contain from 1 mg to 500 mg of an active ingredient.

Frequency of dosage may also vary depending on the compound used and the particular disease treated. In some embodiments, for example, for the treatment of an allergic disorder and/or autoimmune and/or inflammatory disease, a dosage regimen of 4 times daily or less is used. In some embodiments, a dosage regimen of 1 or 2 times daily is used. It will be understood, however, that the specific dose level for any particular patient will depend upon a variety of factors including the activity of the specific compound employed, the age, body weight, general health, sex, diet, time of administration, route of administration, and rate of excretion, drug combination and the severity of the particular disease in the patient undergoing therapy.

A labeled form of a chemical entity described herein can be used as a diagnostic for identifying and/or obtaining compounds that have the function of modulating an activity of a kinase as described herein. The chemical entities described herein may additionally be used for validating, optimizing, and standardizing bioassays.

By "labeled" herein is meant that the compound is either directly or indirectly labeled with a label which provides a detectable signal, e.g., radioisotope, fluorescent tag, enzyme, antibodies, particles such as magnetic particles, chemiluminescent tag, or specific binding molecules, etc. Specific binding molecules include pairs, such as biotin and streptavidin, digoxin and antidigoxin etc. For the specific binding members, the complementary member would normally be labeled with a molecule which provides for detection, in accordance with known procedures, as outlined above. The label can directly or indirectly provide a detectable signal.

EXAMPLES

The invention is further illustrated by the following non-limiting examples.

In the examples below, the following abbreviations have the following meanings. If an abbreviation is not defined, it has its generally accepted meaning.

DME=dimethyl ether
DMEM=Dulbecco's modified Eagle's medium
DMF=N,N-dimethylformamide
DMSO=dimethylsulfoxide
Et$_2$O=diethylether
g=gram
h=hour
mg=milligram
min=minutes
mL=milliliter
mmol=millimoles
mM=millimolar
ng=nanogram
nm=nanometer
nM=nanomolar
PBS=phosphate buffered saline
µL=microliter
µM=micromolar Example I Preparation of 6-(1H-indazol-6-yl)-N-(1-isopropyl-1H-pyrazol-4-yl)imidazo[1,2-a]pyrazin-8-amine (5)

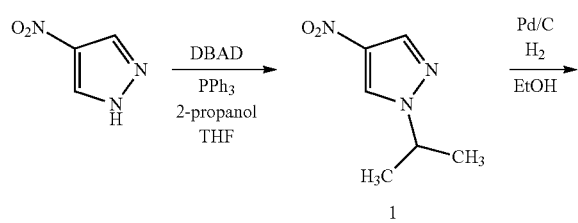

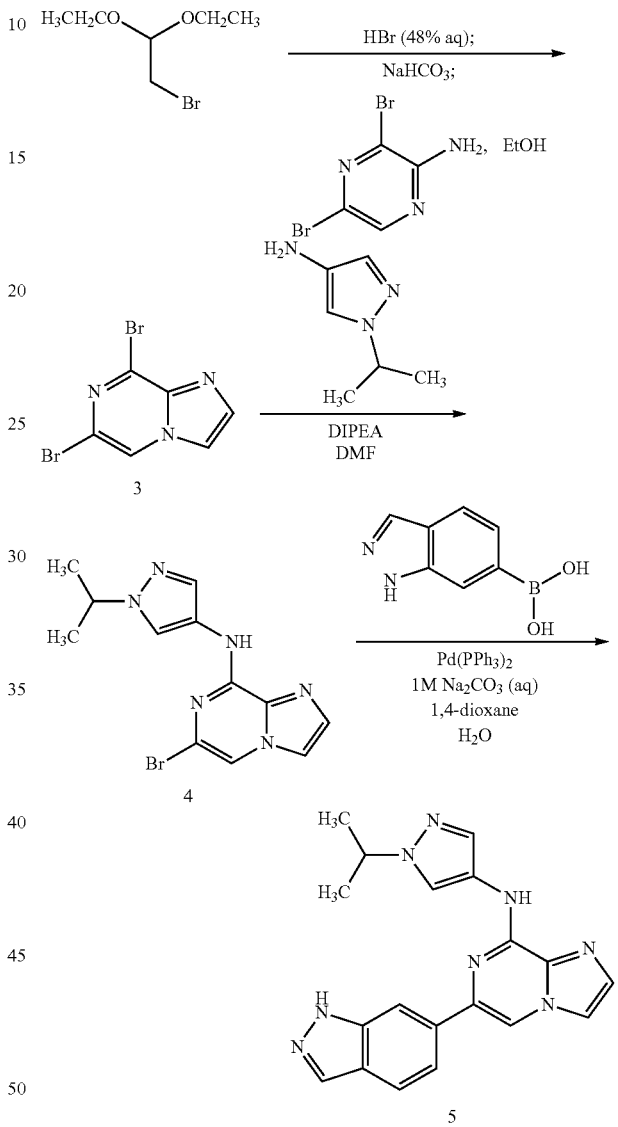

Preparation of 1-isopropyl-4-nitro-1H-pyrazole (1)

Di-tert-butyl azodicarboxylate (1.59 g, 6.91 mmol) was added to a solution of 4-nitro-1H-pyrazole (601 mg, 5.32 mmol), 2-propanol (319 mg, 5.32 mmol) and triphenylphosphine (1.67 g, 6.36 mmol) in tetrahydrofuran (25 mL) over 3 minutes and the mixture was stirred at room temperature for 16 h. After this time, the reaction was concentrated under reduced pressure and the resulting residue purified by chromatography (silica, gradient, 1:4 ethyl acetate/heptane to 7:3 ethyl acetate/heptane) to afford 1-isopropyl-4-nitro-1H-pyrazole (1) (1.23 g, >100%) as an impure off-white solid, which was used without further purification: $^1$H NMR (300 MHz, DMSO-$d_6$) δ 8.91 (s, 1H), 8.24 (s, 1H), 4.58 (m, 1H), 1.42 (d, J=6.6 Hz, 6H).

Preparation of 1-isopropyl-1H-pyrazole-4-amine (2)

A suspension of impure 1-isopropyl-4-nitro-1H-pyrazole (1) (1.23 g), from above, in ethanol (50 mL) was treated with 10% palladium on carbon (400 mg, 50% water by weight) and shaken under a hydrogen atmosphere (35 psi) at room temperature for 1 h. After this time, the reaction was filtered through diatomaceous earth and the filtrate concentrated under reduced pressure to afford 1-isopropyl-1H-pyrazole-4-amine (2) (1.15 g) as an impure off-white solid, which was used without further purification: $^1$H NMR (300 MHz, DMSO-$d_6$) δ 7.02 (s, 1H), 6.87 (s, 1H), 4.26 (m, 1H), 3.72 (bs, 2H), 1.42 (d, J=6.6 Hz, 6H).

Preparation of 6,8-dibromoimidazo[1,2-a]pyrazine (3)

A 1-L four-neck round bottom flask equipped with a temperature probe, mechanical stirrer and reflux condenser was charged with 2-bromo-1,1-diethoxyethane (68.1 g, 346 mmol) and 48% aqueous hydrogen bromide (11.3 mL, 99.2 mmol), and the reaction mixture was stirred at reflux for 2 h. The resulting mixture was allowed to cool to 40° C. and solid sodium bicarbonate (8.50 g, 101 mmol) was added in small portions until gas evolution was observed to cease. Caution: initial addition of sodium bicarbonate to the warm solution resulted in vigorous gas evolution (foaming). The resulting suspension was filtered into a 1-L four-neck round bottomed flask and the filter cake was washed with ethanol (200 mL). The flask was equipped with a temperature probe, mechanical stirrer and reflux condenser. 3,5-Dibromopyrazin-2-amine (50.0 g, 198 mmol) was added and the reaction mixture was heated at reflux, with vigorous stirring, for 16 h. After this time, the suspension was cooled to 0° C. and filtered. The filter cake was washed with cold ethanol (50 mL), dried under vacuum and added to a 1-L three-neck round bottomed flask equipped with a mechanical stirrer. Water (200 mL) was added and the vigorously stirred suspension was treated portion-wise with solid potassium carbonate (27.4 g, 198 mmol). Caution: gas evolution upon the addition of potassium carbonate observed. After stirring for 30 min, the resulting precipitate was isolated by filtration and the filter cake washed with water (100 mL) followed by ethanol (50 mL). The filter cake was dried at 50° C. to a constant weight, under vacuum to provide 6,8-dibromoimidazo[1,2-a]pyrazine (3) (52.0 g, 94%) as a light yellow solid: $^1$H NMR (300 MHz, DMSO-$d_6$) δ 9.02 (s, 1H), 8.23 (s, 1H), 7.90 (s, 1H).

Preparation of 6-bromo-N-(1-isopropyl-1H-pyrazol-4-yl)imidazo[1,2-a]pyrazin-8-amine (4)

A mixture of impure 1-isopropyl-1H-pyrazole-4-amine (2) (1.00 g), from above, 6,8-dibromoimidazo[1,2-a]pyrazine (3) (750 mg, 2.71 mmol), and N,N-diisopropylethylamine (526 mg, 4.16 mmol) in DMF (20 mL) was stirred at 100° C. for 3 h. After this time, the reaction was cooled to room temperature and poured into ice water (200 mL). The resulting suspension was filtered and the filter cake dried to a constant weight under vacuum to afford impure 6-bromo-N-(1-isopropyl-1H-pyrazol-4-yl)imidazo[1,2-a]pyrazin-8-amine (4) (1.26 g) as an off-white solid, which was used without further purification: $^1$H NMR (300 MHz, DMSO-$d_6$) δ 10.26 (s, 1H), 8.14 (s, 1H), 8.08 (s, 1H), 7.90 (s, 1H), 7.77 (s, 1H), 7.59 (s, 1H), 4.49 (m, 1H), 1.40 (d, 6H); ESI MS m/z 323.3 [M+H]$^+$.

Preparation of 6-(1H-indazol-6-yl)-N-(1-isopropyl-1H-pyrazol-4-yl)imidazo[1,2-a]pyrazin-8-amine (5)

A mixture of impure 6-bromo-N-(1-isopropyl-1H-pyrazol-4-yl)imidazo[1,2-a]pyrazin-8-amine (4) (195 mg), from above, and 1H-indazol-6-ylboronic acid (159 mg, 0.650 mmol) in 1 M aqueous sodium carbonate (1.3 mL) and 1,4-dioxane (3.5 mL) was sparged with nitrogen while stirring for 5 min. Tetrakis(triphenylphosphine)palladium(0) (69 mg, 0.060 mmol) was then added and the resulting mixture heated under microwave irradiation at 135° C. for 30 min. After this time, the reaction was diluted with methylene chloride (30 mL) and water (20 mL), and filtered through diatomaceous earth. The filtrate layers were separated and the aqueous phase was extracted with a mixture of 9:1 methylene chloride/methanol (100 mL). The combined organic layers were concentrated under reduced pressure and the resulting residue was purified by chromatography (silica, gradient, methylene chloride to 8:2 methylene chloride/methanol), then trituration with acetonitrile to afford 6-(1H-indazol-6-yl)-N-(1-isopropyl-1H-pyrazol-4-yl)imidazo[1,2-a]pyrazin-8-amine (5) (85 mg, 35%) as a yellow solid: mp>250° C.; $^1$H NMR (300 MHz, DMSO-$d_6$) δ 13.23 (s, 1H), 9.95 (s, 1H), 8.59 (s, 1H), 8.24 (s, 1H), 8.18 (s, 1H), 8.10 (s, 1H), 8.00 (s, 1H), 7.97 (d, J=1.2 Hz, 1H), 7.85 (d, J=8.7 Hz, 1H), 7.75 (dd, J=8.7, 1.2 Hz, 1H), 7.62 (s, 1H), 4.52 (m, 1H), 1.47 (d, J=6.6 Hz, 6H); ESI MS m/z 359.4 [M+H]$^+$; HPLC, 5.37 min, >99% (AUC).

Example 2

The following compounds were prepared using procedures similar to those described above. Those of ordinary skill in the art of organic synthesis will recognize when starting materials or reaction conditions should be varied to obtain the desired compound.

MS data reported in this example was obtained as follows: MS conditions: Electrospray MS is performed on a MICROMASS LCT equipped with a LockSpray source for accurate mass measurements. Spectra are acquired in positive ion mode from 100-1000 Da at an acquisition rate of 1 spectrum/0.9 s with a 0.1 s interscan delay. The instrument is tuned for a resolution of 5000 (FWHM). Every 5$^{th}$ scan is taken from the reference position of the Lockspray source. Leucine enkephalin (556.2771 [M+H]$^+$) is used as the reference, or lock mass.

| Structure | Name | [M + H]⁺ |
|---|---|---|
| 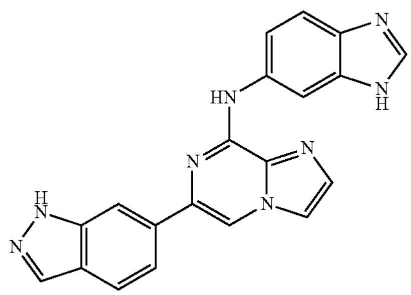 [SMILES: c1cn2cc(-c3ccc4cn[nH]c4c3)nc(Nc3ccc4nc[nH]c4c3)c2n1] | N-[6-(1H-indazol-6-yl)imidazo[1,2-a]pyrazin-8-yl]-1H-1,3-benzodiazol-6-amine | 367.3 |
| 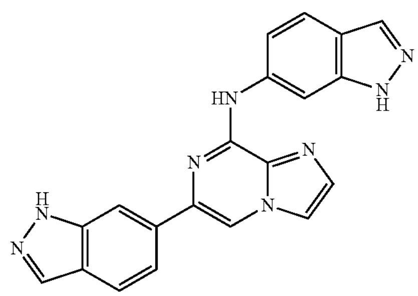 [SMILES: c1cn2cc(-c3ccc4cn[nH]c4c3)nc(Nc3ccc4cn[nH]c4c3)c2n1] | N-[6-(1H-indazol-6-yl)imidazo[1,2-a]pyrazin-8-yl]-1H-indazol-6-amine | 367.3 |
| 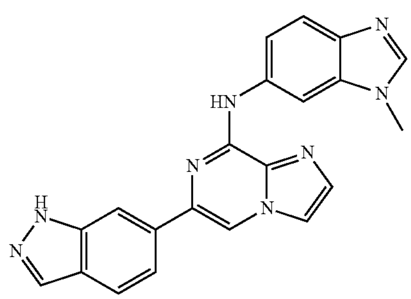 [SMILES: Cn1cnc2ccc(Nc3nc(-c4ccc5cn[nH]c5c4)cn4ccnc34)cc21] | N-[6-(1H-indazol-6-yl)imidazo[1,2-a]pyrazin-8-yl]-1-methyl-1H-1,3-benzodiazol-6-amine | 381.3 |
| 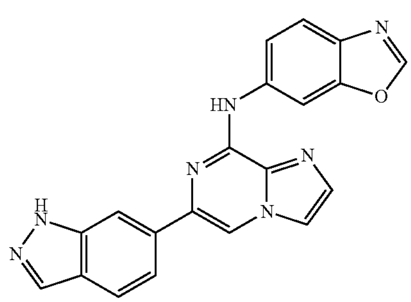 [SMILES: c1cn2cc(-c3ccc4cn[nH]c4c3)nc(Nc3ccc4ncoc4c3)c2n1] | N-[6-(1H-indazol-6-yl)imidazo[1,2-a]pyrazin-8-yl]-1,3-benzoxazol-6-amine | 368.3 |
| 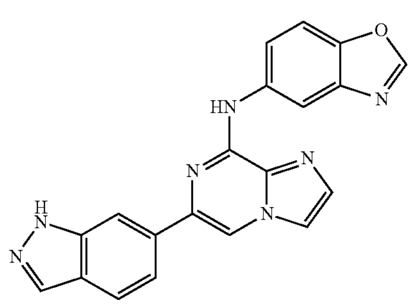 | N-[6-(1H-indazol-6-yl)imidazo[1,2-a]pyrazin-8-yl]-1,3-benzoxazol-5-amine | 368.3 |

| Structure | Name | [M + H]+ |
|---|---|---|
| 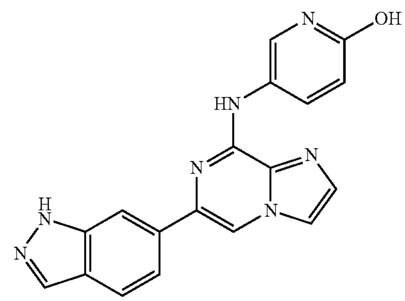 [SMILES: Oc1ccc(Nc2nc(-c3ccc4cn[nH]c4c3)cn3ccnc23)cn1] | 5-{[6-(1H-indazol-6-yl)imidazo[1,2-a]pyrazin-8-yl]amino}pyridin-2-ol | 344.3 |
| 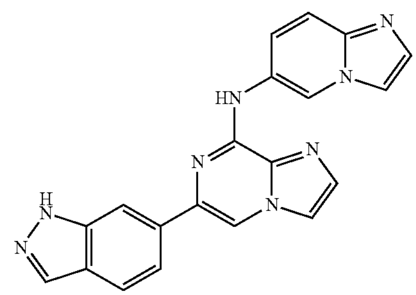 [SMILES: c1cn2cc(Nc3nc(-c4ccc5cn[nH]c5c4)cn4ccnc34)ccc2n1] | N-{imidazo[1,2-a]pyridin-6-yl}-6-(1H-indazol-6-yl)imidazo[1,2-a]pyrazin-8-amine | 367.3 |
| 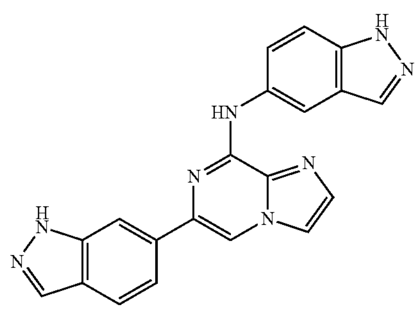 [SMILES: c1cn2cc(-c3ccc4cn[nH]c4c3)nc(Nc3ccc4[nH]ncc4c3)c2n1] | N-[6-(1H-indazol-6-yl)imidazo[1,2-a]pyrazin-8-yl]-1H-indazol-5-amine | 367.3 |
| 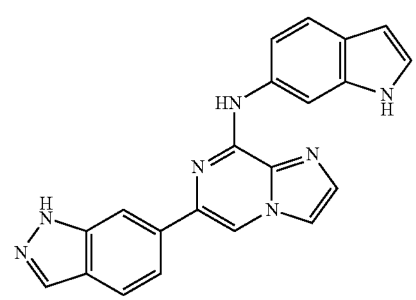 [SMILES: c1cn2cc(-c3ccc4cn[nH]c4c3)nc(Nc3ccc4cc[nH]c4c3)c2n1] | N-[6-(1H-indazol-6-yl)imidazo[1,2-a]pyrazin-8-yl]-1H-indol-6-amine | 366.3 |
| 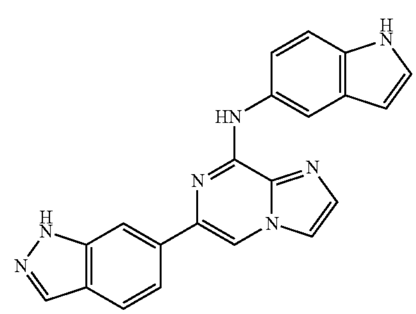 [SMILES: c1cn2cc(-c3ccc4cn[nH]c4c3)nc(Nc3ccc4[nH]ccc4c3)c2n1] | N-[6-(1H-indazol-6-yl)imidazo[1,2-a]pyrazin-8-yl]-1H-indol-5-amine | 366.3 |

-continued

| Structure | Name | [M + H]+ |
|---|---|---|
| 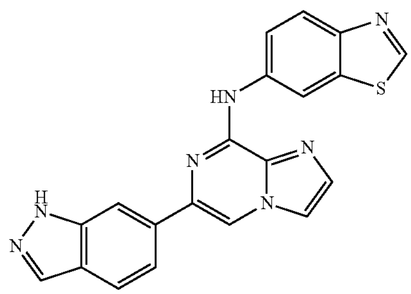 [SMILES: c1cn2cc(-c3ccc4cn[nH]c4c3)nc(Nc3ccc4ncsc4c3)c2n1] | N-[6-(1H-indazol-6-yl)imidazo[1,2-a]pyrazin-8-yl]-1,3-benzothiazol-6-amine | 384.3 |
| 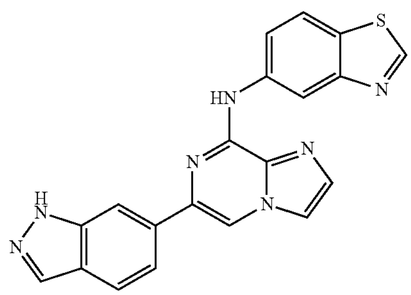 | N-[6-(1H-indazol-6-yl)imidazo[1,2-a]pyrazin-8-yl]-1,3-benzothiazol-5-amine | 384.3 |
| 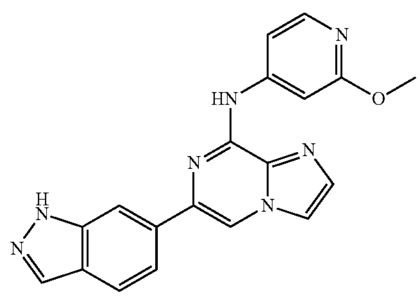 [SMILES: COc1cc(Nc2nc(-c3ccc4cn[nH]c4c3)cn3ccnc23)ccn1] | N-[6-(1H-indazol-6-yl)imidazo[1,2-a]pyrazin-8-yl]-2-methoxypyridin-4-amine | 358.3 |
| 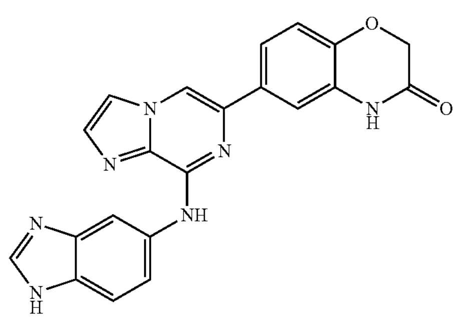 [SMILES: O=C1COc2ccc(-c3cn4ccnc4c(Nc4ccc5[nH]cnc5c4)n3)cc2N1] | 6-[8-(1H-1,3-benzodiazol-5-ylamino)imidazo[1,2-a]pyrazin-6-yl]-3,4-dihydro-2H-1,4-benzoxazin-3-one | 398.1 |
| 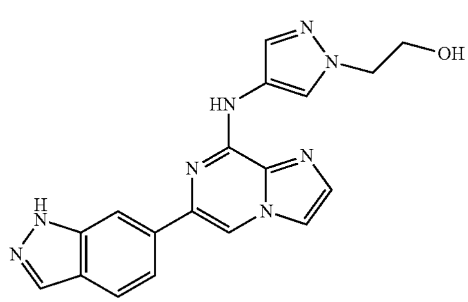 [SMILES: OCCn1cc(Nc2nc(-c3ccc4cn[nH]c4c3)cn3ccnc23)cn1] | 2-(4-{[6-(1H-indazol-6-yl)imidazo[1,2-a]pyrazin-8-yl]amino}-1H-pyrazol-1-yl)ethan-1-ol | 361.4 |

-continued

| Structure | Name | [M + H]+ |
|---|---|---|
| 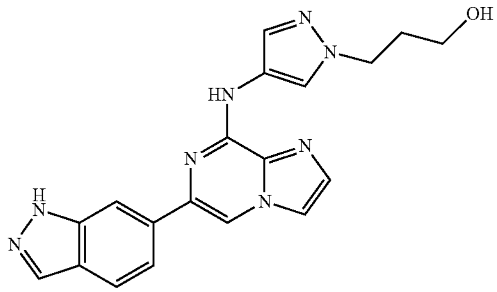 [SMILES: OCCCn1cc(Nc2nc(-c3ccc4cn[nH]c4c3)cn3ccnc23)cn1] | 3-(4-{[6-(1H-indazol-6-yl)imidazo[1,2-a]pyrazin-8-yl]amino}-1H-pyrazol-1-yl)propan-1-ol | 375.2 |
| 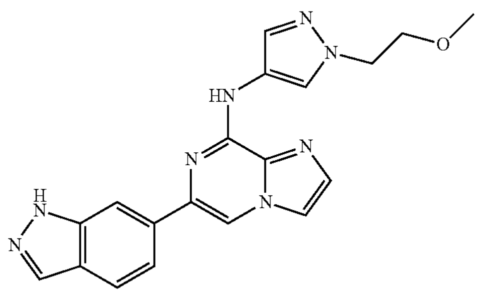 [SMILES: COCCn1cc(Nc2nc(-c3ccc4cn[nH]c4c3)cn3ccnc23)cn1] | N-[6-(1H-indazol-6-yl)imidazo[1,2-a]pyrazin-8-yl]-1-(2-methoxyethyl)-1H-pyrazol-4-amine | 375.4 |
| 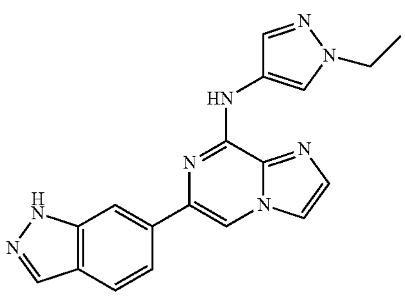 [SMILES: CCn1cc(Nc2nc(-c3ccc4cn[nH]c4c3)cn3ccnc23)cn1] | 1-ethyl-N-[6-(1H-indazol-6-yl)imidazo[1,2-a]pyrazin-8-yl]-1H-pyrazol-4-amine | 345 |
| 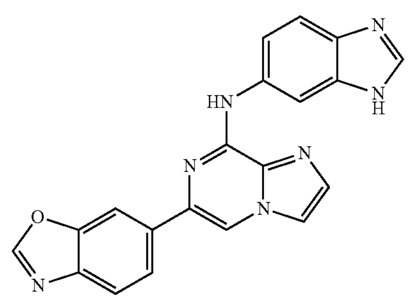 [SMILES: c1cn2cc(-c3ccc4ncoc4c3)nc(Nc3ccc4nc[nH]c4c3)c2n1] | N-[6-(1,3-benzoxazol-6-yl)imidazo[1,2-a]pyrazin-8-yl]-1H-1,3-benzodiazol-6-amine | 368.2 |
| 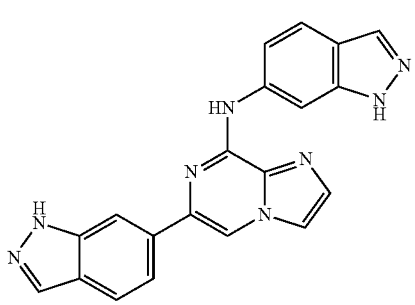 [SMILES: c1cn2cc(-c3ccc4cn[nH]c4c3)nc(Nc3ccc4cn[nH]c4c3)c2n1] | N-[6-(1H-1,3-benzodiazol-6-yl)imidazo[1,2-a]pyrazin-8-yl]-1H-indazol-6-amine | 367.1 |

-continued

| Structure | Name | [M + H]⁺ |
|---|---|---|
| 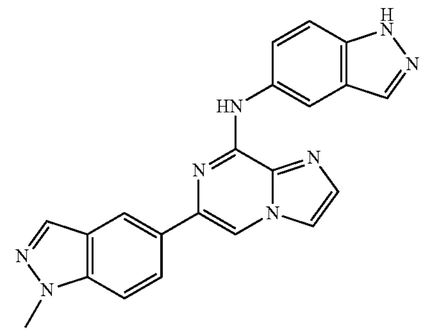 [SMILES: Cn1ncc2cc(-c3cn4ccnc4c(Nc4ccc5[nH]ncc5c4)n3)ccc21] | N-[6-(1-methyl-1H-indazol-5-yl)imidazo[1,2-a]pyrazin-8-yl]-1H-indazol-5-amine | 381.3 |
| 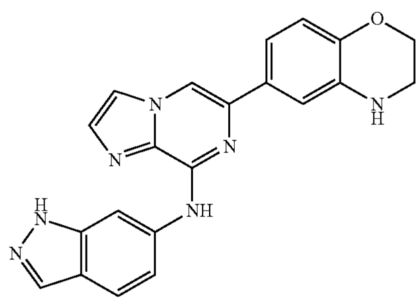 [SMILES: c1cn2cc(-c3ccc4c(c3)NCCO4)nc(Nc3ccc4cn[nH]c4c3)c2n1] | N-[6-(3,4-dihydro-2H-1,4-benzoxazin-6-yl)imidazo[1,2-a]pyrazin-8-yl]-1H-indazol-6-amine | 384.3 |
| 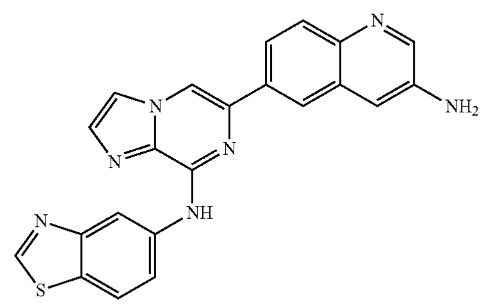 [SMILES: Nc1cnc2ccc(-c3cn4ccnc4c(Nc4ccc5scnc5c4)n3)cc2c1] | N-[6-(3-aminoquinolin-6-yl)imidazo[1,2-a]pyrazin-8-yl]-1,3-benzothiazol-5-amine | 410.3 |
| 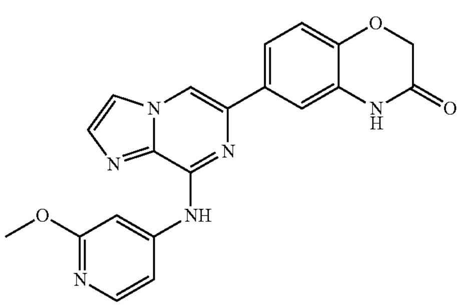 [SMILES: COc1cc(Nc2nc(-c3ccc4c(c3)NC(=O)CO4)cn3ccnc23)ccn1] | 6-{8-[(2-methoxypyridin-4-yl)amino]imidazo[1,2-a]pyrazin-6-yl}-3,4-dihydro-2H-1,4-benzoxazin-3-one | 389.7 |
| 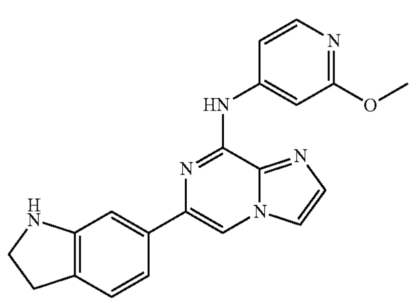 [SMILES: COc1cc(Nc2nc(-c3ccc4c(c3)NCC4)cn3ccnc23)ccn1] | N-[6-(2,3-dihydro-1H-indol-6-yl)imidazo[1,2-a]pyrazin-8-yl]-2-methoxypyridin-4-amine | 359.3 |

-continued

| Structure | Name | [M + H]+ |
|---|---|---|
| 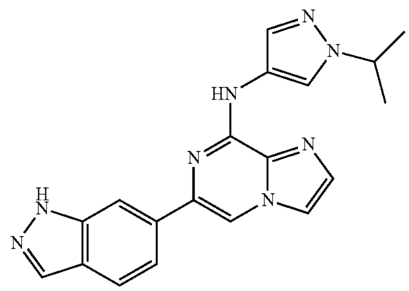 [SMILES: CC(C)n1cc(Nc2nc(-c3ccc4cn[nH]c4c3)cn3ccnc23)cn1] | N-[6-(1H-indazol-6-yl)imidazo[1,2-a]pyrazin-8-yl]-1-(propan-2-yl)-1H-pyrazol-4-amine | 359.4 |
| 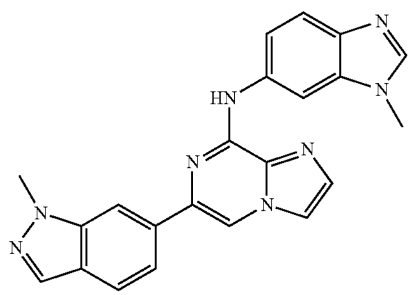 [SMILES: Cn1cnc2ccc(Nc3nc(-c4ccc5cnn(C)c5c4)cn4ccnc34)cc21] | 1-methyl-N-[6-(1-methyl-1H-indazol-6-yl)imidazo[1,2-a]pyrazin-8-yl]-1H-1,3-benzodiazol-6-amine | 395.1 |
| 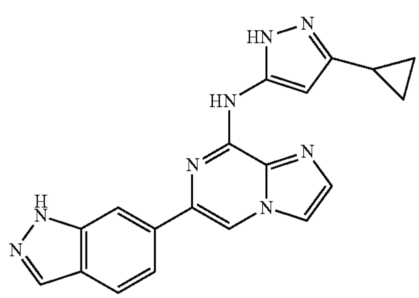 [SMILES: c1cn2cc(-c3ccc4cn[nH]c4c3)nc(Nc3cc(C4CC4)n[nH]3)c2n1] | 3-cyclopropyl-N-[6-(1H-indazol-6-yl)imidazo[1,2-a]pyrazin-8-yl]-1H-pyrazol-5-amine | 356.4 |
| 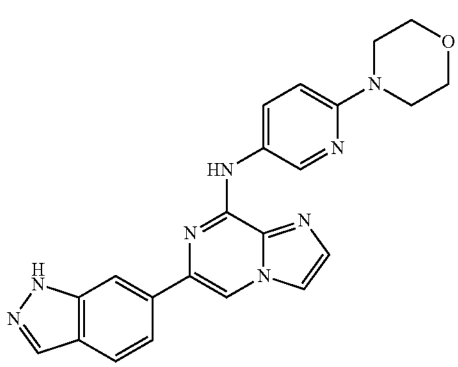 [SMILES: c1cn2cc(-c3ccc4cn[nH]c4c3)nc(Nc3ccc(N4CCOCC4)nc3)c2n1] | N-[6-(1H-indazol-6-yl)imidazo[1,2-a]pyrazin-8-yl]-6-(morpholin-4-yl)pyridin-3-amine | 413.2 |

-continued
| Structure | Name | [M + H]+ |
|---|---|---|
| 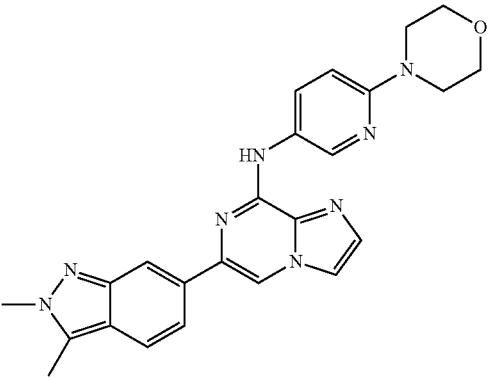 [SMILES: Cc1c2ccc(-c3cn4ccnc4c(Nc4ccc(N5CCOCC5)nc4)n3)cc2nn1C] | N-[6-(2,3-dimethyl-2H-indazol-6-yl)imidazo[1,2-a]pyrazin-8-yl]-6-(morpholin-4-yl)pyridin-3-amine | 441.2 |
| 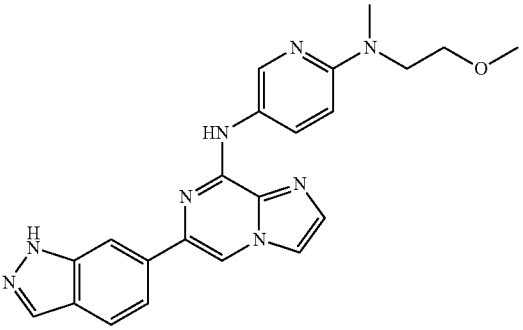 [SMILES: COCCN(C)c1ccc(Nc2nc(-c3ccc4cn[nH]c4c3)cn3ccnc23)cn1] | 5-N-[6-(1H-indazol-6-yl)imidazo[1,2-a]pyrazin-8-yl]-2-N-(2-methoxyethyl)-2-N-methylpyridine-2,5-diamine | 415.6 |
| 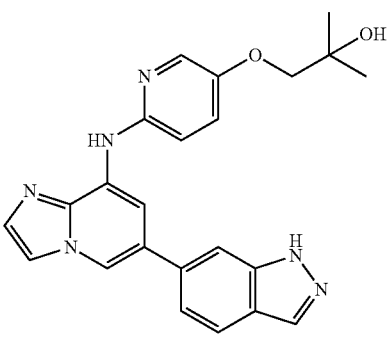 [SMILES: CC(C)(O)COc1ccc(Nc2cc(-c3ccc4cn[nH]c4c3)cn3ccnc23)nc1] | 1-[(6-{[6-(1H-indazol-6-yl)imidazo[1,2-a]pyridin-8-yl]amino}pyridin-3-yl)oxy]-2-methylpropan-2-ol | 415.6 |
| 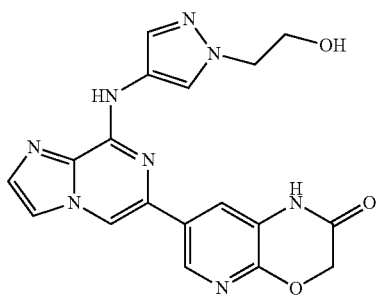 [SMILES: O=C1COc2ncc(-c3cn4ccnc4c(Nc4cnn(CCO)c4)n3)cc2N1] | 7-(8-{[1-(2-hydroxyethyl)-1H-pyrazol-4-yl]amino}imidazo[1,2-a]pyrazin-6-yl)-1H,2H,3H-pyrido[2,3-b][1,4]oxazin-2-one | 393.2 |

-continued

| Structure | Name | [M + H]+ |
|---|---|---|
| 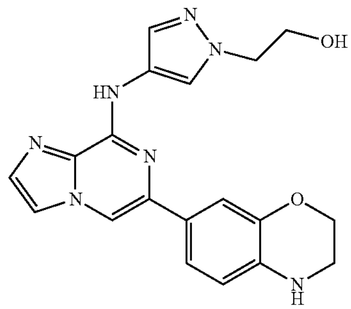 [SMILES: OCCn1cc(Nc2nc(-c3ccc4c(c3)OCCN4)cn3ccnc23)cn1] | 2-(4-{[6-(3,4-dihydro-2H-1,4-benzoxazin-7-yl)imidazo[1,2-a]pyrazin-8-yl]amino}-1H-pyrazol-1-yl)ethan-1-ol | 378.6 |
| 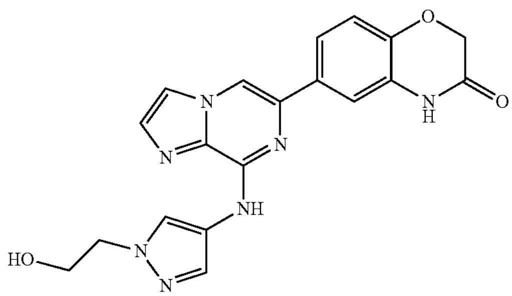 [SMILES: O=C1COc2ccc(-c3cn4ccnc4c(Nc4cnn(CCO)c4)n3)cc2N1] | 6-(8-{[1-(2-hydroxyethyl)-1H-pyrazol-4-yl]amino}imidazo[1,2-a]pyrazin-6-yl)-3,4-dihydro-2H-1,4-benzoxazin-3-one | 392.4 |
| 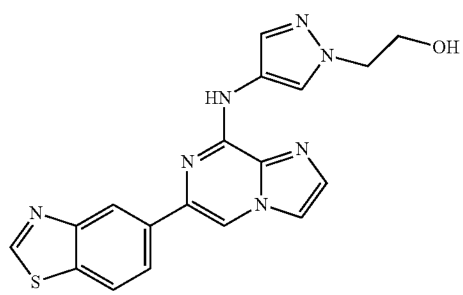 [SMILES: OCCn1cc(Nc2nc(-c3ccc4scnc4c3)cn3ccnc23)cn1] | 2-(4-{[6-(1,3-benzothiazol-5-yl)imidazo[1,2-a]pyrazin-8-yl]amino}-1H-pyrazol-1-yl)ethan-1-ol | 378.5 |
| 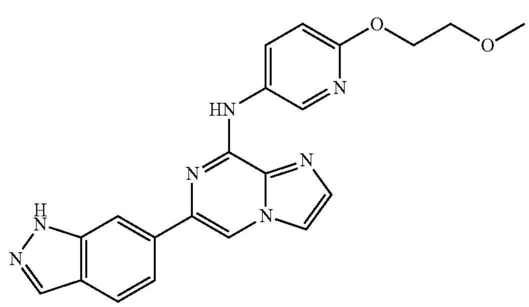 | N-[6-(1H-indazol-6-yl)imidazo[1,2-a]pyrazin-8-yl]-6-(2-methoxyethoxy)pyridin-3-amine | 402.4 |
| 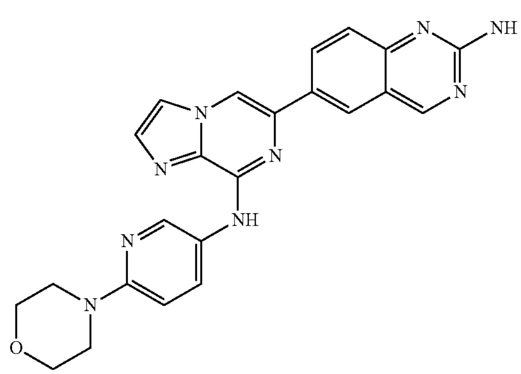 [SMILES: Nc1ncc2cc(-c3cn4ccnc4c(Nc4ccc(N5CCOCC5)nc4)n3)ccc2n1] | 6-(8-{[6-(morpholin-4-yl)pyridin-3-yl]amino}imidazo[1,2-a]pyrazin-6-yl)quinazolin-2-amine | 440.3 |

-continued

| Structure | Name | [M + H]+ |
|---|---|---|
| 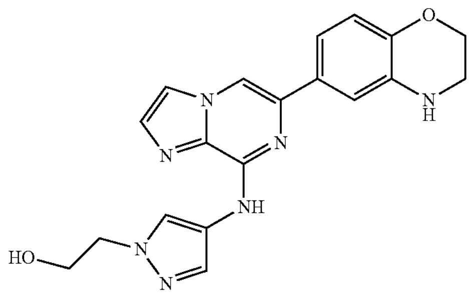 [SMILES: OCCn1cc(Nc2nc(-c3ccc4c(c3)NCCO4)cn3ccnc23)cn1] | 2-(4-{[6-(3,4-dihydro-2H-1,4-benzoxazin-6-yl)imidazo[1,2-a]pyrazin-8-yl]amino}-1H-pyrazol-1-yl)ethan-1-ol | 378.6 |
| 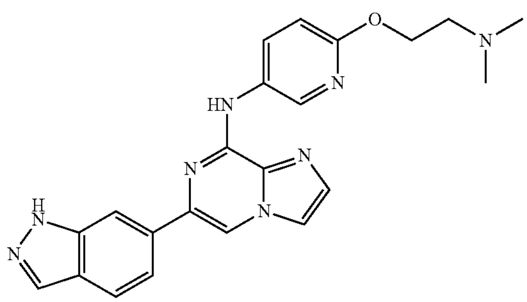 [SMILES: CN(C)CCOc1ccc(Nc2nc(-c3ccc4cn[nH]c4c3)cn3ccnc23)cn1] | 6-[2-(dimethylamino)ethoxy]-N-[6-(1H-indazol-6-yl)imidazo[1,2-a]pyrazin-8-yl]pyridin-3-amine | 415.4 |
| 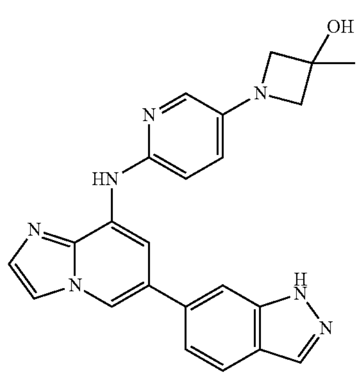 [SMILES: CC1(O)CN(c2ccc(Nc3cc(-c4ccc5cn[nH]c5c4)cn4ccnc34)nc2)C1] | 1-(6-{[6-(1H-indazol-6-yl)imidazo[1,2-a]pyridin-8-yl]amino}pyridin-3-yl)-3-methylazetidin-3-ol | 412.4 |
| 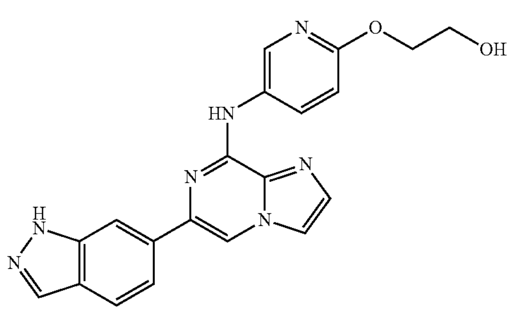 [SMILES: OCCOc1ccc(Nc2nc(-c3ccc4cn[nH]c4c3)cn3ccnc23)cn1] | 2-[(5-{[6-(1H-indazol-6-yl)imidazo[1,2-a]pyrazin-8-yl]amino}pyridin-2-yl)oxy]ethan-1-ol | 388.5 |

-continued

| Structure | Name | [M + H]+ |
|---|---|---|
| 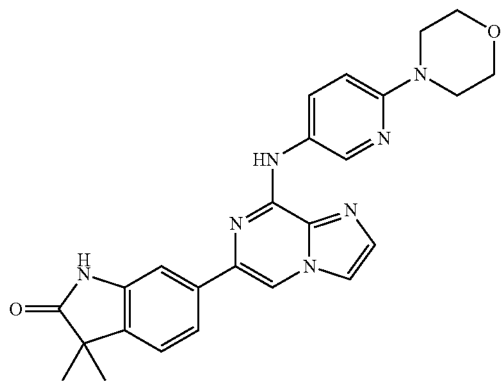 [SMILES: CC1(C)C(=O)Nc2cc(-c3cn4ccnc4c(Nc4ccc(N5CCOCC5)nc4)n3)ccc21] | 3,3-dimethyl-6-(8-{[6-(morpholin-4-yl)pyridin-3-yl]amino}imidazo[1,2-a]pyrazin-6-yl)-2,3-dihydro-1H-indol-2-one | 456.4 |
| 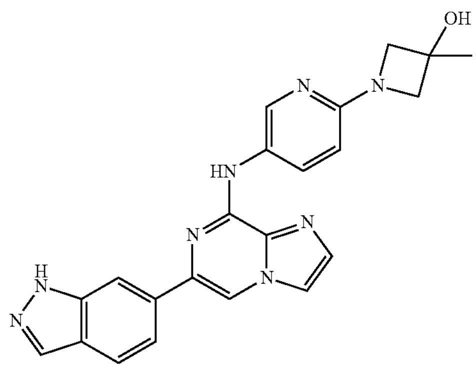 [SMILES: CC1(O)CN(c2ccc(Nc3nc(-c4ccc5cn[nH]c5c4)cn4ccnc34)cn2)C1] | 1-(5-{[6-(1H-indazol-6-yl)imidazo[1,2-a]pyrazin-8-yl]amino}pyridin-2-yl)-3-methylazetidin-3-ol | 413.4 |
| 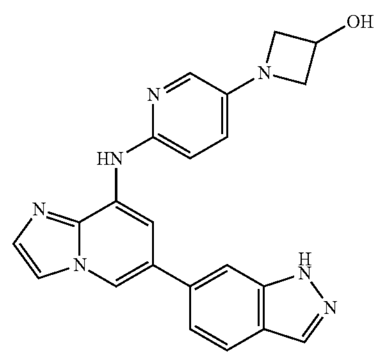 [SMILES: OC1CN(c2ccc(Nc3cc(-c4ccc5cn[nH]c5c4)cn4ccnc34)nc2)C1] | 1-(6-{[6-(1H-indazol-6-yl)imidazo[1,2-a]pyridin-8-yl]amino}pyridin-3-yl)azetidin-3-ol | 398.1 |
| 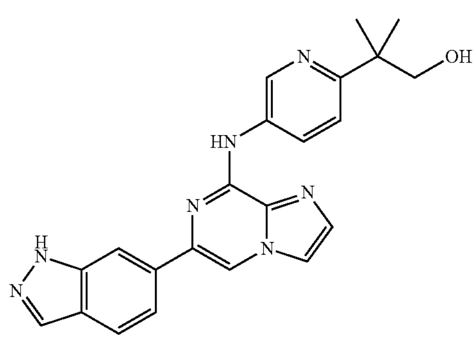 [SMILES: CC(C)(CO)c1ccc(Nc2nc(-c3ccc4cn[nH]c4c3)cn3ccnc23)cn1] | 2-(5-{[6-(1H-indazol-6-yl)imidazo[1,2-a]pyrazin-8-yl]amino}pyridin-2-yl)-2-methylpropan-1-ol | 400.2 |

| Structure | Name | [M + H]+ |
|---|---|---|
| 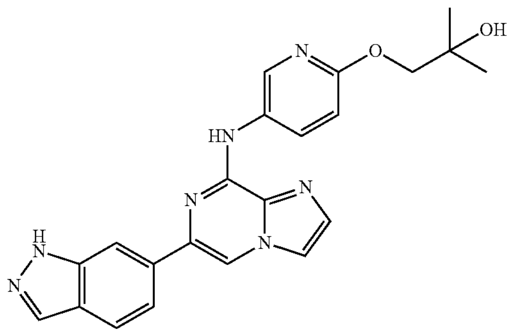 [SMILES: CC(C)(O)COc1ccc(Nc2nc(-c3ccc4cn[nH]c4c3)cn3ccnc23)cn1] | 1-[(5-{[6-(1H-indazol-6-yl)imidazo[1,2-a]pyrazin-8-yl]amino}pyridin-2-yl)oxy]-2-methylpropan-2-ol | 416.7 |
| 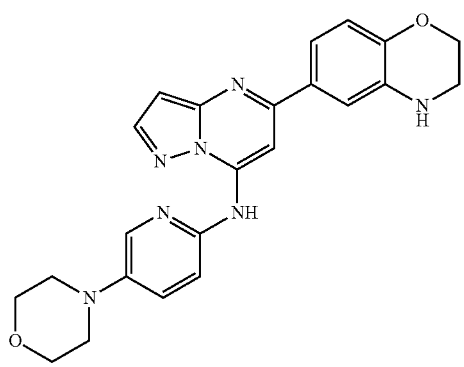 [SMILES: c1cc2nc(-c3ccc4c(c3)NCCO4)cc(Nc3ccc(N4CCOCC4)cn3)n2n1] | N-[5-(3,4-dihydro-2H-1,4-benzoxazin-6-yl)pyrazolo[1,5-a]pyrimidin-7-yl]-5-(morpholin-4-yl)pyridin-2-amine | 429.47 |
| 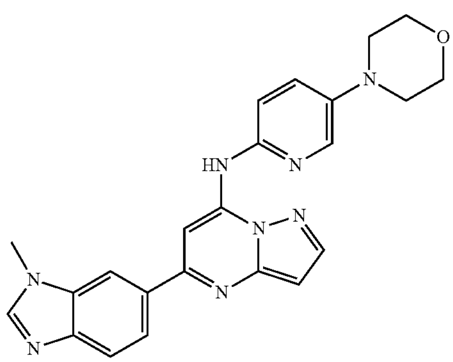 [SMILES: Cn1cnc2ccc(-c3cc(Nc4ccc(N5CCOCC5)cn4)n4nccc4n3)cc21] | N-[5-(1-methyl-1H-1,3-benzodiazol-6-yl)pyrazolo[1,5-a]pyrimidin-7-yl]-5-(morpholin-4-yl)pyridin-2-amine | 427.1 |
| 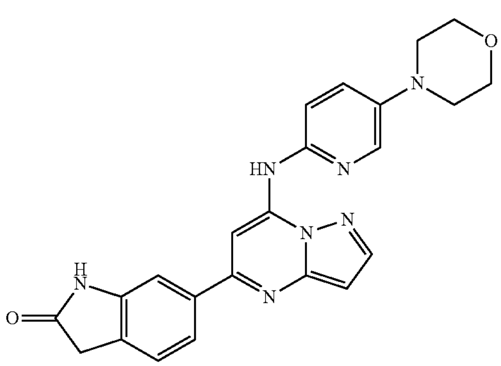 [SMILES: O=C1Cc2ccc(-c3cc(Nc4ccc(N5CCOCC5)cn4)n4nccc4n3)cc2N1] | 6-(7-{[5-(morpholin-4-yl)pyridin-2-yl]amino}pyrazolo[1,5-a]pyrimidin-5-yl)-2,3-dihydro-1H-indol-2-one | 428.1 |

-continued

| Structure | Name | [M + H]⁺ |
|---|---|---|
| 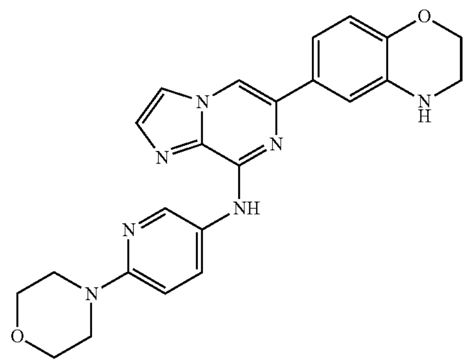 [SMILES: c1cn2cc(-c3ccc4c(c3)NCCO4)nc(Nc3ccc(N4CCOCC4)nc3)c2n1] | N-[6-(3,4-dihydro-2H-1,4-benzoxazin-6-yl)imidazo[1,2-a]pyrazin-8-yl]-6-(morpholin-4-yl)pyridin-3-amine | 430.3 |
| 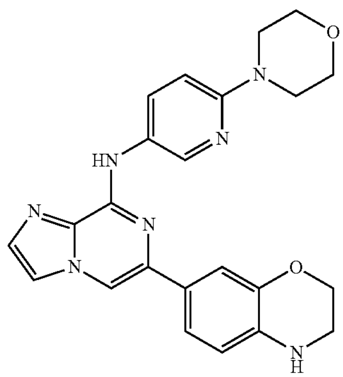 [SMILES: c1cn2cc(-c3ccc4c(c3)OCCN4)nc(Nc3ccc(N4CCOCC4)nc3)c2n1] | N-[6-(3,4-dihydro-2H-1,4-benzoxazin-7-yl)imidazo[1,2-a]pyrazin-8-yl]-6-(morpholin-4-yl)pyridin-3-amine | 430.3 |
| 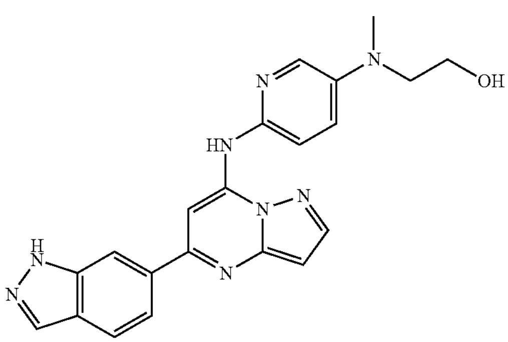 [SMILES: CN(CCO)c1ccc(Nc2cc(-c3ccc4cn[nH]c4c3)nc3ccnn23)nc1] | 2-[(6-{[5-(1H-indazol-6-yl)pyrazolo[1,5-a]pyrimidin-7-yl]amino}pyridin-3-yl)(methyl)amino]ethan-1-ol | 401.1 |
| 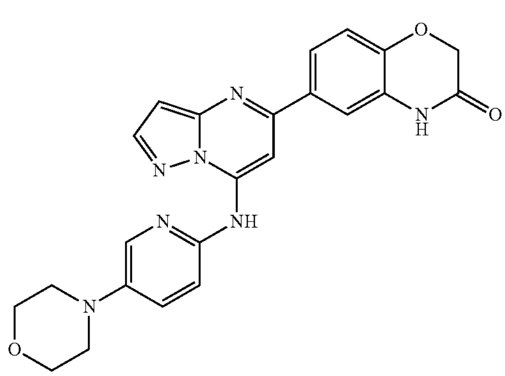 [SMILES: O=C1COc2ccc(-c3cc(Nc4ccc(N5CCOCC5)cn4)n4nccc4n3)cc2N1] | 6-(7-{[5-(morpholin-4-yl)pyridin-2-yl]amino}pyrazolo[1,5-a]pyrimidin-5-yl)-3,4-dihydro-2H-1,4-benzoxazin-3-one | 444.6 |

| Structure | Name | [M + H]⁺ |
|---|---|---|
| 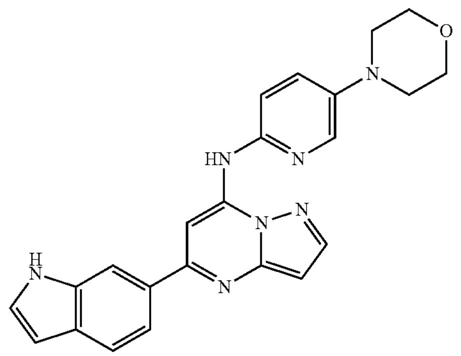 [SMILES: c1cc2nc(-c3ccc4cc[nH]c4c3)cc(Nc3ccc(N4CCOCC4)cn3)n2n1] | N-[5-(1H-indol-6-yl)pyrazolo[1,5-a]pyrimidin-7-yl]-5-(morpholin-4-yl)pyridin-2-amine | 412.4 |
| 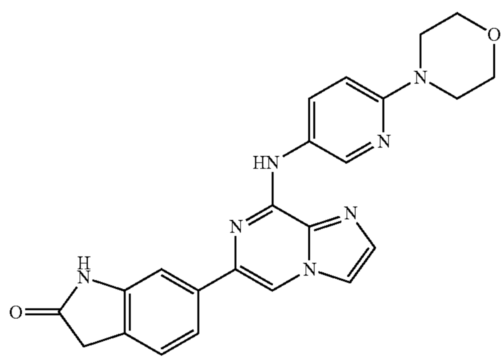 [SMILES: O=C1Cc2ccc(-c3cn4ccnc4c(Nc4ccc(N5CCOCC5)nc4)n3)cc2N1] | 6-(8-{[6-(morpholin-4-yl)pyridin-3-yl]amino}imidazo[1,2-a]pyrazin-6-yl)-2,3-dihydro-1H-indol-2-one | 428.2 |
| 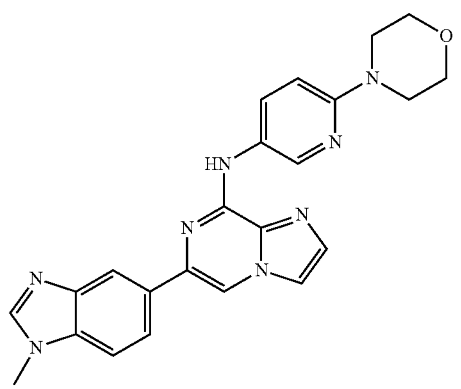 [SMILES: Cn1cnc2cc(-c3cn4ccnc4c(Nc4ccc(N5CCOCC5)nc4)n3)ccc21] | N-[6-(1-methyl-1H-1,3-benzodiazol-5-yl)imidazo[1,2-a]pyrazin-8-yl]-6-(morpholin-4-yl)pyridin-3-amine | 427 |
| 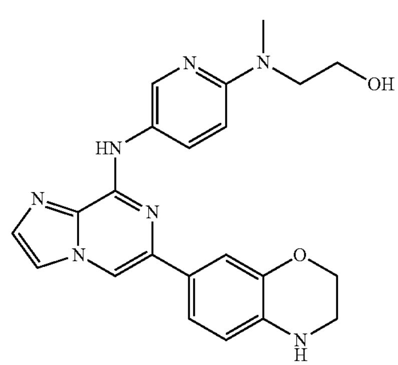 [SMILES: CN(CCO)c1ccc(Nc2nc(-c3ccc4c(c3)OCCN4)cn3ccnc23)cn1] | 2-[(5-{[6-(3,4-dihydro-2H-1,4-benzoxazin-7-yl)imidazo[1,2-a]pyrazin-8-yl]amino}pyridin-2-yl)(methyl)amino]ethan-1-ol | 418.6 |

-continued

| Structure | Name | [M + H]⁺ |
|---|---|---|
| 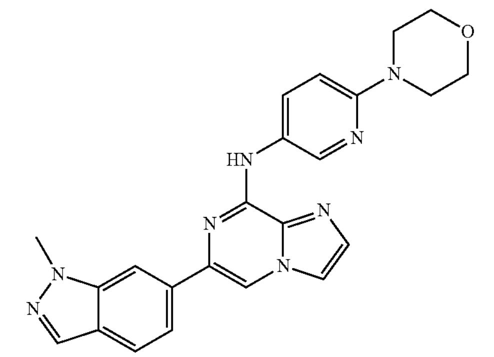 [SMILES: Cn1ncc2ccc(-c3cn4ccnc4c(Nc4ccc(N5CCOCC5)nc4)n3)cc21] | N-[6-(1-methyl-1H-1,3-benzodiazol-6-yl)imidazo[1,2-a]pyrazin-8-yl]-6-(morpholin-4-yl)pyridin-3-amine | 427 |
| 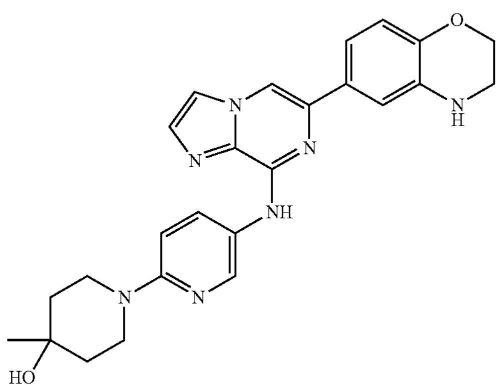 [SMILES: CC1(O)CCN(c2ccc(Nc3nc(-c4ccc5c(c4)NCCO5)cn4ccnc34)cn2)CC1] | 1-(5-{[6-(3,4-dihydro-2H-1,4-benzoxazin-6-yl)imidazo[1,2-a]pyrazin-8-yl]amino}pyridin-2-yl)-4-methylpiperidin-4-ol | 458.2 |
| 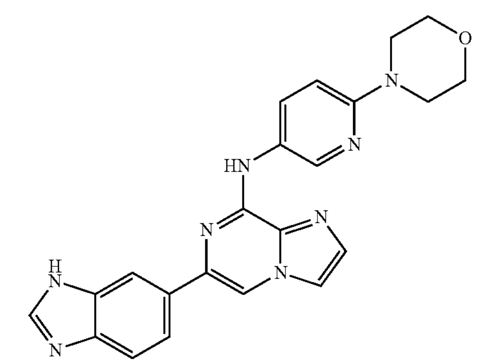 [SMILES: c1cn2cc(-c3ccc4nc[nH]c4c3)nc(Nc3ccc(N4CCOCC4)nc3)c2n1] | N-[6-(1H-1,3-benzodiazol-6-yl)imidazo[1,2-a]pyrazin-8-yl]-6-(morpholin-4-yl)pyridin-3-amine | 413.3 |
| 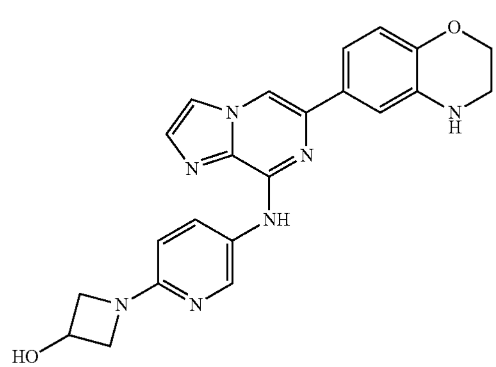 [SMILES: OC1CN(c2ccc(Nc3nc(-c4ccc5c(c4)NCCO5)cn4ccnc34)cn2)C1] | 1-(5-{[6-(3,4-dihydro-2H-1,4-benzoxazin-6-yl)imidazo[1,2-a]pyrazin-8-yl]amino}pyridin-2-yl)azetidin-3-ol | 416.7 |

-continued

| Structure | Name | [M + H]+ |
|---|---|---|
| 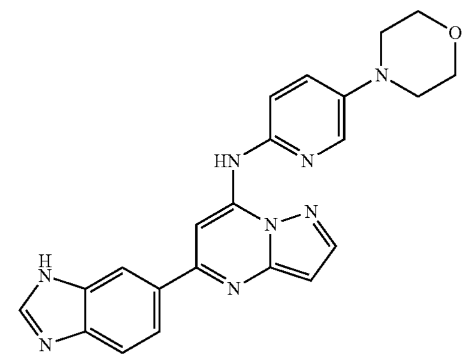 [SMILES: c1cc2nc(-c3ccc4nc[nH]c4c3)cc(Nc3ccc(N4CCOCC4)cn3)n2n1] | N-[5-(1H-1,3-benzodiazol-6-yl)pyrazolo[1,5-a]pyrimidin-7-yl]-5-(morpholin-4-yl)pyridin-2-amine | 413.4 |
| 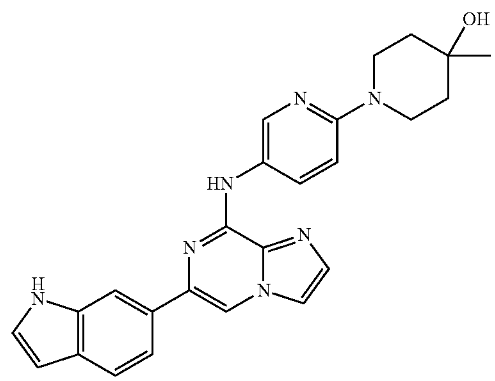 [SMILES: CC1(O)CCN(c2ccc(Nc3nc(-c4ccc5cc[nH]c5c4)cn4ccnc34)cn2)CC1] | 1-(5-{[6-(1H-indol-6-yl)imidazo[1,2-a]pyrazin-8-yl]amino}pyridin-2-yl)-4-methylpiperidin-4-ol | 440.3 |
| 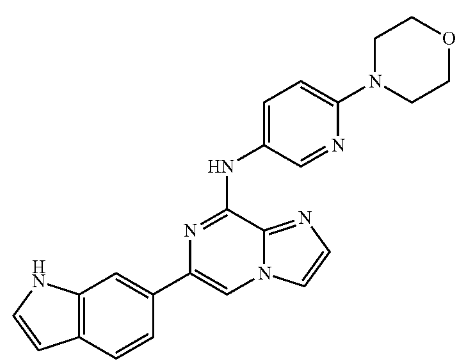 [SMILES: c1cn2cc(-c3ccc4cc[nH]c4c3)nc(Nc3ccc(N4CCOCC4)nc3)c2n1] | N-[6-(1H-indol-6-yl)imidazo[1,2-a]pyrazin-8-yl]-6-(morpholin-4-yl)pyridin-3-amine | 412.2 |
| 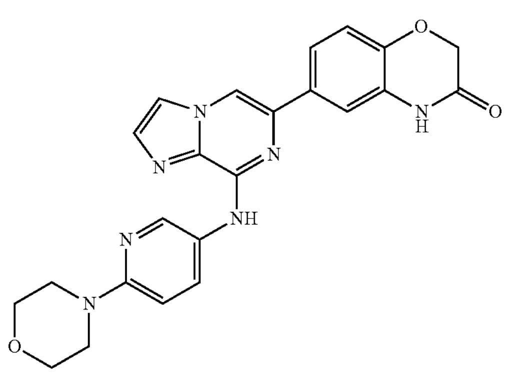 [SMILES: O=C1COc2ccc(-c3cn4ccnc4c(Nc4ccc(N5CCOCC5)nc4)n3)cc2N1] | 6-(8-{[6-(morpholin-4-yl)pyridin-3-yl]amino}imidazo[1,2-a]pyrazin-6-yl)-3,4-dihydro-2H-1,4-benzoxazin-3-one | 444.8 |

-continued

| Structure | Name | [M + H]⁺ |
|---|---|---|
| 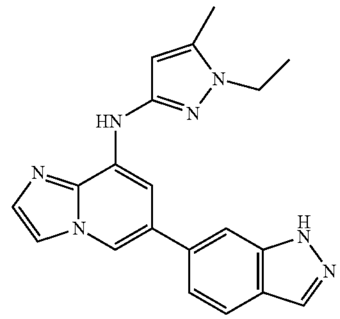 [SMILES: CCn1nc(Nc2cc(-c3ccc4cn[nH]c4c3)cn3ccnc23)cc1C] | 1-ethyl-N-[6-(1H-indazol-6-yl)imidazo[1,2-a]pyridin-8-yl]-5-methyl-1H-pyrazol-3-amine | 358.2 |
| 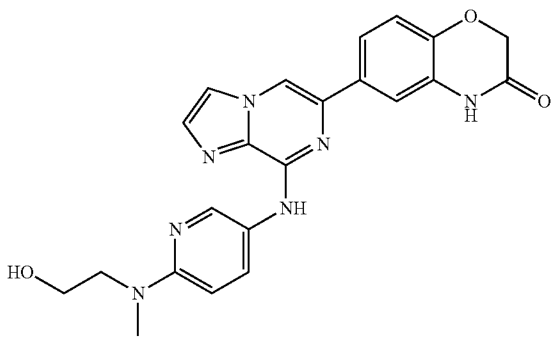 [SMILES: CN(CCO)c1ccc(Nc2nc(-c3ccc4c(c3)NC(=O)CO4)cn3ccnc23)cn1] | 6-[8-({6-[(2-hydroxyethyl)(methyl)amino]pyridin-3-yl}amino)imidazo[1,2-a]pyrazin-6-yl]-3,4-dihydro-2H-1,4-benzoxazin-3-one | 432.4 |
| 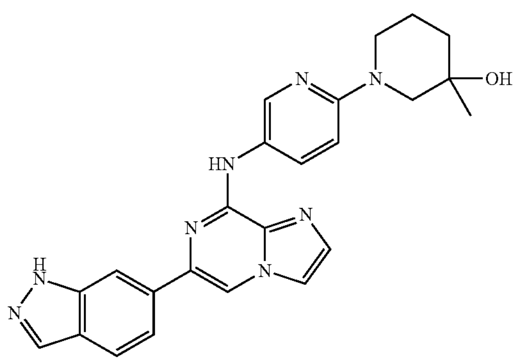 [SMILES: CC1(O)CCCN(c2ccc(Nc3nc(-c4ccc5cn[nH]c5c4)cn4ccnc34)cn2)C1] | 1-(5-{[6-(1H-indazol-6-yl)imidazo[1,2-a]pyrazin-8-yl]amino}pyridin-2-yl)-3-methylpiperidin-3-ol | 441.2 |
| 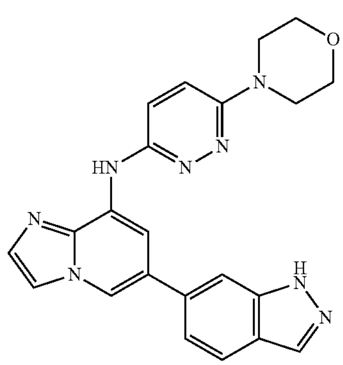 [SMILES: c1cn2cc(-c3ccc4cn[nH]c4c3)cc(Nc3ccc(N4CCOCC4)nn3)c2n1] | N-[6-(1H-indazol-6-yl)imidazo[1,2-a]pyridin-8-yl]-6-(morpholin-4-yl)pyridazin-3-amine | 413.4 |

-continued
| Structure | Name | [M + H]+ |
|---|---|---|
| 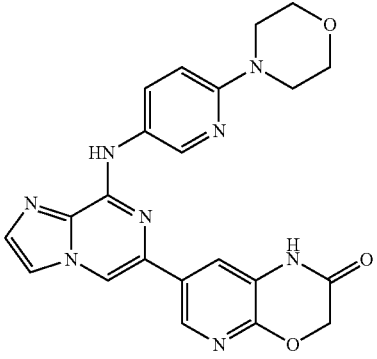 [SMILES: O=C1COc2ncc(-c3cn4ccnc4c(Nc4ccc(N5CCOCC5)nc4)n3)cc2N1] | 7-(8-{[6-(morpholin-4-yl)pyridin-3-yl]amino}imidazo[1,2-a]pyrazin-6-yl)-1H,2H,3H-pyrido[2,3-b][1,4]oxazin-2-one | 445.5 |
| 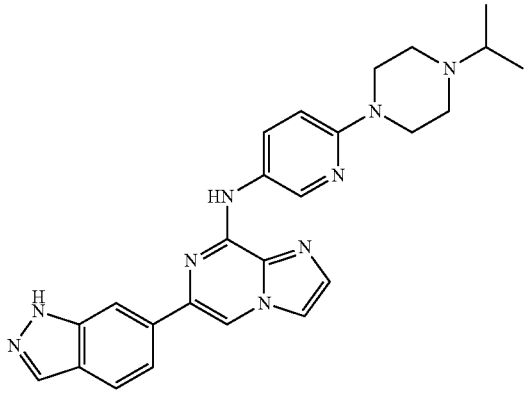 [SMILES: CC(C)N1CCN(c2ccc(Nc3nc(-c4ccc5cn[nH]c5c4)cn4ccnc34)cn2)CC1] | N-[6-(1H-indazol-6-yl)imidazo[1,2-a]pyrazin-8-yl]-6-[4-(propan-2-yl)piperazin-1-yl]pyridin-3-amine | 454.1 |
| 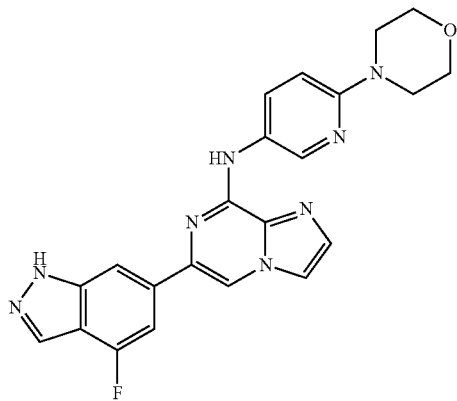 [SMILES: Fc1cc(-c2cn3ccnc3c(Nc3ccc(N4CCOCC4)nc3)n2)cc2[nH]ncc12] | N-[6-(4-fluoro-1H-indazol-6-yl)imidazo[1,2-a]pyrazin-8-yl]-6-(morpholin-4-yl)pyridin-3-amine | 431.4 |
| 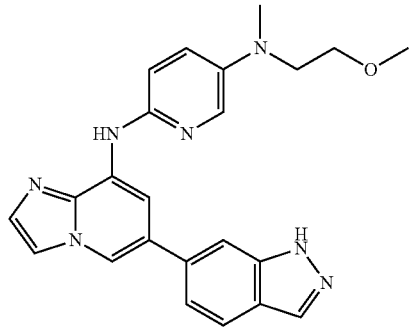 [SMILES: COCCN(C)c1ccc(Nc2cc(-c3ccc4cn[nH]c4c3)cn3ccnc23)nc1] | 2-N-[6-(1H-indazol-6-yl)imidazo[1,2-a]pyridin-8-yl]-5-N-(2-methoxyethyl)-5-N-methylpyridine-2,5-diamine | 414.2 |

-continued

| Structure | Name | [M + H]+ |
|---|---|---|
| 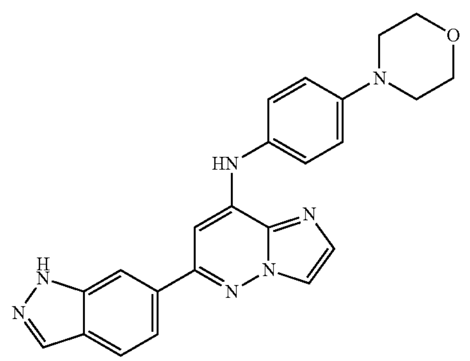 [SMILES: c1cn2nc(-c3ccc4cn[nH]c4c3)cc(Nc3ccc(N4CCOCC4)cc3)c2n1] | 6-(1H-benzo[d]imidazol-6-yl)-N-(5-morpholinopyridin-2-yl)imidazo[1,2-b]pyridazin-8-amine | 413.4 |
| 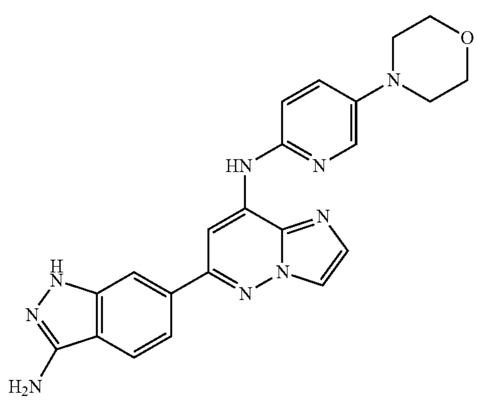 [SMILES: Nc1n[nH]c2cc(-c3cc(Nc4ccc(N5CCOCC5)cn4)c4nccn4n3)ccc12] | 6-(3-amino-1H-indazol-6-yl)-N-(5-morpholinopyridin-2-yl)imidazo[1,2-b]pyridazin-8-amine | 428.1 |
| 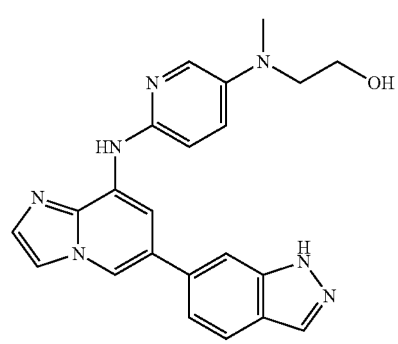 [SMILES: CN(CCO)c1ccc(Nc2cc(-c3ccc4cn[nH]c4c3)cn3ccnc23)nc1] | 2-[(6-{[6-(1H-indazol-6-yl)imidazo[1,2-a]pyridin-8-yl]amino}pyridin-3-yl)(methyl)amino]ethan-1-ol | 400.2 |
| 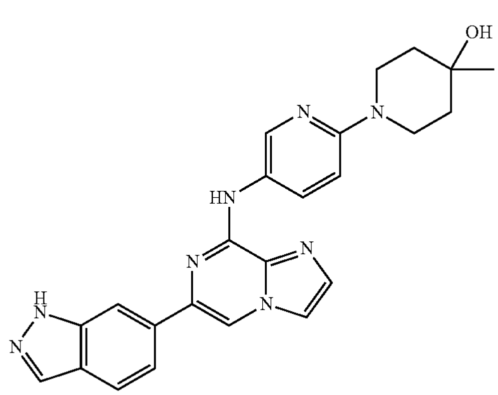 [SMILES: CC1(O)CCN(c2ccc(Nc3nc(-c4ccc5cn[nH]c5c4)cn4ccnc34)cn2)CC1] | 1-(5-{[6-(1H-indazol-6-yl)imidazo[1,2-a]pyridin-8-yl]amino}pyridin-2-yl)-4-methylpiperidin-4-ol | 441.2 |

-continued

| Structure | Name | [M + H]⁺ |
|---|---|---|
| 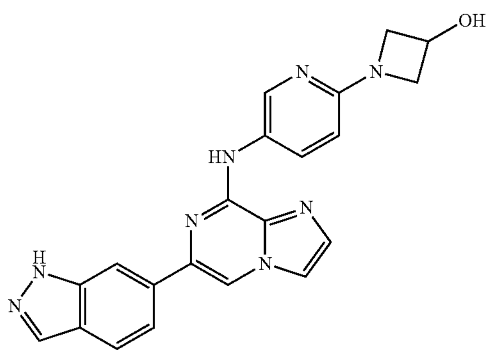 [SMILES: OC1CN(c2ccc(Nc3nc(-c4ccc5cn[nH]c5c4)cn4ccnc34)cn2)C1] | 1-(5-{[6-(1H-indazol-6-yl)imidazo[1,2-a]pyrazin-8-yl]amino}pyridin-2-yl)azetidin-3-ol | 399.3 |
| 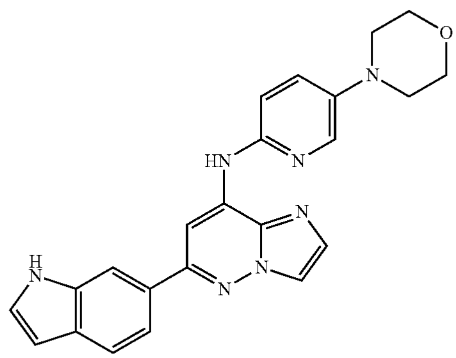 [SMILES: c1cn2nc(-c3ccc4cc[nH]c4c3)cc(Nc3ccc(N4CCOCC4)cn3)c2n1] | 6-(1H-indol-6-yl)-N-(5-morpholinopyridin-2-yl)imidazo[1,2-b]pyridazin-8-amine | 412.3 |
| 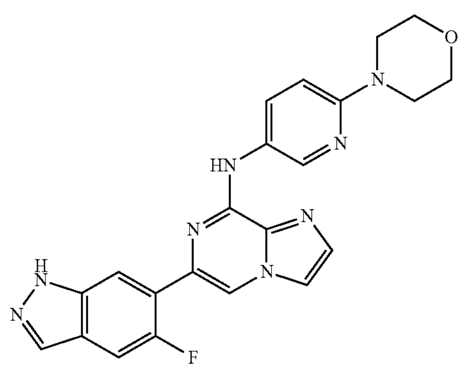 [SMILES: Fc1cc2cn[nH]c2cc1-c1cn2ccnc2c(Nc2ccc(N3CCOCC3)nc2)n1] | N-[6-(5-fluoro-1H-indazol-6-yl)imidazo[1,2-a]pyrazin-8-yl]-6-(morpholin-4-yl)pyridin-3-amine | 431.5 |
| 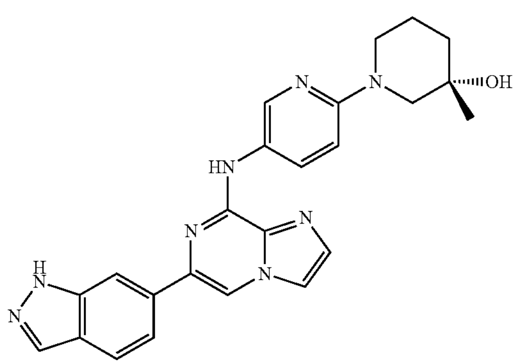 [SMILES: C[C@]1(O)CCCN(c2ccc(Nc3nc(-c4ccc5cn[nH]c5c4)cn4ccnc34)cn2)C1] | (3S)-1-(5-{[6-(1H-indazol-6-yl)imidazo[1,2-a]pyrazin-8-yl]amino}pyridin-2-yl)-3-methylpiperidin-3-ol | 441.2 |

| Structure | Name | [M + H]+ |
|---|---|---|
| 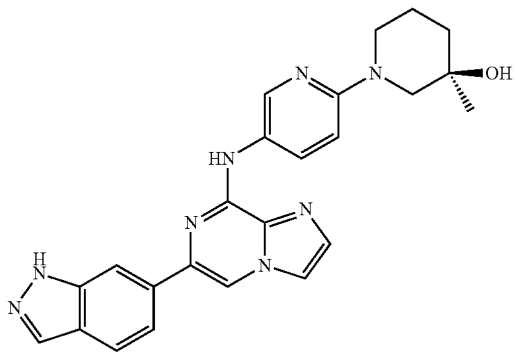 [SMILES: C[C@@]1(O)CCCN(c2ccc(Nc3nc(-c4ccc5cn[nH]c5c4)cn4ccnc34)cn2)C1] | (3R)-1-(5-{[6-(1H-indazol-6-yl)imidazo[1,2-a]pyrazin-8-yl]amino}pyridin-2-yl)-3-methylpiperidin-3-ol | 441.2 |
| 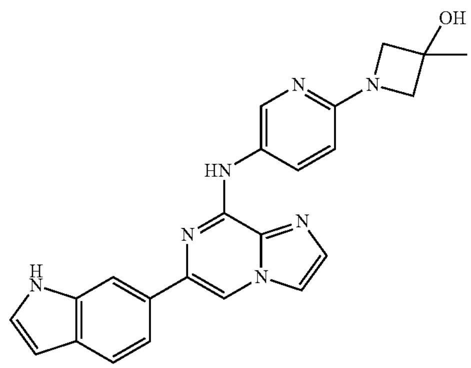 [SMILES: CC1(O)CN(c2ccc(Nc3nc(-c4ccc5cc[nH]c5c4)cn4ccnc34)cn2)C1] | 1-(5-{[6-(1H-indol-6-yl)imidazo[1,2-a]pyrazin-8-yl]amino}pyridin-2-yl)-3-methylazetidin-3-ol | 412.4 |
| 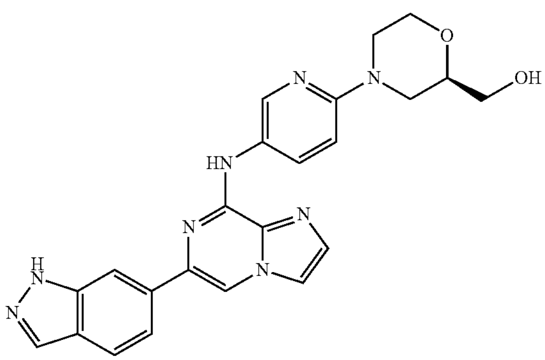 [SMILES: OC[C@H]1CN(c2ccc(Nc3nc(-c4ccc5cn[nH]c5c4)cn4ccnc34)cn2)CCO1] | [(2R)-4-(5-{[6-(1H-indazol-6-yl)imidazo[1,2-a]pyrazin-8-yl]amino}pyridin-2-yl)morpholin-2-yl]methanol | 443.5 |
| 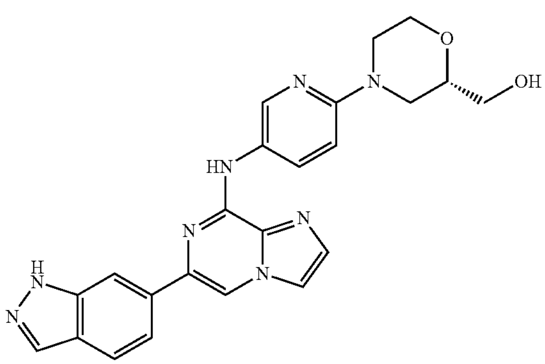 [SMILES: OC[C@@H]1CN(c2ccc(Nc3nc(-c4ccc5cn[nH]c5c4)cn4ccnc34)cn2)CCO1] | [(2S)-4-(5-{[6-(1H-indazol-6-yl)imidazo[1,2-a]pyrazin-8-yl]amino}pyridin-2-yl)morpholin-2-yl]methanol | 443.4 |

-continued

| Structure | Name | [M + H]⁺ |
|---|---|---|
| 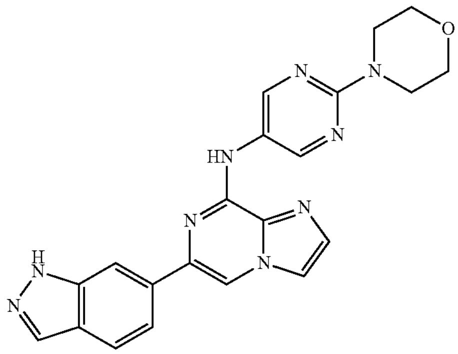 [SMILES: c1cn2cc(-c3ccc4cn[nH]c4c3)nc(Nc3cnc(N4CCOCC4)nc3)c2n1] | N-[6-(1H-indazol-6-yl)imidazo[1,2-a]pyrazin-8-yl]-2-(morpholin-4-yl)pyrimidin-5-amine | 414.5 |
| 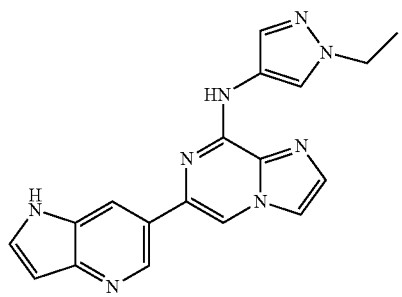 [SMILES: CCn1cc(Nc2nc(-c3cnc4cc[nH]c4c3)cn3ccnc23)cn1] | 1-ethyl-N-(6-{1H-pyrrolo[3,2-b]pyridin-6-yl}imidazo[1,2-a]pyrazin-8-yl)-1H-pyrazol-4-amine | 344.9 |
| 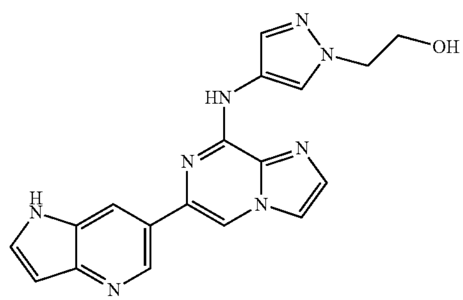 [SMILES: OCCn1cc(Nc2nc(-c3cnc4cc[nH]c4c3)cn3ccnc23)cn1] | 2-{4-[(6-{1H-pyrrolo[3,2-b]pyridin-6-yl}imidazo[1,2-a]pyrazin-8-yl)amino]-1H-pyrazol-1-yl}ethan-1-ol | 361.6 |

Example 3

Biochemical Syk Assay

A generalized procedure for one standard biochemical Syk Kinase Assay that can be used to test compounds disclosed in this application is as follows.

A master mix minus Syk enzyme is prepared containing 1× Cell Signaling kinase buffer (25 mM Tris-HCl, pH 7.5, 5 mM beta-glycerophosphate, 2 mM dithiothreitol, 0.1 mM $Na_3VO_4$, 10 mM $MgCl_2$), 0.5 µM Promega PTK Biotinylated peptide substrate 1, 0.01% casein, 0.01% Triton-X100, and 0.25% glycerol. A master mix plus Syk enzyme is prepared containing 1× Cell Signaling kinase buffer, 0.5 µM PTK Biotinylated peptide substrate 1, 0.01% casein, 0.01% Triton-X100, 0.25% glycerol and 0.4 ng/well Syk enzyme. Syk enzyme is purchased from Cell Signaling Technologies, expressed in baculovirus and is an N-terminally GST-tagged full length human wildtype Syk (accession number NM-00377). The Syk protein was purified in one step using glutathione-agarose. The purity of the final protein preparation was assessed by SDS-PAGE and Coomassie staining. A solution of 200 µM ATP is prepared in water and adjusted to pH 7.4 with 1N NaOH. A quantity of 1.25 µL of compounds in 5% DMSO is transferred to a 96-well ½ area Costar polystyrene plate Compounds are tested singly and with an 11-point dose-responsive curve (starting concentration is 10-1 µM; 1:2 dilution). A quantity of 18.75 µL of master mix minus enzyme (as a negative control) and master mix plus enzyme is transferred to appropriate wells in 96-well ½ area costar polystyrene plate. 5 µL of 200 µM ATP is added to that mixture in the 96-well ½ area Costar polystyrene plate for final ATP concentration of 40 µM. The reaction is allowed to incubate for 1 hour at room temperature. The reaction is stopped with Perkin Elmer 1× detection buffer containing 30 mM EDTA, 80 nM SA-APC, and 4 nM PT66 Ab. The plate is read using time-resolved fluorescence with a Perkin Elmer Envision using excitation filter 330 nm, emission filter 665 nm, and $2^{nd}$ emission filter 615 nm. $IC_{50}$ values are subsequently calculated using a linear regression algorithm.

Example 4

Ramos Cell pBLNK(Y96) Assay

Another generalized procedure for a standard cellular Syk Kinase Assay that can be used to test compounds disclosed in this application is as follows.

Ramos cells are serum starved at $2 \times 10^6$ cells/ml in serum-free RPMI for 1 hour in an upright T175 Falcon TC flask. Cells are centrifuged (1100 rpm×5 min) and incubated at a density of $0.5 \times 10^7$ cells/ml in the presence of test compound or DMSO controls for 1 hr at 37° C. Cells are then stimulated by incubating with 10 µg/ml anti-human IgM F(ab)$_2$ for 5 minutes at 37° C. Cells are pelleted, lysed in 40 ul cell lysis buffer, and mixed with Invitrogen SDS-PAGE loading buffer. 20 ul of cell lysate for each sample are subject to SDS-PAGE and western blotting with anti-phos-phoBLNK(Tyr96) antibody (Cell Signaling Technology #3601) to assess Syk activity and anti-Syk antibody (BD Transduction Labs #611116) to control for total protein load in each lysate. The images are detected using fluorescent secondary detection systems and the LiCor Odyssey software.

Example 5

B-Cell Proliferation Assay

A generalized procedure for a standard cellular B-cell proliferation assay that can be used to test compounds disclosed in this application is as follows.

B-cells are purified from spleens of 8-16 week old Balb/c mice using a B-cell isolation kit (Miltenyi Biotech, Cat #130-090-862). Test compounds are diluted in 0.25% DMSO and incubated with $2.5 \times 10^5$ purified mouse splenic B-cells for 30 min prior to addition of 10 µg/ml of an anti-mouse IgM antibody (Southern Biotechnology Associates Cat #1022-01) in a final volume of 100 µl. Following 24 hr incubation, 1 µCi $^3$H-thymidine is added and plates are incubated an additional 36 hr prior to harvest using the manufacturer's protocol for SPA[$^3$H] thymidine uptake assay system (Amersham Biosciences # RPNQ 0130). SPA-bead based fluorescence is counted in a microbeta counter (Wallace Triplex 1450, Perkin Elmer).

Example 6

T Cell Proliferation Assay

A generalized procedure for a standard T cell proliferation assay that can be used to test compounds disclosed in this application is as follows.

T cells are purified from spleens of 8-16 week old Balb/c mice using a Pan T cell isolation kit (Miltenyi Biotech, Cat #130-090-861). Test compounds are diluted in 0.25% DMSO and incubated with $2.5 \times 10^5$ purified mouse splenic T cells in a final volume of 100 µl in flat clear bottom plates precoated for 90 min at 37° C. with 10 µg/ml each of anti-CD3 (BD #553057) and anti-CD28 (BD #553294) antibodies. Following 24 hr incubation, 1 µCi $^3$H-thymidine is added and plates incubated an additional 36 hr prior to harvest using the manufacturer's protocol for SPA[$^3$H] thymidine uptake assay system (Amersham Biosciences # RPNQ 0130). SPA-bead based fluorescence was counted in a microbeta counter (Wallace Triplex 1450, Perkin Elmer).

Example 7

CD69 Inhibition Assay

A generalized procedure for a standard assay for the inhibition of B cell activity that can be used to test compounds disclosed in this application is as follows.

Total mouse splenocytes are purified from spleens of 8-16 week old Balb/c mice by red blood cell lysis (BD Pharmingen #555899). Testing compounds are diluted to 0.5% DMSO and incubated with $1.25 \times 10^6$ splenocytes in a final volume of 200 µl in flat clear bottom plates (Falcon 353072) for 60 min at 37° C. Cells are then stimulated with the addition of 15 µg/ml IgM (Jackson ImmunoResearch 115-006-020), and incubated for 16 hr at 37° C., 5% $CO_2$. Following the 16 hr incubation, cells are transferred to conical bottom clear 96-well plates and pelleted by centrifugation at 1200×g×5 min. Cells are preblocked by CD16/CD32 (BD Pharmingen #553142), followed by triple staining with CD19-FITC (BD Pharmingen #553785), CD69-PE (BD Pharmingen #553237), and 7AAD (BD Pharmingen #51-68981E). Cells are sorted on a BD FACSCalibur and gated on the CD19$^+$/7AAD$^-$ population. The levels of CD69 surface expression on the gated population is measured versus test compound concentration.

Example 8

BMMC Degranulation

A generalized procedure for a standard assay for bone-marrow derived mouse mast cell (BMMC) degranulation that can be used to test compounds disclosed in this application is as follows.

Bone-marrow derived mast cells were cultured for >4 weeks with IL-3 (10 ng/ml) and SCF (10 ng/ml). The cells were determined to be >90% cKit$^+$/FceRI$^+$ by FACS analysis at the time of use. Cells ($6 \times 10^7$ cells/50 ml) were serum-starved in a T150 tissue culture flask for 16 h in the absence of IL-3 and SCF containing IgEa-DNP at 1 ug/ml. Overnight sensitized cells are washed twice in Tyrodes buffer and resuspended to $5 \times 10^6$ cells/ml. $5 \times 10^5$ cells (100 ul) are plated in a 96 well microtiter plate (Falcon 353072) and test compounds are serially diluted to a final concentration 0.25% DMSO in the plate for 1 hr at 37° C., 5% $CO_2$. Wells are treated with a DNP-BSA antigen challenge (50 ng/ml) and incubated for and additional 30 min at 37° C. Supernatants are assayed for hexosamimidase release versus control wells. Cell pellets are simultaneously lysed and assed for total hexosamimidase release to calculate specific release. Dose-response curves are generated using 4-parameter logistical fit and IC50s calculated.

Example 9

Passive Cutaneous Anaphylaxis (PCA)

The following is a procedure for a standard PCA model used for measuring in vivo IgE anti-DNP Ab sensitization and DNP-BSA antigen for triggering mast cell degranulation and release of immune regulators that cause acute vessel permeability monitored by Evan's blue dye into the inflamed area in the mouse ear.

Reagents: Anti-DNP IgE: is supplied as 1.2 mg/ml in a phosphate buffered solution with BSA for additional protein and azide for sterility. This is diluted 1:100 in sterile PBS as a 12 ug/ml working stock that can be further diluted in PBS to the appropriate concentration for injection. A further 1:5 dilution give a final 1:500 solution at 2.4 ng/ul. (10 ul/ear=24 ng). Sterile PBS alone will be used as a negative control.—DNP-BSA: will be made up at 4 mg/ml in sterile ddH$_2$O and stored at 40° C. solution. It is further diluted 1:1 with sterile saline prior to use. This solution or a further dilution in saline is diluted 1:1 with 2% Evan's Blue in sterile saline that has been filtered though 0.02 um filter and refiltered prior to injection. For these experiments a final solution of 0.5 mg/ml of DNP-BSA in 1% Evans blue can be used. Tail vein injections will be held constant at 200 ul=100 ug in 1% Evan's Blue.—Evan's blue dye: A 2% stock in saline will be sterile filtered and diluted 1:1 with DNP-BSA saline solution for final concentration of 1% for injection.

General PCA Protocol Using Intradermal Ear Sensitization

1) On d0, animals, anesthetized with isofluorine, are passively sensitized by intradermal injections of IgE anti-DNP using a 29-gauge insulin syringe. By convention, the right ear receives 10 ul intradermal injection of anti-DNP IgE while the left ear receives PBS. 2) 20 hr post sensitization, antigen challenge is administered by tail i.v. injection of DNP-BSA in 200 ul of 1% Evan's blue dye solution in saline. Tails are immersed in warm water prior to iv injection to improve success. 3) 30 minutes to 2 hr prior to this antigen challenge, drug is delivered sc or po in 10% EtOH/20% cremaphor/70% saline. 4) Animals are sacrifice by $CO_2$ inhalation 30-60 min post antigen challenge and ears are removed for extraction of Evan's blue dye in 500 ul of formamide overnight at 65° C. 5) Blood is obtained by cardiac puncture just prior to final cervical dislocation and processed for plasma to provide PK analysis. 6) Evan's blue dye is quantified by reading absorbency of 200 ul of extracted solution in microtiter plates at 620 nm.

Study Design of Experiment

Each animal has one anti-DNP IgE sensitized ear (right ear by convention) and one PBS control ear (left ear by convention). Groups 1-8: represent the vehicle and compound testing arms; Group 9: represents the non-antigen negative control; Group 10: represents the non-sensitized challenged negative control; Group 11: represents the non-antigen challenged, non-sensitized negative control group (Groups 9-11 represent negative controls for background levels only and require only minimal number of animals per group.)

The compounds disclosed in the examples above were tested in the Syk biochemical assay described herein (Example 3) and certain of those compounds exhibited an $IC_{50}$ value less than or equal to 1 micromolar. Certain of those compounds exhibited an $IC_{50}$ value less than or equal to 100 nM. Certain of those compounds exhibited an $IC_{50}$ value less than or equal to 10 nM. Certain of those compounds exhibited an $IC_{50}$ value less than or equal to 1 nM.

Some of the compounds disclosed in Example 2 were tested in the B-cell proliferation assay (as described in Example 5) and exhibited an $IC_{50}$ value less than or equal to 10 micromolar. Certain of those compounds exhibited an $IC_{50}$ value less than or equal to 1 micromolar.

Certain of those compounds did not inhibit T-cell proliferation and had $IC_{50}$ values greater than or equal to 5 micromolar when assayed under conditions described herein (as described in Example 6).

Certain compounds described herein exhibited $IC_{50}$ values for inhibition of T-cell proliferation that were at least 3-fold, and in some instances 5-fold, greater than the $IC_{50}$ values of those compounds for inhibition of B-cell proliferation.

Some of the compounds described herein were tested in an assay for inhibition of B cell activity (under the conditions described in example 7), and exhibited an $IC_{50}$ value less than or equal to 10 micromolar. Certain of those compounds exhibited an $IC_{50}$ value less than or equal to 1 micromolar.

Some of the compounds disclosed in described herein exhibited both biochemical and cell-based activity. For example, some of the compounds described herein exhibited an $IC_{50}$ value less than or equal to 10 micromolar in the Syk biochemical assay described herein (Example 3) and an $IC_{50}$ value less than or equal to 10 micromolar in at least one of the cell-based assays (other than the T-cell assay) described herein (Examples 4, 5, 7 or 8). Certain of those compounds exhibited an $IC_{50}$ value less than or equal to 1 micromolar in the Syk biochemical assay described herein (Example 4) and an $IC_{50}$ value less than or equal to 10 micromolar in at least one of the cell-based assays (other than the T-cell assay) described herein (Examples 4, 5, 7 or 8). Certain of those compounds exhibited an $IC_{50}$ value less than or equal to 0.1 micromolar and an $IC_{50}$ value less than or equal to 10 micromolar in at least one of the cell-based assays (other than the T-cell assay) described herein (Examples 4, 5, 7 or 8).

While some embodiments have been shown and described, various modifications and substitutions may be made thereto without departing from the spirit and scope of the invention. For example, for claim construction purposes, it is not intended that the claims set forth hereinafter be construed in any way narrower than the literal language thereof, and it is thus not intended that exemplary embodiments from the specification be read into the claims. Accordingly, it is to be understood that the present invention has been described by way of illustration and not limitations on the scope of the claims.

What is claimed:

1. At least one chemical entity of Formula I:

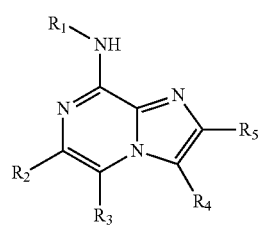

or a pharmaceutically acceptable salt thereof, wherein
$R_1$ is pyridinyl;
$R_2$ is a 5- to 6-membered aromatic carbocyclic ring fused to (i) a 5- to 7-membered heterocycloalkyl ring or to (ii) a 5- to 7-membered heteroaryl ring;
wherein $R_1$ and $R_2$ are each independently and optionally substituted with one or more substituent groups independently chosen from —$R^a$, —$OR^b$, —$O(C_1$-$C_2$ alkyl) O—, —$SR^b$, guanidine, guanidine wherein one or more of the guanidine hydrogens are replaced with $C_1$-$C_6$ alkyl, —$NR^bR^c$, halo, cyano, oxo (as a substituent for heterocycloalkyl), nitro, —$COR^b$, —$CO_2R^b$, —$CONR^bR^c$, —$OCOR^b$, —$OCO_2R^a$, —$OCONR^bR^c$, —$NR^cCOR^b$, —$NR^cCO_2R^a$, —$NR^cCONR^bR^c$, —$SOR^a$, —$SO_2R^a$, —$SO_2NR^bR^c$, and —$NR^cSO_2R^a$;
wherein $R^a$ is chosen from $C_1$-$C_6$ alkyl, $C_3$-$C_6$ cycloalkyl, aryl, heterocycloalkyl, and heteroaryl;
wherein $R^b$ is chosen from hydrogen, $C_1$-$C_6$ alkyl, aryl, and heteroaryl; and
wherein $R^c$ is chosen from hydrogen and $C_1$-$C_4$ alkyl; or wherein $R^b$ and $R^c$, and the nitrogen to which they are attached, form a heterocycloalkyl group;
wherein $R^a$, $R^b$, and $R^c$ are each independently and optionally substituted with one or more substituent groups independently chosen from $C_1$-$C_4$ alkyl, $C_3$-$C_6$ cycloalkyl, aryl, heteroaryl, aryl-$C_1$-$C_4$ alkyl-, heteroaryl-$C_1$-$C_4$ alkyl-, $C_1$-$C_4$ haloalkyl-, —$OC_1$-$C_4$ alkyl, —$OC_1$-$C_4$ alkylphenyl, —$C_1$-$C_4$ alkyl-OH, —$C_1$-$C_4$ alkyl-O—$C_1$-$C_4$ alkyl, —$OC_1$-$C_4$ haloalkyl, halo, —OH, —$NH_2$, —$C_1$-$C_4$ alkyl-$NH_2$, —$N(C_1$-$C_4$ alkyl)($C_1$-$C_4$ alkyl), —$NH(C_1$-$C_4$ alkyl), —$N(C_1$-$C_4$ alkyl)($C_1$-$C_4$ alkylphenyl), —$NH(C_1$-$C_4$ alkylphenyl), cyano, nitro, oxo (as a substituent for heteroaryl), —$CO_2H$, —$C(O)OC_1$-$C_4$ alkyl, —$CON(C_1$-$C_4$ alkyl)($C_1$-$C_4$ alkyl), —$CONH(C_1$-$C_4$ alkyl), —$CONH_2$, —$NHC(O)(C_1$-$C_4$ alkyl), —$NHC(O)$(phenyl), —$N(C_1$-$C_4$ alkyl)$C(O)(C_1$-$C_4$ alkyl), —$N(C_1$-$C_4$ alkyl)$C(O)$(phenyl), —$C(O)C_1$-$C_4$ alkyl, —$C(O)C_1$-$C_4$ phenyl, —$C(O)C_1$-$C_4$ haloalkyl, —$OC(O)C_1$-$C_4$ alkyl, —$SO_2$($C_1$-$C_4$ alkyl), —$SO_2$(phenyl), —$SO_2(C_1$-$C_4$ haloalkyl), —$SO_2NH_2$, —$SO_2NH(C_1$-$C_4$ alkyl), —$SO_2NH$(phenyl), —$NHSO_2(C_1$-$C_4$ alkyl), —$NHSO_2$(phenyl), and —$NHSO_2(C_1$-$C_4$ haloalkyl);

$R_3$ is hydrogen;
$R_4$ is hydrogen; and
$R_5$ is hydrogen.

2. At least one chemical entity of claim 1, wherein $R_1$ is optionally substituted with one or more groups independently chosen from
 —OH,
 —$NR^bR^c$, wherein $R^b$ is chosen from hydrogen or $C_1$-$C_6$ alkyl optionally substituted with one or two groups independently chosen from —OH and —$OC_1$-$C_4$ alkyl, and
 $R^c$ is independently chosen from hydrogen and $C_1$-$C_4$ alkyl optionally substituted with one or two groups independently chosen from —OH and —$OC_1$-$C_4$ alkyl,
 heterocycloalkyl optionally substituted with one or two groups independently chosen from —OH, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl,
 $C_1$-$C_6$ alkyl optionally substituted with one or two groups independently chosen from —OH, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl, and
 —$OC_1$-$C_6$ alkyl optionally substituted with one or two groups independently chosen from —OH, $C_3$-$C_6$ cycloalkyl, $C_1$-$C_4$ alkyl, —$C_1$-$C_4$ alkyl-OH, —$C_1$-$C_4$ alkyl-O—$C_1$-$C_4$ alkyl, —$C_1$-$C_4$ alkyl-$NH_2$, —$N(C_1$-$C_4$ alkyl)($C_1$-$C_4$ alkyl), —$NH(C_1$-$C_4$ alkyl), and —$OC_1$-$C_4$ alkyl.

3. At least one chemical entity of claim 1, wherein $R_1$ is optionally substituted with one or more groups independently chosen from:
 —OH,
 —$OC_1$-$C_6$ alkyl optionally substituted with one or two groups independently chosen from —OH, —$OC_1$-$C_4$ alkyl, $NH_2$, —$N(C_1$-$C_4$ alkyl)($C_1$-$C_4$ alkyl), and —$NH(C_1$-$C_4$ alkyl),
 heterocycloalkyl optionally substituted with one or two groups independently chosen from —OH, —$OC_1$-$C_4$ alkyl, —$C_1$-$C_4$ alkyl-OH, and $C_1$-$C_4$ alkyl,
 $C_1$-$C_6$ alkyl optionally substituted with —OH, and
 —$NR^bR^c$, wherein $R^b$ is chosen from H or $C_1$-$C_6$ alkyl optionally substituted with one or two groups independently chosen from —OH and —$OC_1$-$C_4$ alkyl, and $R^c$ is independently chosen from hydrogen and $C_1$-$C_4$ alkyl optionally substituted with one or two groups independently chosen from —OH and —$OC_1$-$C_4$ alkyl.

4. At least one chemical entity of claim 1, wherein $R_1$ is optionally substituted with one or more groups chosen from —OH and —$OC_1$-$C_6$ alkyl optionally substituted with one or two groups independently chosen from —OH, —$OC_1$-$C_4$ alkyl, and —$N(C_1$-$C_4$ alkyl)($C_1$-$C_4$ alkyl).

5. At least one chemical entity of claim 1, wherein $R_1$ is 6-morpholinopyridin-3-yl, ((2-methoxyethyl)(methyl)amino)pyridin-3-yl, ((2-hydroxyethyl)(methyl)amino)pyridin-3-yl, or 2-methoxypyridin-4-yl.

6. At least one chemical entity of claim 1, wherein $R_2$ is dihydroindolinyl optionally substituted with one or more groups independently chosen from oxo and $C_1$-$C_6$ alkyl, or dihydrobenzoxazinyl optionally substituted with oxo.

7. At least one chemical entity of claim 1, wherein $R_2$ is 2,3-dimethyl-2H-indazol-6-yl, 1H-indazol-6-yl, 1-methyl-1H-indazol-5-yl, 1-methyl-1H-indazol-6-yl, 3,4-dihydro-2H-1,4-benzoxazin-3-on-6-yl, 1,3-benzoxazol-6-yl, 3-aminoquinolin-6-yl, or 2,3-dihydro-1H-indolin-6-yl.

8. At least one chemical entity of claim 1, wherein $R_2$ is 1H-indazol-6-yl, 1-methyl-1H-indazol-5-yl, 1-methyl-1H-indazol-6-yl, 3,4-dihydro-2H-1,4-benzoxazin-3-on-6-yl, 1,3-benzoxazol-6-yl, 3-aminoquinolin-6-yl, or 2,3-dihydro-1H-indolin-6-yl.

9. A pharmaceutical composition comprising at least one chemical entity of claim 1, together with at least one pharmaceutically acceptable vehicle chosen from carriers, adjuvants, and excipients.

10. At least one chemical entity selected from:

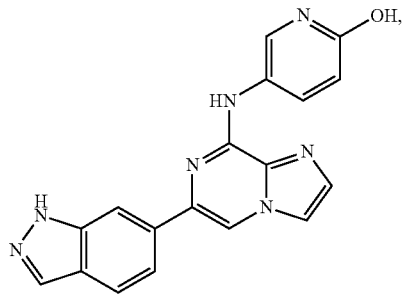

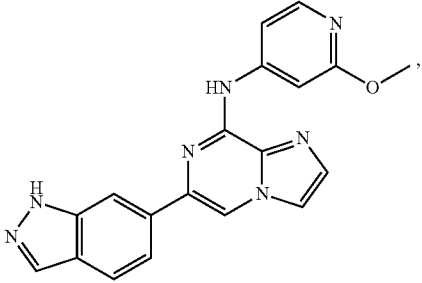

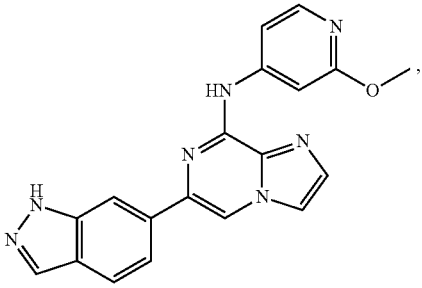

75
-continued
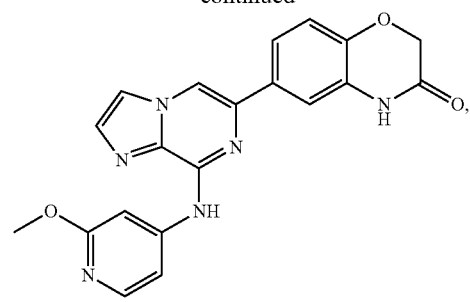
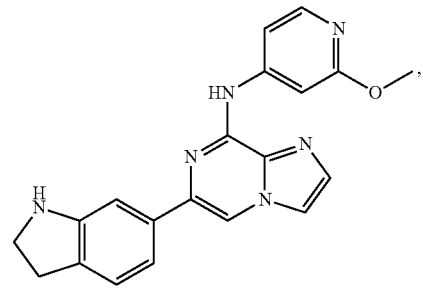
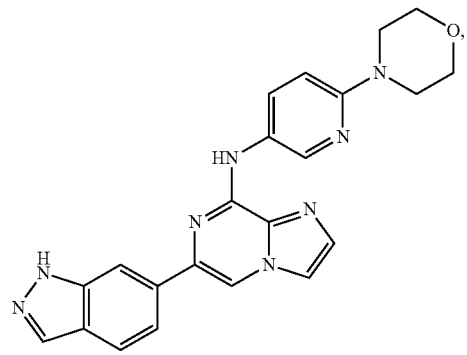
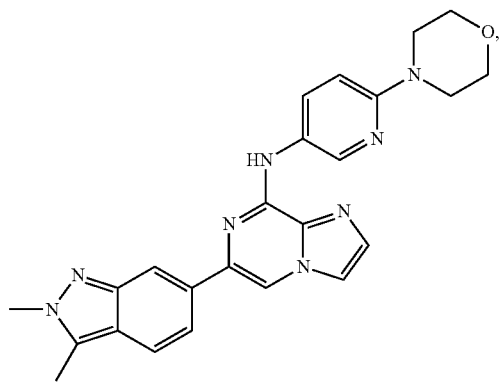
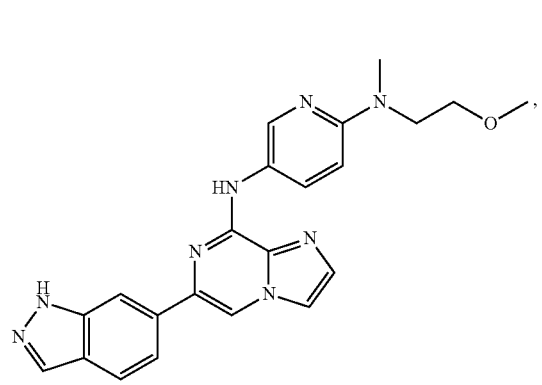
76
-continued
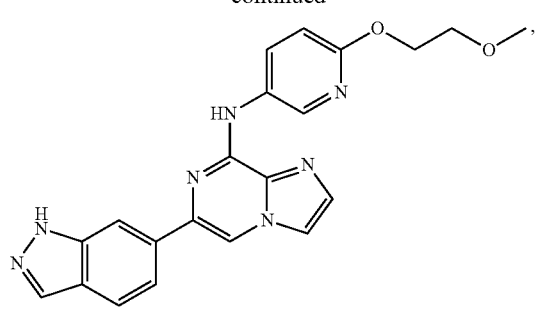
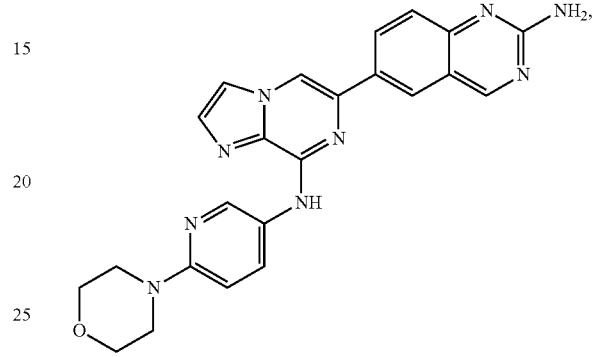
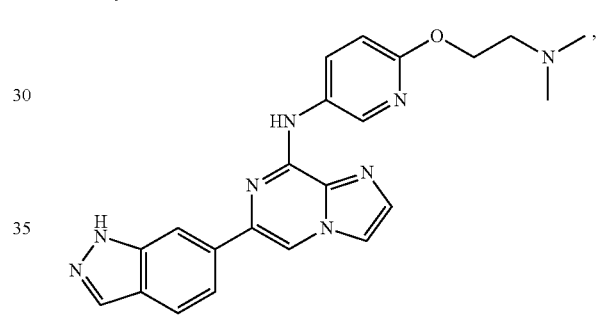
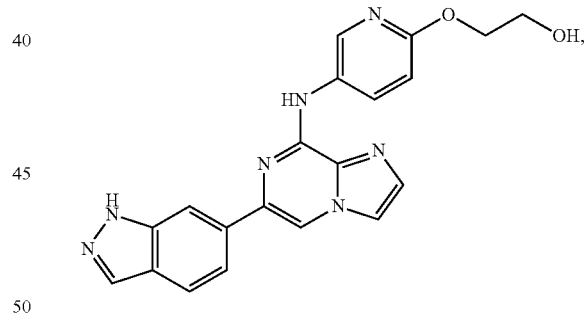
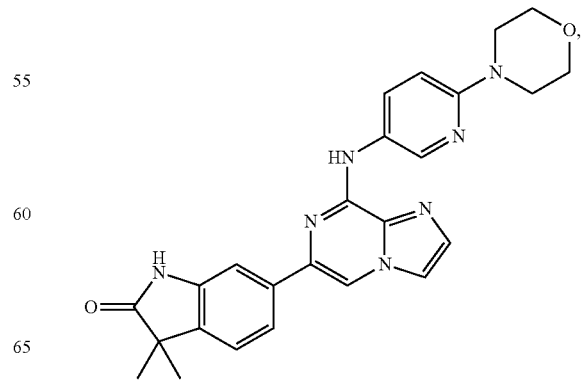

77
-continued
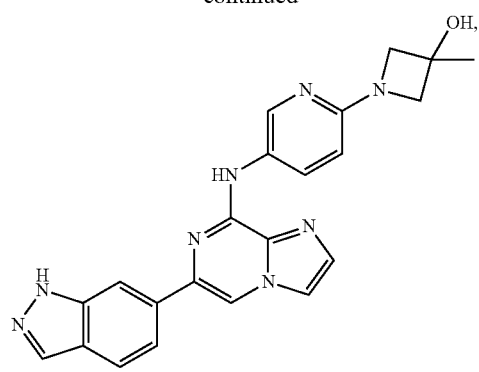
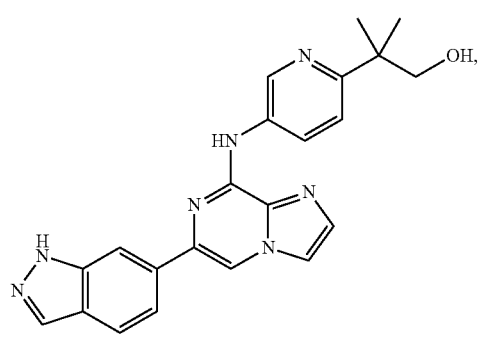
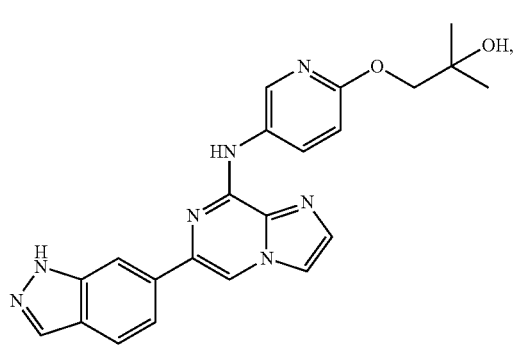
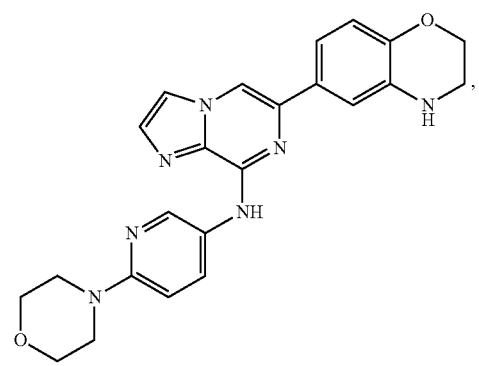
78
-continued
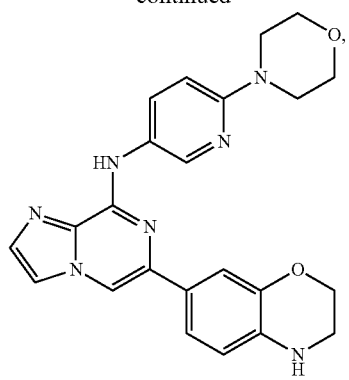
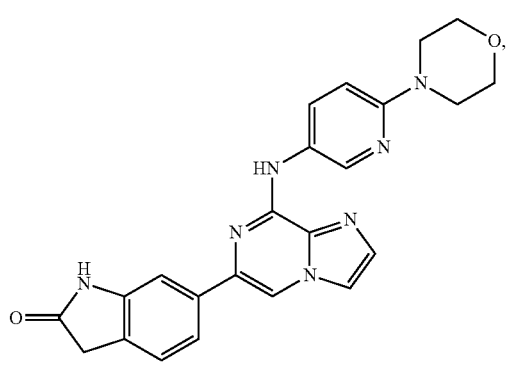
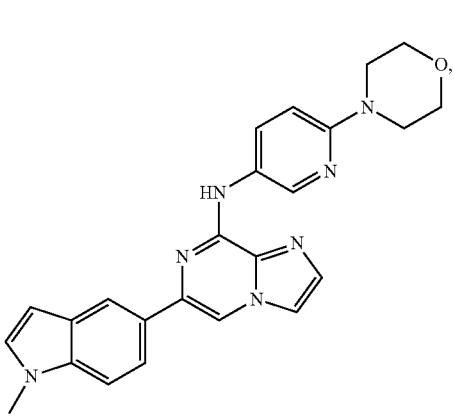
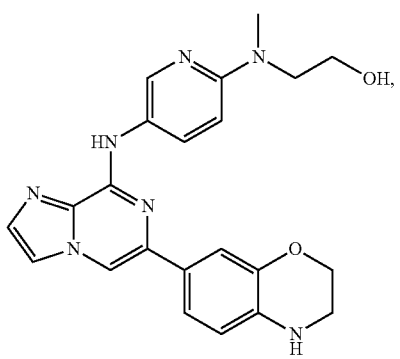

79
-continued
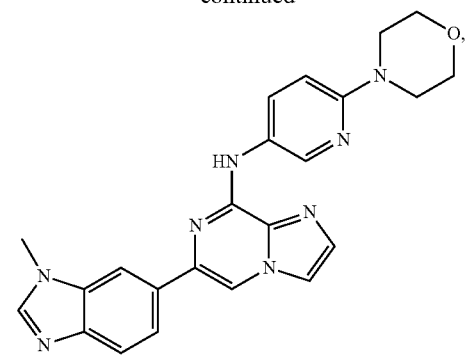
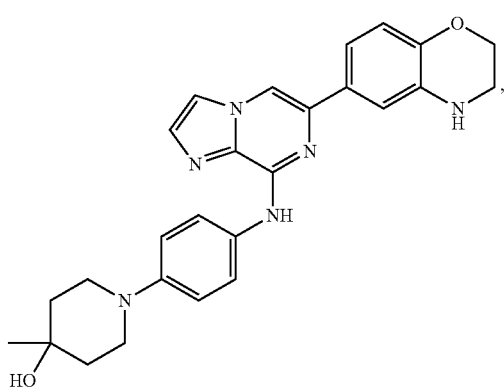
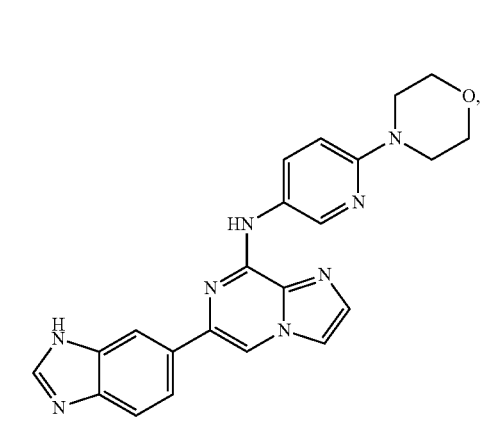
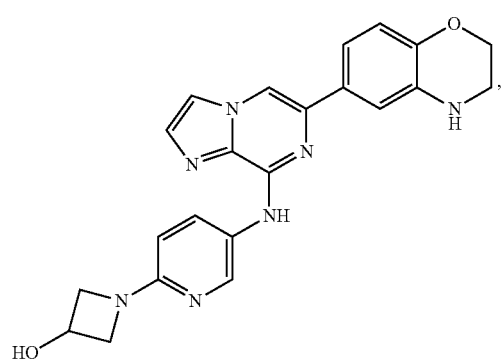
80
-continued
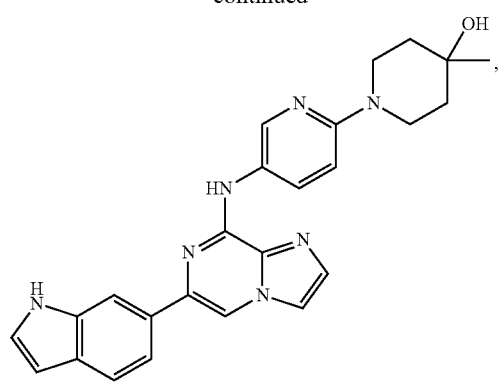
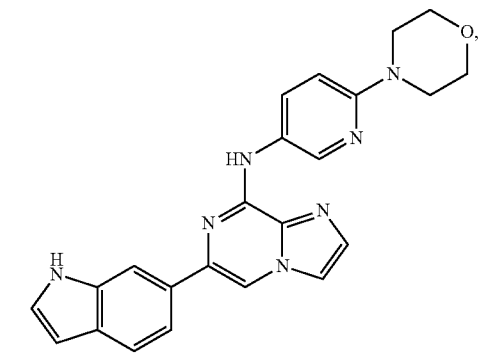
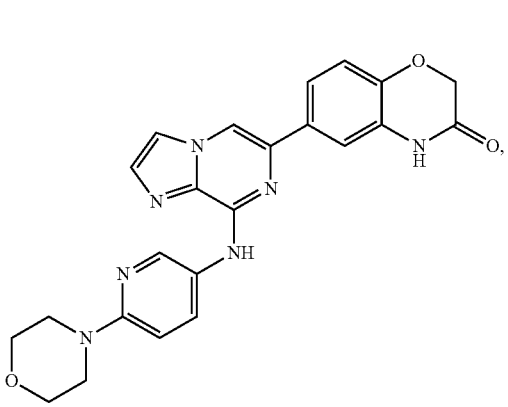
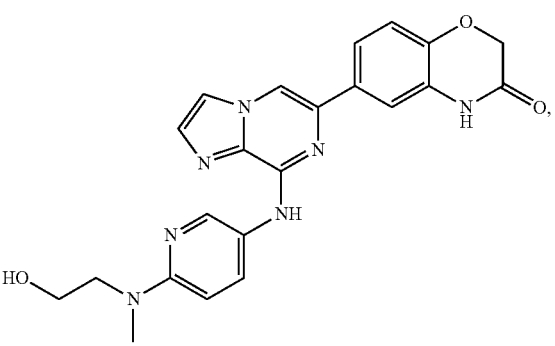

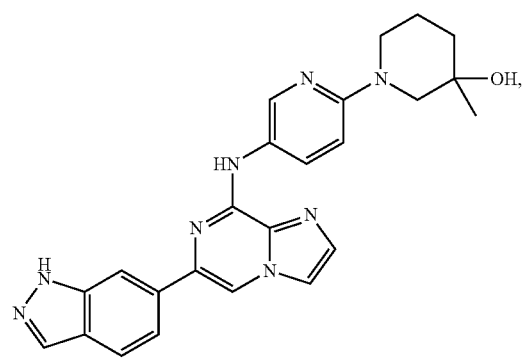
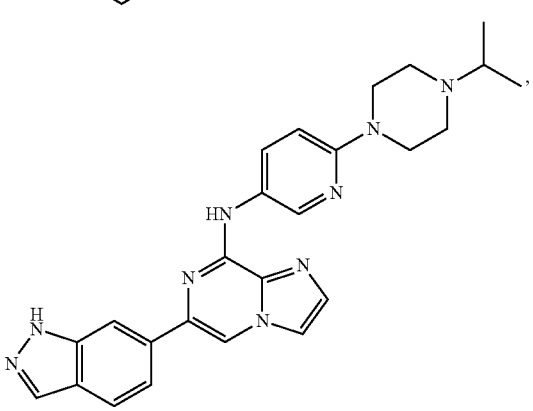
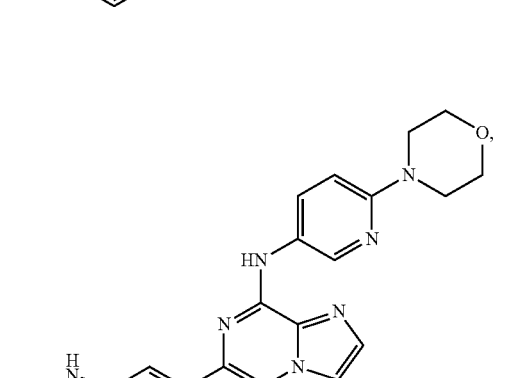
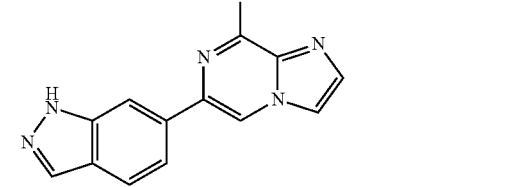
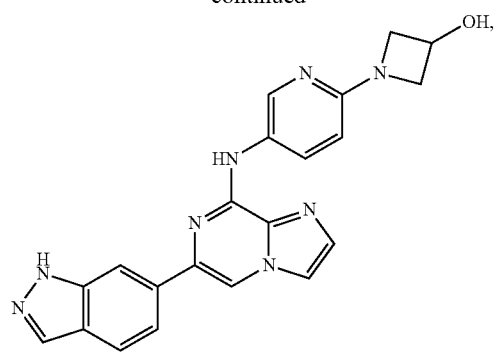
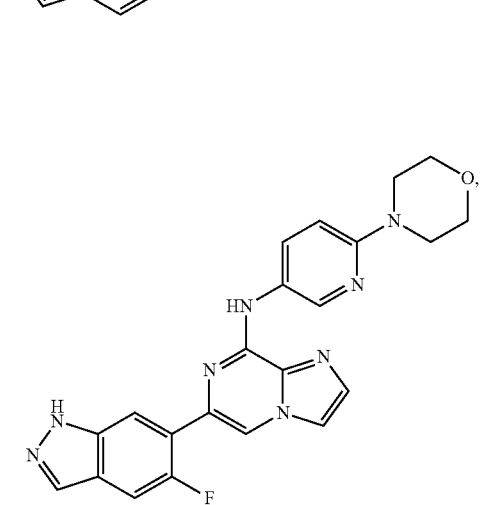
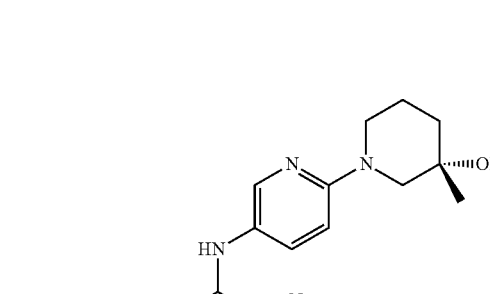
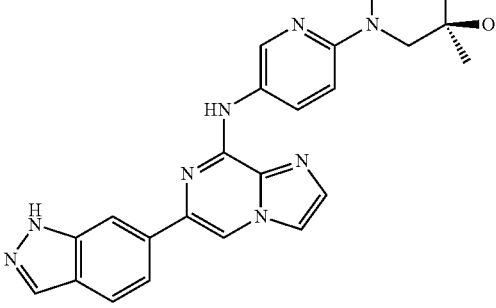

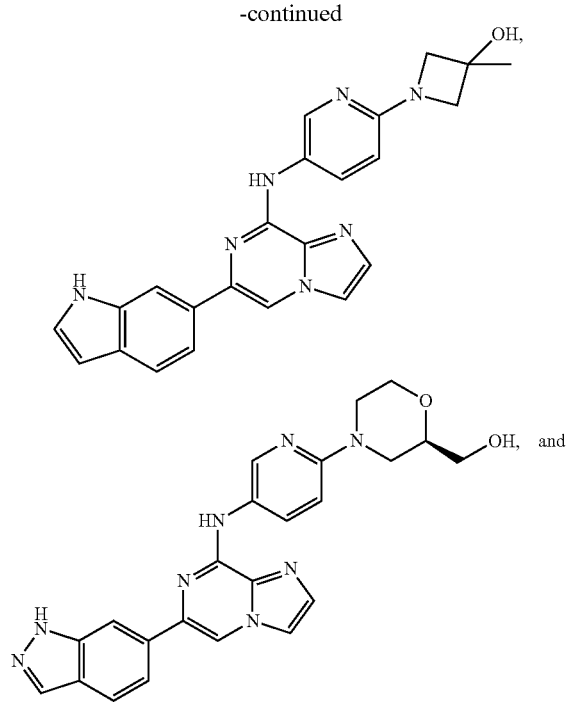
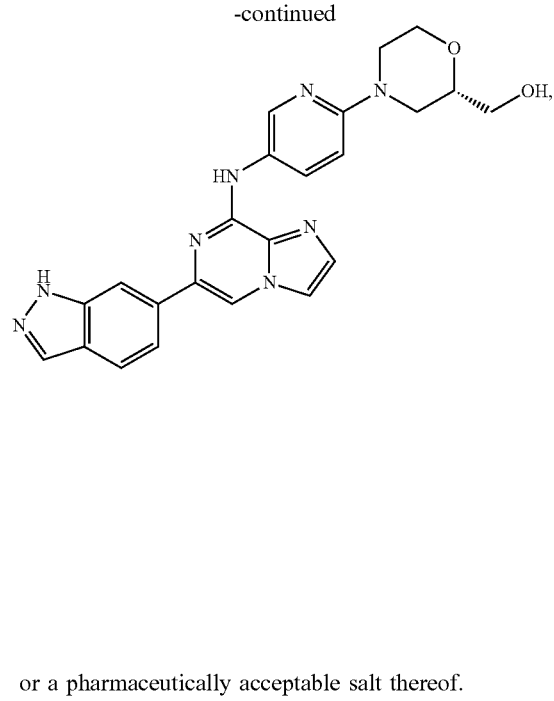
or a pharmaceutically acceptable salt thereof.
* * * * *